US009957297B2

(12) United States Patent
Jung et al.

(10) Patent No.: US 9,957,297 B2
(45) Date of Patent: May 1, 2018

(54) TEMPLATE-FIXED PEPTIDOMIMETICS AS INHIBITORS OF FPR1

(71) Applicant: POLYPHOR AG, Allschwil (CH)

(72) Inventors: Françoise Jung, Huningue (FR); Daniel Obrecht, Bättwil (CH); Ralf Löwe, Arlesheim (CH); Johann Zimmermann, Auggen (DE); Guillaume Lemercier, Village-Neuf (CH); Eric Chevalier, Steinbrunn-le-bas (FR)

(73) Assignee: POLYPHOR AG, Allschwil (CH)

( * ) Notice: Subject to any disclaimer, the term of this patent is extended or adjusted under 35 U.S.C. 154(b) by 0 days. days.

(21) Appl. No.: 14/349,683

(22) PCT Filed: Oct. 2, 2012

(86) PCT No.: PCT/EP2012/069412
§ 371 (c)(1),
(2) Date: Apr. 4, 2014

(87) PCT Pub. No.: WO2013/050346
PCT Pub. Date: Apr. 11, 2013

(65) Prior Publication Data
US 2014/0287986 A1     Sep. 25, 2014

(30) Foreign Application Priority Data

Oct. 7, 2011   (EP) .................................... 11008121

(51) Int. Cl.
| | | |
|---|---|---|
| A61K 38/00 | (2006.01) |
| C07K 14/47 | (2006.01) |
| A01N 37/18 | (2006.01) |
| A61P 31/04 | (2006.01) |
| A61P 23/00 | (2006.01) |
| A61P 17/00 | (2006.01) |
| A61P 29/00 | (2006.01) |
| A61P 35/00 | (2006.01) |
| A61K 38/10 | (2006.01) |
| A61K 38/12 | (2006.01) |
| C07K 5/00 | (2006.01) |
| C07K 7/00 | (2006.01) |
| C07K 16/00 | (2006.01) |
| C07K 17/00 | (2006.01) |
| C07K 1/00 | (2006.01) |
| C07K 7/08 | (2006.01) |
| C07K 7/64 | (2006.01) |

(52) U.S. Cl.
CPC . *C07K 7/08* (2013.01); *C07K 7/64* (2013.01)

(58) Field of Classification Search
CPC .................................. C07K 7/64; A61K 38/12
See application file for complete search history.

(56) References Cited

FOREIGN PATENT DOCUMENTS

| WO | WO 2004/018503 A1 | 3/2004 | |
|---|---|---|---|
| WO | WO 2005/075505 A1 | 8/2005 | |
| WO | WO 2005075505 A1 * | 8/2005 | ........... C07K 5/0821 |

OTHER PUBLICATIONS

Vippagunta et al. "Crystalline Solids" Adv. Drug Deliv. Rev. 48:3-26. Published 2001.*
Anonymous. "FPR1 Gene—Gene Cards" http://www.genecards.org/cgi-bin/carddispl.pl?gene=FPR1. Published Nov. 6, 2011.*
International Search Report issued in PCT/EP2012/069412, dated Dec. 12, 2012.

* cited by examiner

*Primary Examiner* — Christina Bradley
*Assistant Examiner* — Zachary J. Miknis
(74) *Attorney, Agent, or Firm* — Birch, Stewart, Kolasch & Birch, LLP

(57) ABSTRACT

Novel template-fixed β-hairpin peptidomimetics of the general formula (I): cyclo[$P^1$-$P^2$-$P^3$-$P^4$-$P^5$-$P^6$-$P^7$-$P^8$-$P^9$-$P^{10}$-$P^{11}$-$P^{12}$-$P^{13}$-$P^{14}$-$T^1$-$T^2$] wherein the single elements T or P are α-amino acid residues connected in either direction which, depending on their positions in the chain, are as defined in the description and the claims, and salts thereof, have the property of antagonizing the biological effect of the receptor FPR1. They can be used as medicaments to treat or prevent diseases or conditions in the areas of inflammatory diseases, allergic conditions, immunological disorders, neuroinflammation, neurological disorders, obstructive airway diseases, infectious diseases, ischemic reperfusion injuries and proliferative disorders such as e.g. cancer. These β-hairpin peptidomimetics can be manufactured by a process which is based on a mixed solid- and solution phase synthetic strategy.

12 Claims, No Drawings

SEQUENCE LISTING

<160> NUMBER OF SEQ ID NOS: 92

<210> SEQ ID NO 1
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 1

Glu His Lys Cys His Gly Xaa Trp Thr Ile Cys Tyr Glu Lys Xaa Pro
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Dab
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 2

Xaa His Lys Cys His Gly Xaa Trp Thr Ile Cys Tyr Glu Lys Xaa Glu
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 3

Tyr His Lys Cys His Gly Xaa Trp Thr Ile Cys Tyr Glu Lys Xaa Glu
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)

-continued

```
<223> OTHER INFORMATION: DAla
<220> FEATURE:
<221> NAME/KEY: MISC_FEATURE
<222> LOCATION: (15)..(15)
<223> OTHER INFORMATION: DPro

<400> SEQUENCE: 4

Tyr His Lys Cys His Gly Xaa Trp Thr Ile Cys Tyr Glu Lys Xaa Glu
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DLys

<400> SEQUENCE: 5

Tyr His Lys Cys His Gly Xaa Trp Thr Ile Cys Tyr Glu Lys Xaa Glu
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DAla

<400> SEQUENCE: 6

Tyr His Lys Cys His Gly Xaa Trp Thr Ile Cys Tyr Glu Lys Xaa Glu
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 7

Tyr His Ala Cys Trp Gly Xaa Trp Thr Ile Cys Tyr Gln Lys Xaa Glu
1               5                   10                  15

<210> SEQ ID NO 8
<211> LENGTH: 16
<212> TYPE: PRT
<213> ORGANISM: Artificial Sequence
```

<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 8

Tyr His Ala Cys His Gly Xaa Trp Thr Ile Cys Tyr Gln Lys Xaa Trp
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 9

Tyr His Ala Cys Trp Gly Xaa Trp Thr Ile Cys Tyr Gln Lys Xaa Ala
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 10

Tyr His Trp Cys Trp Gly Xaa Trp Thr Ile Cys Tyr Gln Lys Xaa Pro
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 11

Tyr His Trp Cys His Gly Xaa Trp Thr Ile Cys Tyr Gln Lys Xaa Pro
1               5                   10                  15

```
<210> SEQ ID NO 12
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 12

Tyr His Thr Cys His Gly Xaa Trp Thr Ile Cys Tyr Gln Lys Xaa Pro
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 13

Tyr His Lys Cys Trp Gly Xaa Trp Thr Ile Cys Tyr Gln Lys Xaa Pro
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 14

Tyr His Ile Cys His Gly Xaa Trp Thr Ile Cys Tyr Gln Lys Xaa Pro
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro
```

-continued

<400> SEQUENCE: 15

Tyr His Glu Cys His Gly Xaa Trp Thr Ile Cys Tyr Gln Lys Xaa Pro
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 16

Tyr His Ala Cys His Gly Xaa Trp Thr Ile Cys Tyr Trp Lys Xaa Pro
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 17

Tyr His Ala Cys Trp Gly Xaa Trp Thr Ile Cys Tyr Glu Lys Xaa Pro
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 18

Tyr His Ala Cys Trp Gly Xaa Trp Thr Ile Cys Tyr Trp Lys Xaa Pro
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro

```
<220> FEATURE:
<221> NAME/KEY: MISC_FEATURE
<222> LOCATION: (15)..(15)
<223> OTHER INFORMATION: DPro

<400> SEQUENCE: 19

Tyr His Ala Cys Trp Gly Xaa Trp Thr Ile Cys Tyr Gln Glu Xaa Pro
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 20

Tyr His Ala Cys Trp Gly Xaa Trp Thr Ile Cys Tyr Gln Ala Xaa Pro
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 21

Tyr His Ala Cys His Gly Xaa Trp Thr Ile Cys Tyr Gln Glu Xaa Pro
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 22

Tyr His Ala Cys Phe Gly Xaa Trp Thr Ile Cys Tyr Gln Lys Xaa Pro
1               5                   10                  15

<210> SEQ ID NO 23
<211> LENGTH: 16
<212> TYPE: PRT
<213> ORGANISM: Artificial Sequence
<220> FEATURE:
```

```
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 23

Tyr His Ala Cys Tyr Gly Xaa Trp Thr Ile Cys Tyr Gln Lys Xaa Pro
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 24

Glu His Ala Cys Trp Gly Xaa Trp Thr Ile Cys Tyr Gln Lys Xaa Pro
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 25

Thr His Ala Cys Trp Gly Xaa Trp Thr Ile Cys Tyr Gln Lys Xaa Pro
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 26

His His Ala Cys Trp Gly Xaa Trp Thr Ile Cys Tyr Gln Lys Xaa Pro
1               5                   10                  15
```

```
<210> SEQ ID NO 27
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 27

Ala His Ala Cys Trp Gly Xaa Trp Thr Ile Cys Tyr Gln Lys Xaa Pro
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 28

Lys His Ala Cys His Gly Xaa Trp Thr Ile Cys Tyr Gln Lys Xaa Pro
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 29

His Tyr Ala Cys Trp Gly Xaa Trp Thr Ile Cys Tyr Gln Lys Xaa Pro
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 30
```

Tyr His Ala Cys His Gly Xaa Trp Thr Ile Cys Tyr Glu Lys Xaa Pro
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 31

Tyr His Ala Cys Trp Gly Xaa Trp Thr Ile Cys Tyr Thr Lys Xaa Pro
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 32

Tyr His Ala Cys Trp Gly Xaa Trp Thr Ile Cys Tyr Ala Lys Xaa Pro
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 33

Tyr His Ala Cys His Gly Xaa Trp Thr Ile Cys Tyr Thr Lys Xaa Pro
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:

<221> NAME/KEY: MISC_FEATURE
<222> LOCATION: (15)..(15)
<223> OTHER INFORMATION: DPro

<400> SEQUENCE: 34

Tyr His Ala Cys Trp Gly Xaa Trp Thr Ile Cys Tyr Gln Lys Xaa Pro
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DAla
<220> FEATURE:
<221> NAME/KEY: MISC_FEATURE
<222> LOCATION: (15)..(15)
<223> OTHER INFORMATION: DPro

<400> SEQUENCE: 35

Tyr His Ala Cys Trp Gly Xaa Trp Thr Ile Cys Tyr Gln Lys Xaa Pro
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DAla
<220> FEATURE:
<221> NAME/KEY: MISC_FEATURE
<222> LOCATION: (15)..(15)
<223> OTHER INFORMATION: DPro

<400> SEQUENCE: 36

Tyr His Ala Cys His Gly Xaa Trp Thr Ile Cys Tyr Gln Lys Xaa Pro
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DLys

<400> SEQUENCE: 37

Tyr His Ala Cys Trp Gly Xaa Trp Thr Ile Cys Tyr Gln Lys Xaa Pro
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: synthetical construct

```
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DThr

<400> SEQUENCE: 38

Tyr His Ala Cys His Gly Xaa Trp Thr Ile Cys Tyr Gln Lys Xaa Pro
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DAla

<400> SEQUENCE: 39

Tyr His Ala Cys Trp Gly Xaa Trp Thr Ile Cys Tyr Gln Lys Xaa Pro
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 40

Tyr His Ala Cys Trp Gly Xaa Trp Thr Ile Cys Tyr Gln Lys Xaa Pro
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DAla

<400> SEQUENCE: 41

Tyr His Lys Cys His Gly Xaa Trp Thr Ile Cys Tyr Glu Lys Xaa Pro
1               5                   10                  15

<210> SEQ ID NO 42
```

```
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DAla

<400> SEQUENCE: 42

Tyr His Lys Cys Trp Gly Xaa Trp Thr Ile Cys Tyr Glu Lys Xaa Pro
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DLys

<400> SEQUENCE: 43

Tyr His Lys Cys Trp Gly Xaa Trp Thr Ile Cys Tyr Glu Lys Xaa Pro
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DLys

<400> SEQUENCE: 44

Tyr His Lys Cys His Gly Xaa Trp Thr Ile Cys Tyr Glu Lys Xaa Pro
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DTic

<400> SEQUENCE: 45
```

```
Tyr His Lys Cys His Gly Xaa Trp Thr Ile Cys Tyr Glu Lys Xaa Pro
1               5                   10                  15
```

<210> SEQ ID NO 46
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro((4S)OH)

<400> SEQUENCE: 46

```
Tyr His Lys Cys His Gly Xaa Trp Thr Ile Cys Tyr Glu Lys Xaa Pro
1               5                   10                  15
```

<210> SEQ ID NO 47
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro((4S)NH2)

<400> SEQUENCE: 47

```
Tyr His Lys Cys His Gly Xaa Trp Thr Ile Cys Tyr Glu Lys Xaa Pro
1               5                   10                  15
```

<210> SEQ ID NO 48
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPip
<400> SEQUENCE: 48

```
Tyr His Lys Cys His Gly Xaa Trp Thr Ile Cys Tyr Glu Lys Xaa Pro
1               5                   10                  15
```

<210> SEQ ID NO 49
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE -continued
<222> LOCATION: (15)..(15)
<223> OTHER INFORMATION: DPro

<400> SEQUENCE: 49

Tyr His Lys Cys Tyr Gly Xaa Trp Thr Ile Cys Tyr Glu Lys Xaa Pro
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (5)..(5)
<223> OTHER INFORMATION: Phe(4CF3)
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 50

Tyr His Lys Cys Xaa Gly Xaa Trp Thr Ile Cys Tyr Glu Lys Xaa Pro
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 51

Tyr His Lys Cys Trp Gly Xaa Trp Thr Ile Cys Tyr Glu Lys Xaa Pro
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (14)..(14)
<223> OTHER INFORMATION: Dab
<220> FEATURE:
<221> NAME/KEY: MISC_FEATURE
<222> LOCATION: (15)..(15)
<223> OTHER INFORMATION: DPro

<400> SEQUENCE: 52

Tyr His Lys Cys Trp Gly Xaa Trp Thr Ile Cys Tyr Glu Xaa Xaa Pro
1               5                   10                  15

```
<210> SEQ ID NO 53
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 53

Tyr His Lys Cys His Gly Xaa Trp Thr Ile Cys Tyr Glu Trp Xaa Pro
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 54

Tyr His Lys Cys His Gly Xaa Trp Thr Ile Cys Tyr Glu Glu Xaa Pro
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 55

Tyr His Lys Cys His Gly Xaa Trp Thr Ile Cys Tyr Glu His Xaa Pro
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (14)..(14)
<223> OTHER INFORMATION: Dab
<220> FEATURE:
```

<221> NAME/KEY: MISC_FEATURE
<222> LOCATION: (15)..(15)
<223> OTHER INFORMATION: DPro

<400> SEQUENCE: 56

Tyr His Lys Cys His Gly Xaa Trp Thr Ile Cys Tyr Glu Xaa Xaa Pro
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 57

Tyr His Lys Cys His Gly Xaa Trp Thr Ile Cys Tyr Glu Thr Xaa Pro
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 58

Tyr His Lys Cys His Gly Xaa Trp Thr Ile Cys Tyr Glu Gly Xaa Pro
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (14)..(14)
<223> OTHER INFORMATION: Hse
<220> FEATURE:
<221> NAME/KEY: MISC_FEATURE
<222> LOCATION: (15)..(15)
<223> OTHER INFORMATION: DPro

<400> SEQUENCE: 59

Tyr His Lys Cys His Gly Xaa Trp Thr Ile Cys Tyr Glu Xaa Xaa Pro
1               5                   10                  15

<210> SEQ ID NO 60
<211> LENGTH: 16

```
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 60

Tyr His Lys Cys His Gly Xaa Trp Thr Ile Cys Tyr Glu Lys Xaa Pro
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (3)..(3)
<223> OTHER INFORMATION: Orn
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 61

Tyr His Xaa Cys His Gly Xaa Trp Thr Ile Cys Tyr Glu Lys Xaa Pro
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DTic
<220> FEATURE:
<221> NAME/KEY: MISC_FEATURE
<222> LOCATION: (15)..(15)
<223> OTHER INFORMATION: DPro

<400> SEQUENCE: 62

Tyr His Lys Cys His Gly Xaa Trp Thr Ile Cys Tyr Glu Lys Xaa Pro
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro
```

```
<400> SEQUENCE: 63

Tyr His Lys Cys His Gly Xaa Trp Thr Ile Cys Tyr Trp Lys Xaa Pro
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 64

Tyr His Lys Cys His Gly Xaa Trp Thr Ile Cys Tyr Asp Lys Xaa Pro
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 65

Gly His Lys Cys His Gly Xaa Trp Thr Ile Cys Tyr Glu Lys Xaa Pro
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 66

Asp His Lys Cys His Gly Xaa Trp Thr Ile Cys Tyr Glu Lys Xaa Pro
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (1)..(1)
```

<223> OTHER INFORMATION: Dab
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 67

Xaa His Lys Cys His Gly Xaa Trp Thr Ile Cys Tyr Glu Lys Xaa Pro
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 68

His His Lys Cys His Gly Xaa Trp Thr Ile Cys Tyr Glu Lys Xaa Pro
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (1)..(1)
<223> OTHER INFORMATION: Dab
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 69

Xaa His Lys Cys Trp Gly Xaa Trp Thr Ile Cys Tyr Glu Lys Xaa Pro
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DAla
<220> FEATURE:
<221> NAME/KEY: MISC_FEATURE
<222> LOCATION: (15)..(15)
<223> OTHER INFORMATION: DPro

<400> SEQUENCE: 70

Tyr His Lys Cys Trp Gly Xaa Trp Thr Ile Cys Tyr Glu Lys Xaa Pro
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DAla
<220> FEATURE:
<221> NAME/KEY: MISC_FEATURE
<222> LOCATION: (15)..(15)
<223> OTHER INFORMATION: DPro

<400> SEQUENCE: 71

Tyr His Lys Cys His Gly Xaa Trp Thr Ile Cys Tyr Glu Lys Xaa Pro
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (13)..(13)
<223> OTHER INFORMATION: Dab
<220> FEATURE:
<221> NAME/KEY: MISC_FEATURE
<222> LOCATION: (15)..(15)
<223> OTHER INFORMATION: DPro

<400> SEQUENCE: 72

Tyr His Lys Cys Trp Gly Xaa Trp Thr Ile Cys Tyr Xaa Lys Xaa Pro
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (13)..(13)
<223> OTHER INFORMATION: Hse
<220> FEATURE:
<221> NAME/KEY: MISC_FEATURE
<222> LOCATION: (15)..(15)
<223> OTHER INFORMATION: DPro

<400> SEQUENCE: 73

Tyr His Lys Cys His Gly Xaa Trp Thr Ile Cys Tyr Xaa Lys Xaa Pro
1               5                   10                  15

<210> SEQ ID NO 74
<211> LENGTH: 16
<212> TYPE: PRT
<213> ORGANISM: Artificial Sequence

```
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 74

Tyr His Lys Cys His Gly Xaa Trp Thr Leu Cys Tyr Glu Lys Xaa Pro
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 75

Tyr His Lys Cys His Gly Xaa Trp Thr Val Cys Tyr Glu Lys Xaa Pro
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (8)..(8)
<223> OTHER INFORMATION: Phe(4CF3)
<220> FEATURE:
<221> NAME/KEY: MISC_FEATURE
<222> LOCATION: (15)..(15)
<223> OTHER INFORMATION: DPro

<400> SEQUENCE: 76

Tyr His Lys Cys His Gly Xaa Xaa Thr Ile Cys Tyr Glu Lys Xaa Pro
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 77
```

```
Tyr His Ile Cys His Gly Xaa Trp Thr Ile Cys Tyr Glu Lys Xaa Pro
1               5                   10                  15
```

<210> SEQ ID NO 78
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (3)..(3)
<223> OTHER INFORMATION: Dap
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 78

```
Tyr His Xaa Cys His Gly Xaa Trp Thr Ile Cys Tyr Glu Lys Xaa Pro
1               5                   10                  15
```

<210> SEQ ID NO 79
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 79

```
Tyr His Xaa Cys Trp Gly Xaa Trp Thr Ile Cys Tyr Glu Lys Xaa Pro
1               5                   10                  15
```

<210> SEQ ID NO 80
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (3)..(3)
<223> OTHER INFORMATION: Dab
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 80

```
Tyr His Xaa Cys His Gly Xaa Trp Thr Ile Cys Tyr Glu Lys Xaa Pro
1               5                   10                  15
```

```
<210> SEQ ID NO 81
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro
<220> FEATURE:
<221> NAME/KEY: MISC_FEATURE
<222> LOCATION: (16)..(16)
<223> OTHER INFORMATION: Pro((4S)NH2)

<400> SEQUENCE: 81

Tyr His Lys Cys His Gly Xaa Trp Thr Ile Cys Tyr Glu Lys Xaa Xaa
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro
<220> FEATURE:
<221> NAME/KEY: MISC_FEATURE
<222> LOCATION: (16)..(16)
<223> OTHER INFORMATION: Pro((4R)OH)

<400> SEQUENCE: 82

Tyr His Lys Cys His Gly Xaa Trp Thr Ile Cys Tyr Glu Lys Xaa Xaa
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro
<220> FEATURE:
<221> NAME/KEY: MISC_FEATURE
<222> LOCATION: (16)..(16)
<223> OTHER INFORMATION: Pro((4R)NH2)

<400> SEQUENCE: 83

Tyr His Lys Cys His Gly Xaa Trp Thr Ile Cys Tyr Glu Lys Xaa Xaa
1               5                   10                  15

<210> SEQ ID NO 84
<211> LENGTH: 16
<212> TYPE: PRT
```

```
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro((4R)OH)
<220> FEATURE:
<221> NAME/KEY: MISC_FEATURE
<222> LOCATION: (15)..(15)
<223> OTHER INFORMATION: DPro

<400> SEQUENCE: 84

Tyr His Lys Cys His Gly Xaa Trp Thr Ile Cys Tyr Glu Lys Xaa Pro
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (5)..(5)
<223> OTHER INFORMATION: Trp(5OH)
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 85

Tyr His Lys Cys Xaa Gly Xaa Trp Thr Ile Cys Tyr Glu Lys Xaa Pro
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 86

Tyr His Lys Cys His Gly Xaa Trp Thr Ile Cys Tyr Glu Lys Xaa Lys
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro
```

<400> SEQUENCE: 87

Tyr His Lys Cys Trp Gly Xaa Trp Thr Ile Cys Tyr Glu Lys Xaa Lys
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro

<400> SEQUENCE: 88

Tyr His Ala Cys Trp Gly Xaa Trp Thr Ile Cys Tyr Glu Lys Xaa Lys
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro
<220> FEATURE:
<221> NAME/KEY: MISC_FEATURE
<222> LOCATION: (16)..(16)
<223> OTHER INFORMATION: Dab

<400> SEQUENCE: 89

Tyr His Lys Cys His Gly Xaa Trp Thr Ile Cys Tyr Glu Lys Xaa Xaa
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro
<220> FEATURE:
<221> NAME/KEY: MISC_FEATURE
<222> LOCATION: (16)..(16)
<223> OTHER INFORMATION: Pip

<400> SEQUENCE: 90

Tyr His Lys Cys His Gly Xaa Trp Thr Ile Cys Tyr Glu Lys Xaa Xaa
1               5                   10                  15

<210> SEQ ID NO 91
<211> LENGTH: 16

```
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro
<220> FEATURE:
<221> NAME/KEY: MISC_FEATURE
<222> LOCATION: (16)..(16)
<223> OTHER INFORMATION: Tic

<400> SEQUENCE: 91

Tyr His Lys Cys His Gly Xaa Trp Thr Ile Cys Tyr Glu Lys Xaa Xaa
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: synthetical construct
<220> FEATURE:
<221> NAME/KEY: MISC_FEATURE
<222> LOCATION: (7)..(7)
<223> OTHER INFORMATION: DPro
<220> FEATURE:
<221> NAME/KEY: MISC_FEATURE
<222> LOCATION: (15)..(15)
<223> OTHER INFORMATION: DPro
<220> FEATURE:
<221> NAME/KEY: MISC_FEATURE
<222> LOCATION: (16)..(16)
<223> OTHER INFORMATION: Oic

<400> SEQUENCE: 92

Tyr His Lys Cys His Gly Xaa Trp Thr Ile Cys Tyr Glu Lys Xaa Xaa
1               5                   10                  15
```

TEMPLATE-FIXED PEPTIDOMIMETICS AS INHIBITORS OF FPR1

The present invention provides peptidomimetics incorporating a chain of 14 α-amino acid residues as defined below attached to a template which provides specific structural constraints for a β-hairpin like conformation. These template-fixed β-hairpin mimetics are able to inhibit the biological function of Formyl-Peptide Receptor 1, abbreviated FPR1, and are thus useful as pharmaceuticals in the treatment of a variety of diseases and disorders. The present invention also relates to pharmaceutical compositions and forms comprising one or more of these compounds and efficient processes for the preparation and production of these compounds and their intermediates.

Many medically relevant biological processes are mediated by signal transduction that involves G protein-coupled receptors (GPCRs) and a plethora of their endo- or exogenic ligands. One of the best characterized groups of GPCRs, already dated back to the early 1970s, are the formyl peptide receptors (FPRs) (N. Schiffmann et al., Proc. Nat. Acad. Sci., 1975, 72, 1059-1062). This group represents a classical type of seven-trans-membrane domain receptors with pattern recognition for different chemoattractant s, especially for small formylated peptide fragments such as e.g. N-formyl-methionyl-leucyl-phenylalanine (fMLF). In human three members, FPR1, FPR2ALX and FPR3, have been identified and are all genetically clustered in the same chromosomal region (19q13.3), whereas in rodents at least eight equivalents have been described.

Being widely promiscuous for their ligands, these chemoattractant receptors are a major cornerstone in the host innate immune system to fight infections, other xeno-biotics and tissue damages. According to this major function, expression levels are upregulated predominantly in different phagocytic leucocytes but can as well be found in certain tissues as indicated below for the different receptors.

The activation of FPR family members for example in leucocytes by chemoattractants induces GPCR coupling to $G_i\alpha_2$ or $G_i\alpha_3$, which triggers multiple secondary messengers through phospholipase C, D and $A_2$ activation (H. Ali et al., J. Biol. Chem., 1999, 274, 6027-6030). Subsequently shape changes, chemotaxis, adhesion, phagocytosis and/or the release of superoxide anions and other granule contents, leading to tissue damage can be observed in this disease state of inflammation or e.g. after infarction (Y. Le et al., Cytokine Growth Factor Rev., 2001, 12, 91-105; F. Gavins, Trends in Pharm. Sciences, 2010, 31, 266-276).

FPR1 was initially identified in phagocytic leukocytes as a high affinity receptor for the bacterial chemotactic peptide fMLF and other formyl-peptides and is an important key factor of the innate host defense against microbial infections. It has been reported to mediate proinflammatory and antibacterial host responses (P. Murphy et al., Annu. Rev. Immunol., 1994, 12, 593-633; J.-F. Gauthier et al., Infection and Immunity, 2007, 5361-5367; R. Ye, P. Murphy et al., Pharmacol. Rev., 2009, 61, 119-161 and cited literature therein). In addition FPR1 has been found in a broad variety of different cell types and tissues not only involved in inflammation, such as endothelial cells, neutrophils, monocytes, astrocytes or dendritic cells, but as well in e.g. malignant tumor cells of hematopoietic origin or glioblastoma cells (Y. Le et al., J. Neuroimmunol., 2000, 111, 102-108; J. Huang et al., Cancer Letters, 2008, 267, 254-261).

Due to the promiscuous behavior of the FPR1 receptor, quite an array of different natural and synthetic ligands is known. Besides the already mentioned plurality of specific formyl-peptide ligands, other classes of microbe derived ligands contain structures like e.g. T20 (DP178) from HIV gp41 (S. Su et al., Blood, 1999, 93, 11, 3885-3892). In addition host derived agonists include the variety of e.g. the peptidase cathepsin G, the phospholipid-binding protein Annexin 1 and specific fragments thereof as well as formyl peptides of mitochondrial origin (R. Sun et al., J. Immunol., 2005, 173, 428-436; M. J. Rabiet et al., Eur. J. Immunol., 2005, 35, 2486-2495). There are various antagonists known as well, especially those formed by replacing the N-formyl group for example in fMLP by a t-butoxycarbonyl (t-Boc) or isopropyl urea group. Some more specific inhibitory ligands from natural sources are e.g. Coronavirus peptides, Spinorphin, the bile acids deoxycholic acid (DCA) and chenodeoxycholic acid (CDCA), and, most prominent, Cyclosporin H and A. It has been shown that these ligands inhibit fMLP-induced monocyte and, in part, neutrophil migration and calcium mobilization, suggesting a mechanism for inhibition of inflammation and suppression of the innate immune response (e.g. P. Yan et al., J. of Immunol., 2006, 177, 7050-7085; F. Gavins, Trends in Pharm. Sciences, 2010, 31, 266-276 and cited literature therein).

In a more recent publication it is presented that FPR1 is positively associated with periodontitis and stomach cancer, suggesting a new point of interference in the progression of these diseases (T. Otani et al., Biochemical and Biophysical Research Communication, 2011, 405, 3, 356-361).

Therefore it would be advantageous to develop new chemical entities of limited complexity which address the need of binding selectively with high affinity to the FPR1 receptor and interfering with the corresponding specific downstream signaling activity to ameliorate the associated disease conditions.

The present invention provides now new chemical entities for a potential use as potent, selective and drugable modulators for the GPC receptor FPR1. In the compounds described below, a new strategy is utilized to stabilize β-hairpin conformations in backbone-cyclic peptidomimetics exhibiting selective antagonistic activity on the FPR1 receptor. This involves transplanting a loop sequence of a natural or unnatural biopolymer onto a template, whose function is to restrain the peptide loop backbone into a β-hairpin geometry.

Template-bound hairpin mimetic peptides have been described in the literature (D, Obrecht, M. Altorfer, J. A. Robinson, Adv. Med. Chem. 1999, 4, 1-68; J. A. Robinson, Syn. Lett. 2000, 4, 429-441) and the ability to generate β-hairpin peptidomimetics using combinatorial and parallel synthesis methods has now been established (L. Jiang, K. Moehle, B. Dhanapal, D. Obrecht, J. A. Robinson, Helv. Chim. Acta. 2000, 83, 3097-3112). These methods allow the synthesis and screening of large β-hairpin mimetic libraries, which in turn considerably facilitates structure-activity studies and hence the discovery of new molecules with potent and, especially, selective antagonizing activity.

There are few studies in the field describing 14mer peptides linked to a template as pharmaceutically active compounds, e.g. as antimicrobials in the international patent application WO02070547 A1 where specifically a disulfide interstrand linkage is present either from position $P^5$ to $P^{10}$ or from $P^3$ to $P^{12}$. Some other related publications describe template-fixed peptidomimetics as antagonists against the GPCR CXCR4. The cyclic peptidomimetics of this category, such as disclosed in the WIPO publications WO2004096840 A1 or WO2010127704 A1, feature different amino acid sequences in the peptidic chain part, e.g. being devoid of aromatic residues at position $P^5$, are conjugated to dyes (WO2006117011 A1) or half-life prolonging extended functionalities (WO2011066869 A1), or containing a different backbone connection, i.e. as depsipeptides in WO2010060479 A1.

The present invention is now providing novel compounds which differ significantly in structure leading to a specific affinity for the FPR1 receptor.

The β-Hairpin peptidomimetics obtained by the approach described here are useful as inhibitors of FPR1, i.e. as antagonists of downstream biological effects of this receptor and therefore as useful agents in the chemotherapy of especially the disease areas of inflammatory diseases, allergic conditions, immunological disorders, neuroinflammation, neurological disorders, obstructive airway diseases, infectious diseases, ischemic reperfusion injuries and proliferative disorders such as e.g. cancer.

Specific disease conditions falling under the areas described above are e.g. acute and chronic lung inflammation, COPD, asthma, emphysema, inflammation of the gastrointestinal tract, inflammatory bowel disease (IBD), Crohn's disease, acute skin inflammation, atopic dermatitis, eczema, psoriasis, rosacea, acne, neutrophilic dermatosis, neutrophil disorder, eosinophil disorder, monocytemacrophage associated diseases, Jobs syndrome, Chédiak-Higashi syndrome, chronic granulomatous disease, leukocyte adhesion deficiency, cystic fibrosis, peritonitis, periodontitis, sepsis, pneumonia, bacterial infection, and cancer.

The present invention relates to novel β-hairpin peptidomimetics of formula (I),

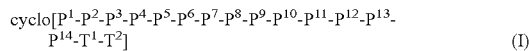

cyclo[$P^1$-$P^2$-$P^3$-$P^4$-$P^5$-$P^6$-$P^7$-$P^8$-$P^9$-$P^{10}$-$P^{11}$-$P^{12}$-$P^{13}$-$P^{14}$-$T^1$-$T^2$]    (I)

wherein the single elements T or P are connected in either direction from the carbonyl (C=O) point of attachment to the nitrogen (N) of the next element and wherein
$T^1$ is a naturally or non-naturally occurring D α-amino acid containing in total 1 to 25 carbon- and/or heteroatoms in a single side-chain;
$T^2$ is a naturally or non-naturally occurring L α-amino acid containing in total 1 to 25 carbon- and/or heteroatoms in a single side-chain;
$P^1$, $P^3$, $P^{12}$, $P^{13}$ and $P^{14}$ are independently
  Gly or a naturally or non-naturally occurring L α-amino acid containing in total 1 to 25 carbon- and/or heteroatoms in a single side-chain;
$P^2$, $P^5$ and $P^8$ are independently
  a naturally or non-naturally occurring aromatic L α-amino acid containing in total 1 to 25 carbon- and/or heteroatoms in a single side-chain;
$P^4$ and $P^{11}$ are
  naturally or non-naturally occurring cross-linking L α-amino acids containing each in total 1 to 12 carbon- and/or heteroatoms in a single side-chain which together are connecting $P^4$ and $P^{11}$ by covalent or electrostatic interaction;
$P^6$ is Gly;
$P^7$ is a naturally or non-naturally occurring D α-amino acid containing in total 1 to 25 carbon- and/or heteroatoms in a single side-chain;
$P^9$ is a naturally or non-naturally occurring alcoholic L α-amino acid containing in total 1 to 25 carbon- and/or heteroatoms in a single side-chain; and
$P^{10}$ is a naturally or non-naturally occurring aliphatic L α-amino acid containing in total 1 to 25 carbon- and/or heteroatoms in a single side-chain;

or a tautomer or rotamer thereof, or a salt, or a hydrate or solvate thereof.

A particular embodiment of the present invention relates to compounds according to general formula (I), wherein $T^1$ and $P^7$ are independently
  an D α-amino acid residue of one of the formulae

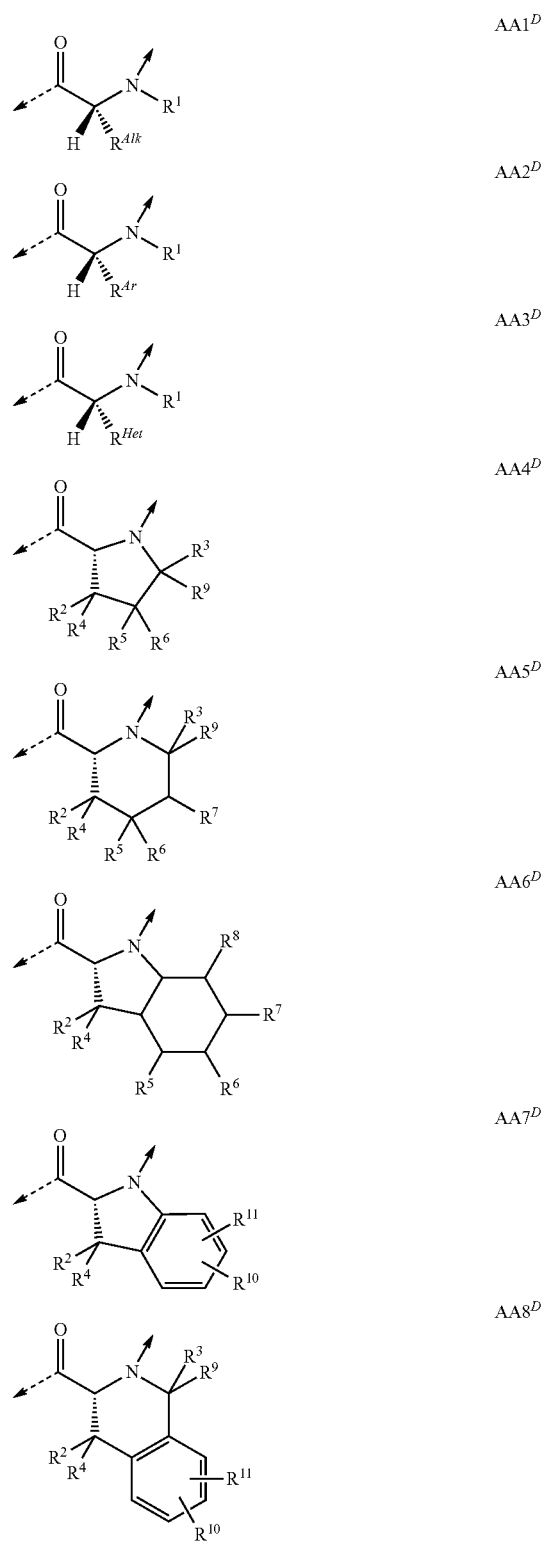

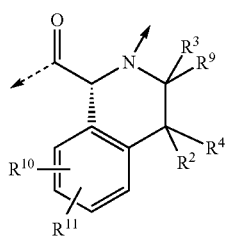
AA9$^D$
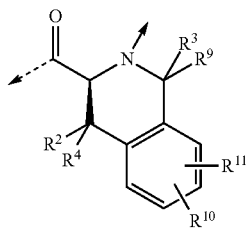
AA8
T$^2$ is an L α-amino acid residue of one of the formulae
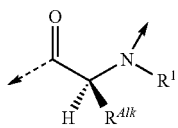
AA1
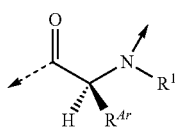
AA2
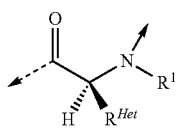
AA3
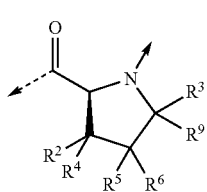
AA4
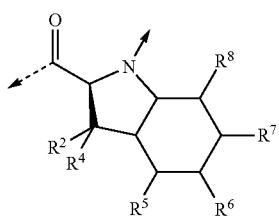
AA5
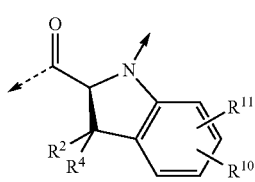
AA6
AA7
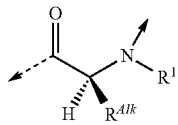
AA9
P$^1$, P$^3$, P$^{12}$, P$^{13}$ and P$^{14}$ are independently
Gly; or an L α-amino acid residue of one of the formulae
AA1
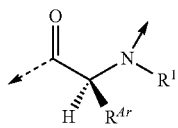
AA2
AA3
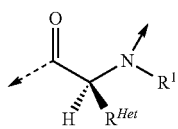
P$^2$, P$^5$ and P$^8$ are independently an L α-amino acid residue of formula
AA2
P$^4$ and P$^{11}$ taken together form an interstrand linking bis(amino acid)-structure of formula P⁶ is Gly;
P⁹ is an L α-amino acid residue of formula

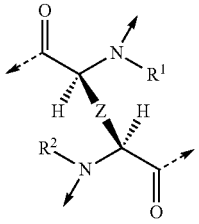

AA10

P¹¹ is an L α-amino acid residue of formula

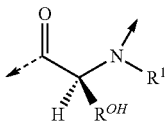

AA11

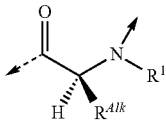

AA1

$R^{Alk}$ is with the proviso of containing less than 26 carbon- and/or heteroatoms,
$C_{1-12}$-alkyl; $C_{2-12}$-alkenyl; cycloalkyl; cycloalkyl-$C_{1-6}$-alkyl; or $C_{1-6}$-alkoxy-$C_{1-6}$-alkyl;

$R^{Ar}$ is, with the proviso of containing less than 26 carbon- and/or heteroatoms,
—$(CR^1R^4)_nR^{19}$; —$(CH_2)_n$—O—$(CH_2)_mR^{19}$; —$(CH_2)_nS(CH_2)_mR^{19}$; or —$(CH_2)_nNR^{14}(CH_2)_mR^{19}$;

$R^{Het}$ is with the proviso of containing less than 26 carbon- and/or heteroatoms, heterocycloalkyl; heterocycloalkyl-$C_{1-6}$-alkyl; heteroaryl; heteroaryl-$C_{1-6}$-alkyl;
—$(CR^1R^{13})_qNR^{15}R^{16}$; —$(CH_2)_qC(=NR^{13})NR^{15}R^{16}$;
—$(CH_2)_qC(=NOR^{17})NR^{15}R^{16}$;
—$(CH_2)_qC(=NNR^{15}R^{16})NR^{17}R^{18}$; —$(CR^1R^{13})_qNR^2C(=NR^{17})NR^{15}R^{16}$;
—$(CR^1R^{13})_qN=C(NR^{15}R^{16})NR^{17}R^{18}$; —$(CR^1R^{13})_qOR^{14}$; —$(CR^1R^{13})_qSR^{15}$; —$(CR^1R^{13})_qSO_2R^{15}$;
—$(CR^1R^{13})_qSO_2NR^1R^{14}$; —$(CR^1R^{13})_qSO_2NR^{15}R^{16}$;
—$(CR^1R^{13})_qNR^{14}SO_2R^{15}$;
—$(CR^1R^{13})_qNR^{14}SO_2NR^{15}R^{16}$; —$(CR^1R^{13})_qPO(OR^1)_2$;
—$(CH_2)_n$—O—$(CH_2)_mNR^{15}R^{16}$;
—$(CH_2)_n$—O—$(CH_2)_mC(=NR^{17})NR^{15}R^{16}$; —$(CH_2)_n$—O—$(CH_2)_mC(=NOR^{17})NR^{15}R^{16}$;
—$(CH_2)_n$—O—$(CH_2)_mC(=NNR^{15}R^{16})NR^{17}R^{18}$;
—$(CH_2)_n$—O—$(CH_2)_mNR^1C(=NR^{17})NR^{15}R^{16}$;
—$(CH_2)_n$—O—$(CH_2)_mN=C(NR^{15}R^{16})NR^{17}R^{18}$;
—$(CH_2)_nS(CH_2)_mNR^{15}R^{16}$;
—$(CH_2)_nS(CH_2)_mC(=NR^{17})NR^{15}R^{16}$; —$(CH_2)_nS(CH_2)_mC(=NOR^{17})NR^{15}R^{16}$;
—$(CH_2)_nS(CH_2)_mC(=NNR^{15}R^{16})NR^{17}R^{18}$; —$(CH_2)_nS(CH_2)_mNR^1C(=NR^{17})NR^{15}R^{16}$;
—$(CH_2)_nS(CH_2)_mN=C(NR^{15}R^{16})NR^{17}R^{18}$;
—$(CR^1R^{13})_qCOOR^{15}$; or —$(CR^1R^{13})_qCONR^{15}R^{16}$;

Z is, with the proviso of containing less than 25 carbon- and/or heteroatoms,
—$(CH_2)_n$—S—S—$(CH_2)_m$—; —$(CH_2)_nCH=CH(CH_2)_m$—; —$(CH_2)_n$-heteroaryl-$(CH_2)_m$—;
—$(CH_2)_nCONR^1(CH_2)_m$—; or —$(CH_2)_nNR^1CONR^2(CH_2)_m$—;

$R^{OH}$ is, with the proviso of containing less than 26 carbon- and/or heteroatoms,
—$(CR^1R^{13})_qOH$; —$(CR^1R^{13})_qSH$; —$(CH_2)_n$—O—$(CH_2)_mOH$; —$(CH_2)_nS(CH_2)_mOH$;
—$(CH_2)_nNR^1(CH_2)_mOH$; hydroxy-$C_{1-8}$-alkyl; hydroxy-$C_{2-8}$-alkenyl; hydroxy-cycloalkyl; or hydroxy-heterocycloalkyl;

$R^1$, $R^2$ and $R^3$ are independently
H; $CF_3$; $C_{1-8}$-alkyl; $C_{2-8}$-alkenyl; or aryl-$C_{1-6}$-alkyl;

$R^4$, $R^5$, $R^6$, $R^7$ and $R^8$ are independently
H; F; $CF_3$; $C_{1-8}$-alkyl; $C_{2-8}$-alkenyl; cycloalkyl; heterocycloalkyl; aryl; heteroaryl;
aryl-$C_{1-6}$-alkyl; heteroaryl-$C_{1-6}$-alkyl; —$(CHR^{13})_oOR^{15}$;
—$O(CO)R^{15}$; —$(CHR^{13})_oSR^{15}$;
—$(CHR^{13})_oNR^{15}R^{16}$; —$(CHR^{13})_oOCONR^{15}R^{16}$;
—$(CHR^{13})_oNR^1CONR^{15}R^{16}$;
—$(CHR^{13})_oNR^1COR^{15}$; —$(CHR^{13})_oCOOR^{15}$;
—$(CHR^{13})_oCONR^{15}R^{16}$; —$(CHR^{13})_oPO(OR^1)_2$;
—$(CHR^{13})_oSO_2R^{15}$; —$(CHR^{13})_oNR^1SO_2R^{15}$;
—$(CHR^{13})_oSO_2NR^{15}R^{16}$; —$(CR^1R^{13})_oR^{23}$; or
—$(CHR^1)_n$—O—$(CHR^2)_mR^{23}$; or $R^4$ and $R^2$; or $R^5$ and $R^6$ taken together can form:
=O; =$NR^1$; =$NOR^1$; =$NOCF_3$; or —$(CHR^1)_p$—;

$R^4$ and $R^5$; $R^6$ and $R^7$; $R^7$ and $R^8$; or $R^8$ and $R^9$ taken together can form:
—$(CHR^1)_p$—; —$(CH_2)_n$—O—$(CH_2)_m$—; —$(CH_2)_nS(CH_2)_m$—; or —$(CH_2)_nNR^1(CH_2)_m$—;

$R^9$ is H; F; $CF_3$; $C_{1-8}$-alkyl; $C_{2-8}$-alkenyl; cycloalkyl; heterocycloalkyl; aryl; heteroaryl;
aryl-$C_{1-6}$-alkyl; heteroaryl-$C_{1-6}$-alkyl; —$(CHR^{13})_rOR^{15}$;
—$O(CO)R^{15}$; —$(CHR^{13})_rSR^{15}$;
—$(CHR^{10})_rNR^{15}R^{16}$; —$(CHR^{13})_rOCONR^{15}R^{16}$;
—$(CHR^{13})_rNR^1CONR^{15}R^{16}$;
—$(CHR^{13})_rNR^1COR^{15}$; —$(CHR^{13})_oCOOR^{15}$;
—$(CHR^{13})_oCONR^{15}R^{16}$; —$(CHR^{13})_rPO(OR^1)_2$;
—$(CHR^{13})_rSO_2R^{15}$; —$(CHR^{13})_rNR^1SO_2R^{15}$;
—$(CHR^{13})_rSO_2NR^{15}R^{16}$; —$(CR^1R^{13})_oR^{23}$; or
—$(CHR^1)_r$—O—$(CHR^1)_oR^{23}$;

$R^{10}$, $R^{11}$ and $R^{12}$ are independently
H; F; Cl; Br; I; $CF_3$; $OCF_3$; $OCHF_2$; CN; $NO_2$; $C_{1-8}$-alkyl; $C_{2-8}$-alkenyl; aryl; heteroaryl;
aryl-$C_{1-6}$-alkyl; heteroaryl-$C_{1-6}$-alkyl; —$(CHR^{13})_oOR^{15}$;
—$O(CO)R^{15}$; —$(CHR^{13})_oSR^{15}$;
—$(CHR^{13})_oNR^{15}R^{16}$; —$(CHR^{13})_rOCONR^{15}R^{16}$;
—$(CHR^{13})_oNR^1CONR^{15}R^{16}$;
—$(CHR^{13})_oNR^1COR^{15}$; —$(CHR^{13})_oCOOR^{15}$;
—$(CHR^{13})_oCONR^{15}R^{16}$; —$(CHR^{13})_oPO(OR^1)_2$;
—$(CHR^{13})_oSO_2R^{15}$; —$(CHR^{13})_oNR^1SO_2R^{15}$;
—$(CHR^{13})_oSO_2NR^{15}R^{16}$; or —$(CR^1R^{13})_oR^{23}$;

$R^{13}$ is H; F; $CF_3$; $C_{IA}$-alkyl; $C_{2-8}$-alkenyl; cycloalkyl; heterocycloalkyl;
cycloalkyl-$C_{1-6}$-alkyl; heterocycloalkyl-$C_{1-6}$-alkyl; aryl; heteroaryl;
aryl-$C_{1-6}$-alkyl; heteroaryl-$C_{1-6}$-alkyl; —$(CHR^1)_oOR^{15}$;
—$OCOR^1$; —$(CHR^1)_oNR^{15}R^{16}$;
—$COOR^{15}$; —$CONR^{15}R^{16}$; —$SO_2R^{15}$; or —$SO_2NR^{15}R^{16}$;

$R^{14}$ is H; $CF_3$; $C_{IA}$-alkyl; $C_{2-8}$-alkenyl; cycloalkyl; heterocycloalkyl;
cycloalkyl-$C_{1-6}$-alkyl; heterocycloalkyl-$C_{1-6}$-alkyl; aryl; heteroaryl;
aryl-$C_{1-6}$-alkyl; heteroaryl-$C_{1-6}$-alkyl; cycloalkyl-aryl; heterocycloalkyl-aryl;

cycloalkyl-heteroaryl; heterocycloalkyl-heteroaryl; aryl-cycloalkyl;

aryl-heterocycloalkyl; heteroaryl-cycloalkyl; heteroaryl-heterocycloalkyl;

—(CHR$^1$)$_o$OR$^{15}$; —(CHR$^1$)$_o$SR$^{15}$; —(CHR$^1$)$_o$NR$^{15}$R$^{16}$; —(CHR$^1$)$_o$COOR$^{15}$;

—(CHR$^1$)$_o$CONR$^{15}$R$^{16}$; or —(CHR$^1$)$_o$SO$_2$R$^{15}$;

R$^{15}$, R$^{16}$, R$^{17}$ and R$^{18}$ are independently

H; C$_{1-4}$-alkyl; C$_{2-8}$-alkenyl; C$_{1-6}$-alkoxy; cycloalkyl; heterocycloalkyl;

cycloalkyl-C$_{1-6}$-alkyl; heterocycloalkyl-C$_{1-6}$-alkyl; aryl; heteroaryl;

aryl-C$_{1-6}$-alkyl; heteroaryl-C$_{1-6}$-alkyl; cycloalkyl-aryl; heterocycloalkyl-aryl;

cycloalkyl-heteroaryl; heterocycloalkyl-heteroaryl; aryl-cycloalkyl;

aryl-heterocycloalkyl; heteroaryl-cycloalkyl; or heteroaryl-heterocycloalkyl; or the structural elements —NR$^{15}$R$^{16}$ and —NR$^{17}$R$^{18}$ can independently form:

heterocycloalkyl; aryl-heterocycloalkyl; or heteroaryl-heterocycloalkyl;

R$^{19}$ is an aryl group of one of the formulae

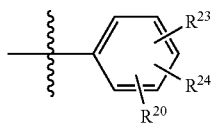

AR1

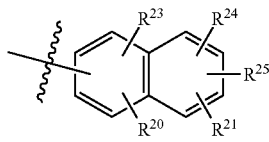

AR2 or a heteroaryl group of one of the formulae

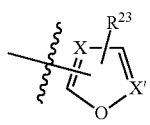

H1

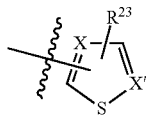

H2

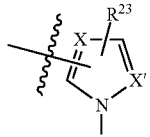

H3

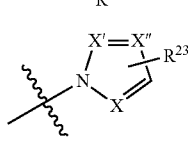

H4

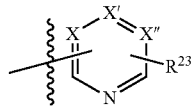

H5

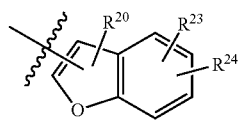

H6

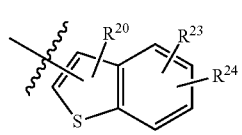

H7

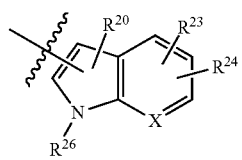

H8

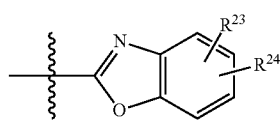

H9

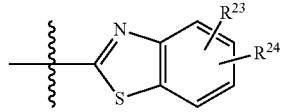

H10

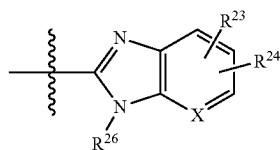

H10

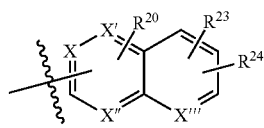

H12

H13

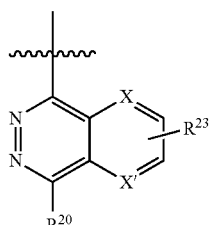

H14

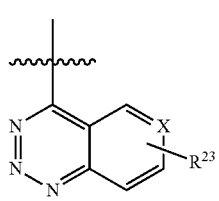

X, X', X'' and X''' are independently
—CR²⁰; or N;
R²⁰ and R²¹ are independently
H; F; Cl; Br; I; OH; NH₂; NO₂; CN; CF₃; OCHF₂; OCF₃;
C₁₋₈-alkyl; C₂₋₈-alkenyl; aryl;
heteroaryl; aryl-C₁₋₆-alkyl; heteroaryl-C₁₋₆-alkyl;
—(CH₂)ₒR²²; —(CH₂)ₒOR¹⁵; —O(CO)R¹⁵;
—O(CH₂)ₚR²²; —(CH₂)ₒSR¹⁵; —(CH₂)ₒNR¹⁵R¹⁶;
—(CH₂)ₒOCONR¹⁵R¹⁶;
—(CH₂)ₒNR¹CONR¹⁵R¹⁶; —(CH₂)ₒNR¹COR¹⁵;
—(CH₂)ₒCOOR¹⁵; —(CH₂)ₒCONR¹⁵R¹⁶;
—(CH₂)ₑPO(OR¹)₂; —(CH₂)ₒSO₂R¹⁴; or —(CH₂)ₒCOR¹⁵;
R²² is an aryl group of the formula

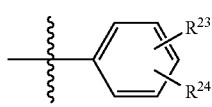

AR3

R²³, R²⁴ and R²⁵ are independently
H; F; Cl; Br; I; OH; NH₂; NO₂; CN; CF₃; OCHF₂; OCF₃;
C₁₋₈-alkyl; C₂₋₈-alkenyl;
—(CH₂)ₒOR¹⁵; —O(CO)R¹⁵; —(CH₂)ₒNR¹R¹⁵;
—(CH₂)ₒCOOR¹⁵; —(CH₂)ₒCONR¹R¹⁵;
R²⁶ is H; Ac; C₁₋₈-alkyl; or aryl-C₁₋₆-alkyl;
n and m are independently an integer of 0-5 with the proviso that n+m 6;
o is 0-4; p is 2-6; q is 1-6; and r is 1-3;
or pharmaceutically acceptable salts thereof.

Each single group "Rˣ" with the same index-number x for x=1–26 is independently selected on each occurrence in a specific formula and, therefore, they can be the same or different.

As used in this description, the term "alkyl", taken alone or in combinations (i.e. as part of another group, such as "aryl-C₁₋₆-alkyl") designates saturated, straight-chain or branched hydrocarbon radicals and may be optionally substituted. The term "$C_{x-y}$-alkyl" (x and y each being an integer) refers to an alkyl group as defined before containing x to y carbon atoms. For example a C₁₋₆-alkyl group contains one to six carbon atoms. Representative examples of alkyl groups include methyl, ethyl, n-propyl, iso-propyl, n-butyl, iso-butyl, sec-butyl, tert-butyl, n-pentyl, n-hexyl and the like.

The term "alkenyl", taken alone or in combinations, designates straight chain or branched hydrocarbon radicals containing at least one or, depending on the chain length, up to four olefinic double bonds. Such alkenyl moieties are optionally substituted and can independently exist as E or Z configurations per double bond, which are all part of the invention. The term "$C_{x-y}$-alkenyl" (x and y each being an integer) refers to an alkenyl group as defined before containing x to y carbon atoms.

The term "cycloalkyl", taken alone or in combinations, refers to a saturated or partially unsaturated alicyclic moiety having from three to ten carbon atoms and may be optionally substituted. Examples of this moiety include, but are not limited to, cyclohexyl, norbornyl, decalinyl and the like.

The term "heterocycloalkyl", taken alone or in combinations, describes a saturated or partially unsaturated mono- or bicyclic moiety having from three to nine ring carbon atoms and one or more ring heteroatoms selected from nitrogen, oxygen or sulphur. This term includes, for example, morpholino, piperazino, azetidinyl, pyrrolidinyl, tetrahydrofuranyl, piperidinyl, octahydro-1H-indolyl, 1,7-diazaspiro[4.4]nonane and the like. Said heterocycloalkyl ring(s) might be optionally substituted.

The term "aryl", taken alone or in combinations, designates aromatic carbocyclic hydrocarbon radicals containing one or two six-membered rings, such as phenyl or naphthyl, which may be optionally substituted by up to three substituents such as Br, Cl, F, CF₃, OH, OCF₃, OCHF₂, NH₂, N(CH₃)₂, NO₂, CN, C₁₋₆-alkyl, C₂₋₆-alkenyl, phenyl or phenoxy.

The term "heteroaryl", taken alone or in combinations, designates aromatic heterocyclic radicals containing one or two five- and/or six-membered rings, at least one of them containing up to three heteroatoms selected from the group consisting of O, S and N and whereby the heteroaryl radicals or tautomeric forms thereof may be attached via any suitable atom. Said heteroaryl ring(s) are optionally substituted, e.g. as indicated above for "aryl".

The term "aryl-$C_{x-y}$-alkyl", as used herein, refers to an $C_{x-y}$-alkyl group as defined above, substituted by an aryl group, as defined above. Representative examples of aryl-$C_{x-y}$-alkyl moieties include, but are not limited to, benzyl, 1-phenylethyl, 2-phenylethyl, 3-phenylpropyl, 2-phenylpropyl and the like.

The term "heteroaryl-$C_{x-y}$-alkyl", as used herein, refers to an $C_{x-y}$-alkyl group as defined above, substituted by a heteroaryl group, as defined above. Examples of heteroaryl-$C_{x-y}$-alkyl groups include pyridin-3-ylmethyl, (1H-pyrrol-2-yl)ethyl and the like.

The term "aryl-cycloalkyl", as used herein, refers to a cycloalkyl group as defined above, substituted or annelated by an aryl group, as defined above. Examples of aryl-cycloalkyl moieties include, but are not limited to, phenylcyclopentyl, 2,3-dihydro-1H-indenyl, 1,2,3,4-tetrahydronaphthalenyl and the like.

The term "aryl-heterocycloalkyl", as used herein, refers to a heterocycloalkyl group as defined above, substituted or annelated by an aryl group, as defined above. Examples of aryl-heterocycloalkyl moieties include, but are not limited to, indolinyl, 1,2,3,4-tetrahydroquinolinyl and the like.

The term "heteroaryl-cycloalkyl", as used herein, refers to a cycloalkyl group as defined above, substituted or annelated by a heteroaryl group, as defined above. Examples of heteroaryl-cycloalkyl moieties include, but are not limited to, 5,6,7,8-tetrahydroquinolinyl and the like.

The term "heteroaryl-heterocycloalkyl", as used herein, refers to a heterocycloalkyl group as defined above, substituted or annelated by a heteroaryl group, as defined above. Examples of heteroaryl-heterocycloalkyl moieties include, but are not limited to, 4-(thiazol-2-yl)piperazinyl, 5,6,7,8-tetrahydro-1,6-naphthyridinyl and the like.

The terms "cycloalkyl-aryl", "heterocycloalkyl-aryl", "cycloalkyl-heteroaryl", and "heterocycloalkyl-heteroaryl", as used herein, are defined analog to the terms "aryl-cycloalkyl", "aryl-heterocycloalkyl", "heteroaryl-cycloalkyl" and "heteroaryl-heterocycloalkyl", as defined above, but connected in the opposite direction, e.g. instead of 4-(thiazol-2-yl)piperazinyl the term refers to 2-(piperazin-1-yl)thiazolyl and the like.

The terms "hydroxy", "alkoxy" and "aryloxy", taken alone or in combinations, refer to the groups of —OH, —O-alkyl and —O-aryl respectively, wherein an alkyl group or an aryl group is as defined above. The term "$C_{x-y}$-alkoxy" (x and y each being an integer) refers to an —O-alkyl group as defined before containing x to y carbon atoms attached to an oxygen atom. Representative examples of alkoxy groups include methoxy, ethoxy, n-propoxy, isopropoxy, n-butoxy, tert-butoxy and the like. Examples of aryloxy include e.g. phenoxy. For avoidance of doubt e.g. the term "hydroxy-$C_{1-8}$-alkyl" represents, among others, groups like e.g. hydroxymethyl, 1-hydroxypropyl, 2-hydroxypropyl or 3-hydroxy-2,3-dimethylbutyl.

The term "optionally substituted" is in general intended to mean that a group, such as, but not limited to $C_{x-y}$-alkyl, $C_{x-y}$-alkenyl, cycloalkyl, aryl, heteroaryl, heterocycloalkyl, $C_{x-y}$-alkoxy and aryloxy may be substituted with one or more substituents independently selected from amino (—$NH_2$), dimethylamino, nitro (—$NO_2$), halogen (F, Cl, Br, I), $CF_3$, cyano (—CN), hydroxy, methoxy, ethoxy, phenyloxy, benzyloxy, acetoxy, oxo (=O), carboxy, carboxamide, methyl, ethyl, phenyl, benzyl, sulfonic acid, sulfate, phosphonic acid, phosphate, or phosphonate.

In the context of this invention the term "naturally or non-naturally occurring α-amino acid" typically comprises any natural α-amino acid, such as the proteogenic amino acids (examples listed below), their natural or semi-synthetic derivatives and as well α-amino acids of purely synthetic origin. This term includes as well α-amino acid which are optionally substituted at the α-nitrogen of the amino acid such as, but not limited to, acetylation or alkylation, e.g. methylation, or benzylation.

The term "aliphatic α-amino acid" refers to α-amino acids with an aliphatic side-chain, such as, but not limited to, alanine, valine, leucine, isoleucine, n-octylglycine etc.

The term "aromatic α-amino acid" refer to α-amino acids with a side-chain comprising an aromatic or heteroaromatic group, such as, but not limited to, phenylalanine, tryptophan, histidine, O-methyl-tyrosine, 4-trifluormethyl-phenylalanine, 3,4-dichloro-homophenylalanine etc.

The term "cross-linking α-amino acid" refers to α-amino acids with a side-chain comprising a function able to cross-link to a second α-amino acid by a strong interaction such as a covalent bond or an electrostatic contact, such as, but not limited to, cysteine, homocysteine etc.

The term "alcoholic α-amino acid" refers to α-amino acids with a side-chain comprising an alcoholic or thioalcoholic group, i.e. a hydroxy or sulfhydryl function, such as, but not limited to, serine, threonine etc.

For the avoidance of doubt the term "single side-chain" in the context of an α-amino acid refers to a structure where the α-carbon of the amino acid is covalently connected to the (in-chain) groups of the carbonyl (C=O) and nitrogen (N) as well as to one hydrogen (H) and one variable side-chain, e.g. as defined above. A "single side-chain" may include as well a heterocyclic structure comprising the α-amino atom, such as but not limited to, proline, pipecolic acid etc.

For the avoidance of doubt the term "heteroatom" refers to any atom that is not carbon or hydrogen.

The descriptors L respectively D refer to the stereochemistry at the α-position of an α-amino acid and are used according the Fischer-Rosanoff convention of the IUPAC.

The peptidomimetics of the present invention can also be diastereomers (e.g. epimers) of compounds of formula (I) if no specific stereochemistry of the chiral center is determined in the description. These stereoisomers can be prepared by a modification of the process described below in which the appropriate isomers (e.g. epimers/enantiomers) of chiral starting materials are used. In case of ambiguous stereochemistry in the above description each single epimer is part of the present invention as well as a mixture of both.

A further embodiment of the present invention may also include compounds, which are identical to the compounds of formula (I), except that one or more atoms are replaced by an atom having an atomic mass number or mass different from the atomic mass number or mass usually found in nature, e.g. compounds enriched in $^2H$ (D), $^3H$, $^{11}C$, $^{14}C$, $^{127}I$ etc. These isotopic analogs and their pharmaceutical salts and formulations are considered useful agents in the therapy and/or diagnostic, for example, but not limited to, where a fine-tuning of in vivo half-life time could lead to an optimized dosage regimen.

A further particular embodiment of the invention relates to derivatives of general formula (I), wherein specifically $T^1$ is an D α-amino acid residue of one of the formulae $AA1^D$; $AA3^D$; $AA4^D$; $AA5^D$; or $AA8^D$;

$T^2$ is an L α-amino acid residue of one of the formulae

AA1; AA2; AA3; AA4; AA5; AA6; or AA8; and $P^7$ is an D α-amino acid residue of one of the formulae $AA1^D$; $AA4^D$; $AA5^D$; or $AA8^D$;

An alternative particular embodiment of the invention relates to derivatives of general formula (I), wherein specifically $T^1$ is an D α-amino acid residue of one of the formulae $AA4^D$; $AA5^D$; $AA6^D$; $AA7^D$; $AA8^D$; or $AA9^D$; and $T^2$ is an L α-amino acid residue of one of the formulae AA4; AA5; AA6; AA7; AA8; or AA9;

An other particular embodiment of the invention the elements of general formula (I) are defined as follows
$P^1$, $P^3$, $P^{13}$, and $P^{14}$ are independently
  Gly; Gly(tBu); Gly(cHex); Gly(cPr); Ala; Ala(tBu); Ala(cHex); Ala(cPr); Val; Nva;
  Leu; Ile; Nle; hLeu; OctG; Met; Ala(Ppz); Dab; Dab(Ac); Dab(cPr); Dab(iPr);
  Dab(MeSO$_2$); Dap; Dap(Ac); Dap(cPr); Dap(iPr); Dap(MeSO$_2$); Lys; Lys(Bz);
  Lys(Me); Lys(Nic); Lys((5R)OH); Lys(4Oxa); hLys; Orn; Orn(Ac); Orn(cPr);
  Orn(iPr); Arg; hArg; Asn; Asp; Gln; Glu; Cit; Met(O$_2$); Ser; hSer; Ser(Bn); Ser(Me);
  Thr; alloThr; Thr(Bn); Thr(Me); Bip; Bbta; 2Pal; 3Pal; 4Pal; h2Pal; h3Pal; h4Pal;
  Ala(2Furyl); Ala(3Furyl); Ala(1Im); Ala(2Im); hAla(1Im); hAla(2Im); Ala(Pyrazinyl);
  Ala(1Pyrazolyl); Ala(3Pyrazolyl); Ala(2Pyrimidin); Ala(4Pyrimidin);
  Ala(5Pyrimidin); Ala(2Quin); Ala(3Quin); Ala(4Quin); Phe; Phe(2Cl); Phe(3Cl);
  Phe(4Cl); phe(3,4Cl$_2$); Phe(2F); Phe(3F); Phe(4F); Phe(3CN); Phe(4CN);
  Phe(2CF$_3$); Phe(3CF$_3$); Phe(4CF$_3$); Phe(3,4(CF$_3$)$_2$); Phe(4COOMe); hPhe; Phg;
  1Nal; 2Nal; Nle(6OBn); Trp; Trp(7Aza); Trp(5Br); Trp(6Br); Trp(6CF$_3$); Trp(5Cl);
  Trp(6Cl); Trp(5,6Cl); Trp(5OH); hTrp; His; His(Me); His(Bn); hHis; Thi; Thz;
  Thz(5,5Me$_2$); Tic; Tic(7OH); Tyr; Tyr(Bn); Tyr(Me); Tyr(Ph); Tyr(4OHPh); hTyr; or
  Tza;
$P^2$, $P^5$ and $P^8$ are independently
  2Pal; 3Pal; 4Pal; h2Pal; h3Pal; h4Pal; Ala(2Furyl); Ala(3Furyl); Ala(1Im); Ala(2Im);
  hAla(1Im); hAla(2Im); Ala(Pyrazinyl); Ala(1Pyrazolyl); Ala(3Pyrazolyl);
  Ala(2Pyrimidin); Ala(4Pyrimidin); Ala(5Pyrimidin); Ala(2Quin); Ala(3Quin);
  Ala(4Quin); Phe; Phe(2Cl); Phe(3Cl); Phe(4Cl); Phe(3,4Cl$_2$); Phe(2F); Phe(3F);

Phe(4F); Phe(3CN); Phe(4CN); Phe(2CF$_3$); Phe(3CF$_3$); Phe(4CF$_3$); Phe(3,4(CF$_3$)$_2$);

Phe(4COOMe); hPhe; Phg; 1Nal; 2Nal; Nle(6OBn); Trp; Trp(7Aza); Trp(5Br);

Trp(6Br); Trp(6CF$_3$); Trp(5Cl); Trp(6Cl); Trp(5,6Cl); Trp (5OH); hTrp; His; His(Me);

His(Bn); hHis; Thi; Thz; Thz(5,5Me$_2$); Tic; Tic(7OH); Tyr; Tyr(Bn); Tyr(Me);

Tyr(Ph); Tyr(4OHPh); hTyr; or Tza;

P$^4$ and P$^{11}$ are independently
Cys; or hCys;

P$^6$ is Gly;

P$^7$ is $^D$Ala; $^D$Pro; $^D$Pro ((4R)OH); or $^D$Tic;

P$^9$ is Ser; hSer; Thr; alloThr;

P$^{10}$ is Gly; Gly(tBu); Gly(cHex); Gly(cPr); Ala; Ala(tBu); Ala(cHex); Ala(cPr); Val; Nva;

Leu; Ile; Nle; hLeu; or OctG; and

P$^{12}$ is Ser; hSer; Thr; alloThr; 2Pal; 3Pal; 4Pal; h2Pal; h3Pal; h4Pal; Ala(2Furyl);

Ala(3Furyl); Ala(1Im); Ala(2Im); hAla(1Im); hAla(2Im); Ala(Pyrazinyl);

Ala(1Pyrazolyl); Ala(3Pyrazolyl); Ala(2Pyrimidin); Ala (4Pyrimidin);

Ala(5Pyrimidin); Ala(2Quin); Ala(3Quin); Ala(4Quin); Phe; Phe(2Cl); Phe(3Cl);

Phe(4Cl); Phe(3,4Cl$_2$); Phe(2F); Phe(3F); Phe(4F); Phe (3CN); Phe(4CN);

Phe(2CF$_3$); Phe(3CF$_3$); Phe(4CF$_3$); Phe(3,4(CF$_3$)$_2$); Phe (4COOMe); hPhe; Phg;

1Nal; 2Nal; Trp; Trp(7Aza); Trp(5Br); Trp(6Br); Trp (6CF$_3$); Trp(5Cl); Trp(6Cl);

Trp(5,6Cl); Trp(5OH); hTrp; His; His(Me); His(Bn); hHis; Thi; Thz; Thz(5,5Me$_2$);

Tic; Tic(7OH); Tyr; Tyr(Bn); Tyr(Me); Tyr(Ph); Tyr (4OHPh); hTyr; or Tza;

or pharmaceutically acceptable salts thereof.

In a further particular embodiment of the invention the elements of general formula (I) are defined as follows T$^1$ is $^D$Ala; $^D$Lys; $^D$Pro; $^D$Pro ((4S)NH$_2$); $^D$Pro ((4S)OH); $^D$Pip; $^D$Thr; or $^D$Tic;

T$^2$ is Ala; Dab; Lys; Glu; Pro; Pro((4R)NH$_2$); Pro((4S)NH$_2$); Pro((4R)OH); Pro((4S)OH);

Pip; Tic; Oic; or Trp;

P$^1$, P$^3$, P$^{13}$, and P$^{14}$ are independently
Gly; Gly(tBu); Gly(cHex); Gly(cPr); Ala; Ala(tBu); Ala (cHex); Ala(cPr); Val; Nva;

Leu; Ile; Nle; hLeu; OctG; Met; Ala(Ppz); Dab; Dab(Ac); Dab(cPr); Dab(iPr);

Dab(MeSO$_2$); Dap; Dap(Ac); Dap(cPr); Dap(iPr); Dap (MeSO$_2$); Lys; Lys(Bz);

Lys(Me); Lys(Nic); Lys((5R)OH); Lys(4Oxa); hLys; Orn; Orn(Ac); Orn(cPr);

Orn(iPr); Arg; hArg; Asn; Asp; Gln; Glu; Cit; Met(O$_2$); Ser; hSer; Ser(Bn); Ser(Me);

Thr; alloThr; Thr(Bn); Thr(Me); Bip; Bbta; 2Pal; 3Pal; 4Pal; h2Pal; h3Pal; h4Pal;

Ala(2Furyl); Ala(3Furyl); Ala(1Im); Ala(2Im); hAla (1Im); hAla(2Im); Ala(Pyrazinyl);

Ala(1Pyrazolyl); Ala(3Pyrazolyl); Ala(2Pyrimidin); Ala (4Pyrimidin);

Ala(5Pyrimidin); Ala(2Quin); Ala(3Quin); Ala(4Quin); Phe; Phe(2Cl); Phe(3Cl);

Phe(4Cl); Phe(3,4Cl$_2$); Phe(2F); Phe(3F); Phe(4F); Phe (3CN); Phe(4CN);

Phe(2CF$_3$); Phe(3CF$_3$); Phe(4CF$_3$); Phe(3,4(CF$_3$)$_2$); Phe (4COOMe); hPhe; Phg;

1Nal; 2Nal; Nle(6OBn); Trp; Trp(7Aza); Trp(5Br); Trp (6Br); Trp(6CF$_3$); Trp(5Cl);

Trp(6Cl); Trp(5,6Cl); Trp(5OH); hTrp; His; His(Me); His(Bn); hHis; Thi; Thz;

Thz(5,5Me$_2$); Tic; Tic(7OH); Tyr; Tyr(Bn); Tyr(Me); Tyr (Ph); Tyr(4OHPh); hTyr; or Tza;

P$^2$, P$^5$ and P$^8$ are independently
2Pal; 3Pal; 4Pal; h2Pal; h3Pal; h4Pal; Ala(2Furyl); Ala (3Furyl); Ala(1Im); Ala(2Im);

hAla(1Im); hAla(2Im); Ala(Pyrazinyl); Ala(1Pyrazolyl); Ala(3Pyrazolyl);

Ala(2Pyrimidin); Ala(4Pyrimidin); Ala(5Pyrimidin); Ala (2Quin); Ala(3Quin);

Ala(4Quin); Phe; Phe(2Cl); Phe(3Cl); Phe(4Cl); Phe(3, 4Cl$_2$); Phe(2F); Phe(3F);

Phe(4F); Phe(3CN); Phe(4CN); Phe(2CF$_3$); Phe(3CF$_3$); Phe(4CF$_3$); Phe(3,4(CF$_3$)$_2$);

Phe(4COOMe); hPhe; Phg; 1Nal; 2Nal; Nle(6OBn); Trp; Trp(7Aza); Trp(5Br);

Trp(6Br); Trp(6CF$_3$); Trp(5Cl); Trp(6Cl); Trp(5,6Cl); Trp (5OH); hTrp; His; His(Me);

His(Bn); hHis; Thi; Thz; Thz(5,5Me$_2$); Tic; Tic(7OH); Tyr; Tyr(Bn); Tyr(Me);

Tyr(Ph); Tyr(4OHPh); hTyr; or Tza;

P$^4$ and P$^{11}$ are independently
Cys; or hCys;

P$^6$ is Gly;

P$^7$ is $^D$Ala; $^D$Pro; $^D$Pro ((4R)OH); or $^D$Tic;

P$^9$ is Ser; hSer; Thr; alloThr;

P$^{10}$ is Gly; Gly(tBu); Gly(cHex); Gly(cPr); Ala; Ala(tBu); Ala(cHex); Ala(cPr); Val; Nva;

Leu; Ile; Nle; hLeu; or OctG; and

P$^{12}$ is Ser; hSer; Thr; alloThr; 2Pal; 3Pal; 4Pal; h2Pal; h3Pal; h4Pal; Ala(2Furyl);

Ala(3Furyl); Ala(1Im); Ala(2Im); hAla(1Im); hAla(2Im); Ala(Pyrazinyl);

Ala(1Pyrazolyl); Ala(3Pyrazolyl); Ala(2Pyrimidin); Ala (4Pyrimidin);

Ala(5Pyrimidin); Ala(2Quin); Ala(3Quin); Ala(4Quin); Phe; Phe(2Cl); Phe(3Cl);

Phe(4Cl); Phe(3,4Cl$_2$); Phe(2F); Phe(3F); Phe(4F); Phe (3CN); Phe(4CN);

Phe(2CF$_3$); Phe(3CF$_3$); Phe(4CF$_3$); Phe(3,4(CF$_3$)$_2$); Phe (4COOMe); hPhe; Phg;

1Nal; 2Nal; Trp; Trp(7Aza); Trp(5Br); Trp(6Br); Trp (6CF$_3$); Trp(5Cl); Trp(6Cl);

Trp(5,6Cl); Trp(5OH); hTrp; His; His(Me); His(Bn); hHis; Thi; Thz; Thz(5,5Me$_2$);

Tic; Tic(7OH); Tyr; Tyr(Bn); Tyr(Me); Tyr(Ph); Tyr (4OHPh); hTyr; or Tza;

or pharmaceutically acceptable salts thereof.

In an even further particular embodiment of the invention the elements of general formula (I) are defined as follows T$^1$ is $^D$Ala; $^D$Lys; $^D$Pro; $^D$Pro ((4S)NH$_2$); $^D$Pro ((4S)OH); $^D$Pip; $^D$Thr; or $^D$Tic;

T$^2$ is Ala; Dab; Lys; Glu; Pro; Pro((4R)NH$_2$); Pro((4S)NH$_2$); Pro((4R)OH); Pro((4S)OH);

Pip; Tic; Oic; or Trp;

P$^1$ is Gly; Ala; Dab; Lys; Asp; Glu; Thr; His; or Tyr;

P$^2$ is His; or Tyr;

P$^3$ is Ala; Ile; Dab; Dap; Lys; Orn; Glu; Thr; or Trp;

P$^4$ is Cys;

P$^5$ is Phe; Phe(4CF$_3$); Tyr; Trp; Trp(5OH); or His;

P$^6$ is Gly;

P$^7$ is $^D$Ala; $^D$Pro; $^D$Pro ((4R)OH); or $^D$Tic;

P$^8$ is Phe(4CF$_3$); Trp;

$P^9$ is Thr;
$P^{10}$ is Ile; Leu; or Val;
$P^{11}$ is Cys;
$P^{12}$ is Thr; or Tyr;
$P^{13}$ is Ala; Dab; Asp; Glu; Gln; hSer; Thr; or Trp; and
$P^{14}$ is Gly; Ala; Dab; Lys; Glu; Gln; hSer; Thr; His; or Trp;
or pharmaceutically acceptable salts thereof.

Hereinafter follows a list of abbreviations, corresponding to generally adopted usual practice, of amino acids which, or the residues of which, are suitable for the purposes of the present invention and referred to in this document.

In spite of this specific determination of amino acids, it is noted that, for a person skilled in the art, it is obvious that derivatives of these amino acids, resembling alike structural and physico-chemical properties, lead to functional analogs with similar biological activity, and therefore still form part of the gist of this invention.

Ala L-Alanine
Arg L-Arginine
Asn L-Asparagine
Asp L-Aspartic acid
Cit L-Citrulline
Cys L-Cysteine
Gln L-Glutamine
Glu L-Glutamic acid
Gly Glycine
His L-Histidine
Ile L-Isoleucine
Leu L-Leucine
Lys L-Lysine
Met L-Methionine
Orn L-Ornithine
Phe L-Phenylalanine
Pro L-Proline
Ser L-Serine
Thr L-Threonine
Trp L-Tryptophan
Tyr L-Tyrosine
Val L-Valine
Ala(tBu) (S)-2-amino-4,4-dimethylpentanoic acid
Ala(cHex) (S)-2-amino-3-cyclohexylpropanoic acid
Ala(cPr) (S)-2-amino-3-cyclopropylpropanoic acid
Ala(2Furyl) (S)-2-amino-3-(furan-2-yl)propanoic acid
Ala(3Furyl) (S)-2-amino-3-(furan-3-yl)propanoic acid
Ala(1Im) (S)-2-amino-3-(1H-imidazol-1-yl)propanoic acid
Ala(2Im) (S)-2-amino-3-(1H-imidazol-2-yl)propanoic acid
Ala(Ppz) (S)-2-amino-3-(piperazin-1-yl)propanoic acid
Ala(cPr) (S)-2-amino-3-cyclopropylpropanoic acid
Ala(Pyrazinyl) (S)-2-amino-3-(pyrazin-2-yl)propanoic acid
Ala(1Pyrazolyl) (S)-2-amino-3-(1H-pyrazol-1-yl)propanoic acid
Ala(3Pyrazolyl) (S)-2-amino-3-(1H-pyrazol-3-yl)propanoic acid
Ala(2Pyrimidin) (S)-2-amino-3-(pyrimidin-2-yl)propanoic acid
Ala(4Pyrimidin) (S)-2-amino-3-(pyrimidin-4-yl)propanoic acid
Ala(5Pyrimidin) (S)-2-amino-3-(pyrimidin-5-yl)propanoic acid
Ala(2Quin) (S)-2-amino-3-(quinolin-2-yl)propanoic acid
Ala(3Quin) (S)-2-amino-3-(quinolin-3-yl)propanoic acid
Ala(4Quin) (S)-2-amino-3-(quinolin-4-yl)propanoic acid
Bbta (S)-2-amino-3-(1-benzothiophen-3-yl)propanoic acid
Bip (S)-2-amino-3-(4-biphenylyl)propanoic acid
Dab (S)-2,4-diaminobutanoic acid
Dab(Ac) (S)-4-acetamido-2-aminobutanoic acid
Dab(cPr) (S)-2-amino-4-(cyclopropylamino)butanoic acid
Dab(iPr) (S)-2-amino-4-(isopropylamino)butanoic acid
Dab(MeSO$_2$) (S)-2-amino-4-(methylsulfonamido)butanoic acid
Dap (S)-2,3-diaminopropanoic acid
Dap(Ac) (S)-3-acetamido-2-aminopropanoic acid
Dap(cPr) (S)-2-amino-3-(cyclopropylamino)propanoic acid
Dap(iPr) (S)-2-amino-3-(isopropylamino)propanoic acid
Dap(MeSO$_2$) (S)-2-amino-3-(methylsulfonamido)propanoic acid
Gly(tBu) (S)-2-amino-3,3-dimethylbutanoic acid
Gly(cHex) (S)-2-amino-2-cyclohexylacetic acid
Gly(cPr) (S)-2-amino-2-cyclopropylacetic acid
hAla(1Im) (S)-2-amino-3-(1H-imidazol-1-yl)-butanoic acid
hAla(2Im) (S)-2-amino-3-(1H-imidazol-2-yl)-butanoic acid
hArg (S)-2-amino-6-guanidinohexanoic acid
hCha (S)-2-amino-4-cyclohexylbutanoic acid
hCys (S)-2-amino-4-mercaptobutanoic acid
hHis (S)-2-amino-4-(1H-imidazol-5-yl)butanoic acid
hLeu (S)-2-amino-5-methylhexanoic acid
hLys (S)-2,7-diaminoheptanoic acid
h2Pal (S)-2-amino-4-(pyridin-2-yl)-butanoic acid
h3Pal (S)-2-amino-3-(pyridine-3-yl)-butanoic acid
h4Pal (S)-2-amino-3-(pyridine-4-yl)-butanoic acid
hPhe (S)-2-amino-4-phenylbutanoic acid
hSer (S)-2-amino-4-hydroxybutanoic acid
hTrp (S)-2-amino-4-(1H-indol-3-yl)butanoic acid
hTyr (S)-2-amino-4-(4-hydroxyphenyl)butanoic acid
His(Me) (S)-2-amino-3-(1-methyl-1H-imidazol-5-yl)propanoic acid
His(Bn) (S)-2-amino-3-(1-benzyl-1H-imidazol-5-yl)propanoic acid
Lys(Bz) (S)-2-amino-6-benzamidohexanoic acid
Lys(Me) (S)-2-amino-6-(methylamino)hexanoic acid
Lys(Nic) (S)-2-amino-6-(nicotinamido)hexanoic acid
Met(O$_2$) (S)-2-amino-4-(methylsulfonyl)butanoic acid
1Nal (S)-2-amino-3-naphthalen-1-ylpropanoic acid
2Nal (S)-2-amino-3-naphthalen-2-ylpropanoic acid
Nle (S)-2-amino-hexanoic acid
Nle(6OBn) (S)-2-amino-6-(benzyloxy)hexanoic acid
Nva (S)-2-aminopentanoic acid
OctG (S)-2-aminodecanoic acid
Oic (2S,3aS,7aS)-octahydro-1H-indole-2-carboxylic acid
Orn(Ac) (S)-5-acetamido-2-aminopentanoic acid
Orn(cPr) (S)-2-amino-5-(cyclopropylamino)pentanoic acid
Orn(iPr) (S)-2-amino-5-(isopropylamino)pentanoic acid
2Pal (S)-2-amino-3-(pyridine-2-yl) propionic acid
3Pal (S)-2-amino-3-(pyridine-3-yl)propionic acid
4Pal (S)-2-amino-3-(pyridine-4-yl)propionic acid
Phe(2Cl) (S)-2-amino-3-(2-chlorophenyl)propanoic acid
Phe(3Cl) (S)-2-amino-3-(3-chlorophenyl)propanoic acid
Phe(4Cl) (S)-2-amino-3-(4-chlorophenyl)propanoic acid
Phe(3,4Cl$_2$) (S)-2-amino-3-(3,4-dichlorophenyl)propanoic acid
Phe(2F) (S)-2-amino-3-(2-fluorophenyl)propanoic acid
Phe(3F) (S)-2-amino-3-(3-fluorophenyl)propanoic acid
Phe(4F) (S)-2-amino-3-(4-fluorophenyl)propanoic acid
Phe(3,4F$_2$) (S)-2-amino-3-(3,4-difluorophenyl)propanoic acid
Phe(3CN) (S)-2-amino-3-(3-cyanophenyl)propanoic acid
Phe(4CN) (S)-2-amino-3-(4-cyanophenyl)propanoic acid
Phe(2CF$_3$) (S)-2-amino-3-(2-(trifluoromethyl))propanoic acid
Phe(3CF$_3$) (S)-2-amino-3-(3-(trifluoromethyl))propanoic acid
Phe(4CF$_3$) (S)-2-amino-3-(4-(trifluoromethyl))propanoic acid Phe(3,4(CF₃)₂) (S)-2-amino-3-(3,4-bis(trifluoromethyl)) propanoic acid
Phe(4COOMe) (S)-2-amino-3-(4-(methoxycarbonyl)phenyl)propanoic acid
Phg (S)-2-amino-2-phenylacetic acid
Pip (S)-piperidine-2-carboxylic acid
Pro((4R)NH₂) (2S,4R)-4-aminopyrrolidine-2-carboxylic acid
Pro((4S)NH₂) (2S,4S)-4-aminopyrrolidine-2-carboxylic acid
Pro((4R)OH) (2S,4R)-4-hydroxypyrrolidine-2-carboxylic acid
Pro((4S)OH) (2S,4S)-4-hydroxypyrrolidine-2-carboxylic acid
Ser(Bn) (S)-2-amino-3-(benzyloxy)propanoic acid
Ser(Me) (S)-2-amino-3-methoxy-propanoic acid
Thi (S)-2-amino-3-(thiophen-2-yl)propanoic acid
alloThr (2S,3S)-2-amino-3-hydroxybutanoic acid
Thr(Bn) (2S,3R)-2-amino-3-(benzyloxy)butanoic acid
Thr(Me) (2S,3R)-2-amino-3-(methyloxy)butanoic acid
Thz (R)-thiazolidine-4-carboxylic acid
Thz(5,5Me₂) (R)-2,2-dimethylthiazolidine-4-carboxylic acid
Tic (S)-1,2,3,4-Tetrahydroisoquinoline-3-carboxylic acid
Tic(7OH) (S)-7-hydroxy-1,2,3,4-tetrahydroisoquinoline-3-carboxylic acid
Trp(7Aza) (S)-2-amino-3-(1H-pyrrolo[2,3-b]pyridin-3-yl)propanoic acid
Trp(5Br) (S)-2-amino-3-(5-bromo-1H-indol-3-yl)propanoic acid
Trp(6Br) (S)-2-amino-3-(6-bromo-1H-indol-3-yl)propanoic acid
Trp(6CF₃) (S)-2-amino-3-(6-(trifluoromethyl)-1H-indol-3-yl)propanoic acid
Trp(5Cl) (S)-2-amino-3-(5-chloro-1H-indol-3-yl)propanoic acid
Trp(6Cl) (S)-2-amino-3-(6-chloro-1H-indol-3-yl)propanoic acid
Trp(5,6Cl) (S)-2-amino-3-(5,6-dichloro-1H-indol-3-yl)propanoic acid
Trp(5OH) (S)-2-amino-3-(5-hydroxy-1H-indol-3-yl)propanoic acid
Tyr(Bn) (S)-2-amino-3-(4-(benzyloxy)phenyl)propanoic acid
Tyr(Me) (S)-2-amino-3-(4-methoxyphenyl)propanoic acid
Tyr(Ph) (S)-2-amino-3-(4-phenoxyphenyl)propanoic acid
Tyr(4OHPh) (S)-2-amino-3-[4-(4-hydroxyphenoxy)phenyl]propanoic acid
Tza (S)-2-amino-3-(thiazol-4-yl)propanoic acid The abbreviation of D-isomers, e.g. $^D$Lys corresponds to the epimer at the 2-position of the appropriate amino acid described above.

In a preferred embodiment of the invention the β-hairpin peptidomimetics of general formula (I) are selected from the group consisting of:

```
cyclo(-Glu-His-Lys-Cys-His-Gly-DPro-Trp-Thr-Ile-Cys-Tyr-Glu-Lys-DPro-Pro-)   (SEQ ID NO: 1);
cyclo(-Dab-His-Lys-Cys-His-Gly-DPro-Trp-Thr-Ile-Cys-Tyr-Glu-Lys-DPro-Glu-)   (SEQ ID NO: 2);
cyclo(-Tyr-His-Lys-Cys-His-Gly-DPro-Trp-Thr-Ile-Cys-Tyr-Glu-Lys-DPro-Glu-)   (SEQ ID NO: 3);
cyclo(-Tyr-His-Lys-Cys-His-Gly-DAla-Trp-Thr-Ile-Cys-Tyr-Glu-Lys-DPro-Glu-)   (SEQ ID NO: 4);
cyclo(-Tyr-His-Lys-Cys-His-Gly-DPro-Trp-Thr-Ile-Cys-Tyr-Glu-Lys-DLys-Glu-)   (SEQ ID NO: 5);
cyclo(-Tyr-His-Lys-Cys-His-Gly-DPro-Trp-Thr-Ile-Cys-Tyr-Glu-Lys-DAla-Glu-)   (SEQ ID NO: 6);
cyclo(-Tyr-His-Ala-Cys-Trp-Gly-DPro-Trp-Thr-Ile-Cys-Tyr-Gln-Lys-DPro-Glu-)   (SEQ ID NO: 7);
cyclo(-Tyr-His-Ala-Cys-His-Gly-DPro-Trp-Thr-Ile-Cys-Tyr-Gln-Lys-DPro-Trp-)   (SEQ ID NO: 8);
cyclo(-Tyr-His-Ala-Cys-Trp-Gly-DPro-Trp-Thr-Ile-Cys-Tyr-Gln-Lys-DPro-Ala-)   (SEQ ID NO: 9);
cyclo(-Tyr-His-Trp-Cys-Trp-Gly-DPro-Trp-Thr-Ile-Cys-Tyr-Gln-Lys-DPro-Pro-)   (SEQ ID NO: 10);
cyclo(-Tyr-His-Trp-Cys-His-Gly-DPro-Trp-Thr-Ile-Cys-Tyr-Gln-Lys-DPro-Pro-)   (SEQ ID NO: 11);
cyclo(-Tyr-His-Thr-Cys-His-Gly-DPro-Trp-Thr-Ile-Cys-Tyr-Gln-Lys-DPro-Pro-)   (SEQ ID NO: 12);
cyclo(-Tyr-His-Lys-Cys-Trp-Gly-DPro-Trp-Thr-Ile-Cys-Tyr-Gln-Lys-DPro-Pro-)   (SEQ ID NO: 13);
cyclo(-Tyr-His-Ile-Cys-His-Gly-DPro-Trp-Thr-Ile-Cys-Tyr-Gln-Lys-DPro-Pro-)   (SEQ ID NO: 14);
cyclo(-Tyr-His-Glu-Cys-His-Gly-DPro-Trp-Thr-Ile-Cys-Tyr-Gln-Lys-DPro-Pro-)   (SEQ ID NO: 15);
cyclo(-Tyr-His-Ala-Cys-His-Gly-DPro-Trp-Thr-Ile-Cys-Tyr-Trp-Lys-DPro-Pro-)   (SEQ ID NO: 16);
cyclo(-Tyr-His-Ala-Cys-Trp-Gly-DPro-Trp-Thr-Ile-Cys-Tyr-Glu-Lys-DPro-Pro-)   (SEQ ID NO: 17);
cyclo(-Tyr-His-Ala-Cys-Trp-Gly-DPro-Trp-Thr-Ile-Cys-Tyr-Trp-Lys-DPro-pro-)   (SEQ ID NO: 18);
cyclo(-Tyr-His-Ala-Cys-Trp-Gly-DPro-Trp-Thr-Ile-Cys-Tyr-Gln-Glu-DPro-Pro-)   (SEQ ID NO: 19);
cyclo(-Tyr-His-Ala-Cys-Trp-Gly-DPro-Trp-Thr-Ile-Cys-Tyr-Gln-Ala-DPro-Pro-)   (SEQ ID NO: 20);
cyclo(-Tyr-His-Ala-Cys-His-Gly-DPro-Trp-Thr-Ile-Cys-Tyr-Gln-Glu-DPro-Pro-)   (SEQ ID NO: 21);
cyclo(-Tyr-His-Ala-Cys-Phe-Gly-DPro-Trp-Thr-Ile-Cys-Tyr-Gln-Lys-DPro-Pro-)   (SEQ ID NO: 22);
cyclo(-Tyr-His-Ala-Cys-Tyr-Gly-DPro-Trp-Thr-Ile-Cys-Tyr-Gln-Lys-DPro-Pro-)   (SEQ ID NO: 23);
cyclo(-Glu-His-Ala-Cys-Trp-Gly-DPro-Trp-Thr-Ile-Cys-Tyr-Gln-Lys-DPro-Pro-)   (SEQ ID NO: 24);
cyclo(-Thr-His-Ala-Cys-Trp-Gly-DPro-Trp-Thr-Ile-Cys-Tyr-Gln-Lys-DPro-Pro-)   (SEQ ID NO: 25);
cyclo(-His-His-Ala-Cys-Trp-Gly-DPro-Trp-Thr-Ile-Cys-Tyr-Gln-Lys-DPro-Pro-)   (SEQ ID NO: 26);
cyclo(-Ala-His-Ala-Cys-Trp-Gly-DPro-Trp-Thr-Ile-Cys-Tyr-Gln-Lys-DPro-Pro-)   (SEQ ID NO: 27);
cyclo(-Lys-His-Ala-Cys-His-Gly-DPro-Trp-Thr-Ile-Cys-Tyr-Gln-Lys-DPro-Pro-)   (SEQ ID NO: 28);
cyclo(-His-Tyr-Ala-Cys-Trp-Gly-DPro-Trp-Thr-Ile-Cys-Tyr-Gln-Lys-DPro-Pro-)   (SEQ ID NO: 29);
cyclo(-Tyr-His-Ala-Cys-His-Gly-DPro-Trp-Thr-Ile-Cys-Tyr-Glu-Lys-DPro-Pro-)   (SEQ ID NO: 30);
cyclo(-Tyr-His-Ala-Cys-Trp-Gly-DPro-Trp-Thr-Ile-Cys-Tyr-Thr-Lys-DPro-Pro-)   (SEQ ID NO: 31);
cyclo(-Tyr-His-Ala-Cys-Trp-Gly-DPro-Trp-Thr-Ile-Cys-Tyr-Ala-Lys-DPro-Pro-)   (SEQ ID NO: 32);
cyclo(-Tyr-His-Ala-Cys-His-Gly-DPro-Trp-Thr-Ile-Cys-Tyr-Thr-Lys-DPro-Pro-)   (SEQ ID NO: 33);
cyclo(-Tyr-His-Ala-Cys-Trp-Gly-DPro-Trp-Thr-Ile-Cys-Thr-Gln-Lys-DPro-Pro-)   (SEQ ID NO: 34);
cyclo(-Tyr-His-Ala-Cys-Trp-Gly-DAla-Trp-Thr-Ile-Cys-Tyr-Gln-Lys-DPro-Pro-)   (SEQ ID NO: 35);
cyclo(-Tyr-His-Ala-Cys-His-Gly-DAla-Trp-Thr-Ile-Cys-Tyr-Gln-Lys-DPro-Pro-)   (SEQ ID NO: 36);
cyclo(-Tyr-His-Ala-Cys-Trp-Gly-DPro-Trp-Thr-Ile-Cys-Tyr-Gln-Lys-DLys-Pro-)   (SEQ ID NO: 37);
cyclo(-Tyr-His-Ala-Cys-His-Gly-DPro-Trp-Thr-Ile-Cys-Tyr-Gln-Lys-DThr-Pro-)   (SEQ ID NO: 38);
cyclo(-Tyr-His-Ala-Cys-Trp-Gly-DPro-Trp-Thr-Ile-Cys-Tyr-Gln-Lys-DAla-Pro-)   (SEQ ID NO: 39);
cyclo(-Tyr-His-Ala-Cys-Trp-Gly-DPro-Trp-Thr-Ile-Cys-Tyr-Gln-Lys-DPro-Pro-)   (SEQ ID NO: 40);
cyclo(-Tyr-His-Lys-Cys-His-Gly-DPro-Trp-Thr-Ile-Cys-Tyr-Glu-Lys-DAla-Pro-)   (SEQ ID NO: 41);
cyclo(-Tyr-His-Lys-Cys-Trp-Gly-DPro-Trp-Thr-Ile-Cys-Tyr-Glu-Lys-DAla-Pro-)   (SEQ ID NO: 42);
cyclo(-Tyr-His-Lys-Cys-Trp-Gly-DPro-Trp-Thr-Ile-Cys-Tyr-Glu-Lys-DLys-Pro-)   (SEQ ID NO: 43);
cyclo(-Tyr-His-Lys-Cys-His-Gly-DPro-Trp-Thr-Ile-Cys-Tyr-Glu-Lys-DLys-Pro-)   (SEQ ID NO: 44);
cyclo(-Tyr-His-Lys-Cys-His-Gly-DPro-Trp-Thr-Ile-Cys-Tyr-Glu-Lys-DTic-Pro-)   (SEQ ID NO: 45);
```

```
cyclo(-Tyr-His-Lys-Cys-His-Gly-DPro-Trp-Thr-Ile-Cys-Tyr-Glu-Lys-DPro((4S)      (SEQ ID NO: 46);
OH)-Pro-)
cyclo(-Tyr-His-Lys-Cys-His-Gly-DPro-Trp-Thr-Ile-Cys-Tyr-Glu-Lys-DPro((4S)      (SEQ ID NO: 47);
NH2)-Pro-)
cyclo(-Tyr-His-Lys-Cys-His-Gly-DPro-Trp-Thr-Ile-Cys-Tyr-Glu-Lys-DPip-Pro-)     (SEQ ID NO: 48);
cyclo(-Tyr-His-Lys-Cys-Tyr-Gly-DPro-Trp-Thr-Ile-Cys-Tyr-Glu-Lys-DPro-Pro-)     (SEQ ID NO: 49);
cyclo(-Tyr-His-Lys-Cys-Phe(4CF3)-Gly-DPro-Trp-Thr-Ile-Cys-Tyr-GIu-Lys-         (SEQ ID NO: 50);
DPro-Pro-)
cyclo(-Tyr-His-Lys-Cys-Trp-Gly-DPro-Trp-Thr-Ile-Cys-Tyr-Glu-Lys-DPro-Pro-)     (SEQ ID NO: 51);
cyclo(-Tyr-His-Lys-Cys-Trp-Gly-DPro-Trp-Thr-Ile-Cys-Tyr-Glu-Dab-DPro-Pro-)     (SEQ ID NO: 52);
cyclo(-Tyr-His-Lys-Cys-His-Gly-DPro-Trp-Thr-Ile-Cys-Tyr-Glu-Trp-DPro-Pro-)     (SEQ ID NO: 53);
cyclo(-Tyr-His-Lys-Cys-His-Gly-DPro-Trp-Thr-Ile-Cys-Tyr-Glu-Glu-DPro-Pro-)     (SEQ ID NO: 54);
cyclo(-Tyr-His-Lys-Cys-His-Gly-DPro-Trp-Thr-Ile-Cys-Tyr-Glu-His-DPro-Pro-)     (SEQ ID NO: 55);
cyclo(-Tyr-His-Lys-Cys-His-Gly-DPro-Trp-Thr-Ile-Cys-Tyr-Glu-Dab-DPro-Pro-)     (SEQ ID NO: 56);
cyclo(-Tyr-His-Lys-Cys-His-Gly-DPro-Trp-Thr-Ile-Cys-Tyr-Glu-Thr-DPro-Pro-)     (SEQ ID NO: 57);
cyclo(-Tyr-His-Lys-Cys-His-Gly-DPro-Trp-Thr-Ile-Cys-Tyr-Glu-Gly-DPro-Pro-)     (SEQ ID NO: 58);
cyclo(-Tyr-His-Lys-Cys-His-Gly-DPro-Trp-Thr-Ile-Cys-Tyr-Glu-Hse-DPro-Pro-)     (SEQ ID NO: 59);
cyclo(-Tyr-His-Lys-Cys-His-Gly-DPro-Trp-Thr-Ile-Cys-Tyr-Glu-Lys-DPro-Pro-)     (SEQ ID NO: 60);
cyclo(-Tyr-His-Orn-Cys-His-Gly-DPro-Trp-Thr-Ile-Cys-Tyr-Glu-Lys-DPro-Pro-)     (SEQ ID NO: 61);
cyclo(-Tyr-His-Lys-Cys-His-Gly-DTic-Trp-Thr-Ile-Cys-Tyr-Glu-Lys-DPro-Pro-)     (SEQ ID NO: 62);
cyclo(-Tyr-His-Lys-Cys-His-Gly-DPro-Trp-Thr-Ile-Cys-Tyr-Trp-Lys-DPro-Pro-)     (SEQ ID NO: 63);
cyclo(-Tyr-His-Lys-Cys-His-Gly-DPro-Trp-Thr-Ile-Cys-Tyr-Asp-Lys-DPro-Pro-)     (SEQ ID NO: 64);
cyclo(-Gly-His-Lys-Cys-His-Gly-DPro-Trp-Thr-Ile-Cys-Tyr-Glu-Lys-DPro-Pro-)     (SEQ ID NO: 65);
cyclo(-Asp-His-Lys-Cys-His-Gly-DPro-Trp-Thr-Ile-Cys-Tyr-Glu-Lys-DPro-Pro-)     (SEQ ID NO: 66);
cyclo(-Dab-His-Lys-Cys-His-Gly-DPro-Trp-Thr-Ile-Cys-Tyr-Glu-Lys-DPro-Pro-)     (SEQ ID NO: 67);
cyclo(-His-His-Lys-Cys-His-Gly-DPro-Trp-Thr-Ile-Cys-Tyr-Glu-Lys-DPro-Pro-)     (SEQ ID NO: 68);
cyclo(-Dab-His-Lys-Cys-Trp-Gly-DPro-Trp-Thr-Ile-Cys-Tyr-Glu-Lys-DPro-Pro-)     (SEQ ID NO: 69);
cyclo(-Tyr-His-Lys-Cys-Trp-Gly-DAla-Trp-Thr-Ile-Cys-Tyr-Glu-Lys-DPro-Pro-)     (SEQ ID NO: 70);
cyclo(-Tyr-His-Lys-Cys-His-Gly-DAla-Trp-Thr-Ile-Cys-Tyr-Glu-Lys-DPro-Pro-)     (SEQ ID NO: 71);
cyclo(-Tyr-His-Lys-Cys-Trp-Gly-DPro-Trp-Thr-Ile-Cys-Tyr-Dab-Lys-DPro-Pro-)     (SEQ ID NO: 72);
cyclo(-Tyr-His-Lys-Cys-His-Gly-DPro-Trp-Thr-Ile-Cys-Tyr-Hse-Lys-DPro-Pro-)     (SEQ ID NO: 73);
cyclo(-Tyr-His-Lys-Cys-His-Gly-DPro-Trp-Thr-Leu-Cys-Tyr-Glu-Lys-DPro-Pro-)     (SEQ ID NO: 74);
cyclo(-Tyr-His-Lys-Cys-His-Gly-DPro-Trp-Thr-Val-Cys-Tyr-Glu-Lys-DPro-Pro-)     (SEQ ID NO: 75);
cyclo(-Tyr-His-Lys-Cys-His-Gly-DPro-Phe(4CF3)-Thr-IIe-Cys-Tyr-Glu-Lys-         (SEQ ID NO: 76);
DPro-Pro-)
cyclo(-Tyr-His-Ile-Cys-His-Gly-DPro-Trp-Thr-Ile-Cys-Tyr-Glu-Lys-DPro-Pro-)     (SEQ ID NO: 77);
cyclo(-Tyr-His-Dap-Cys-His-Gly-DPro-Trp-Thr-Ile-Cys-Tyr-Glu-Lys-DPro-Pro-)     (SEQ ID NO: 78);
cyclo(-Tyr-His-Dab-Cys-Trp-Gly-DPro-Trp-Thr-Ile-Cys-Tyr-Glu-Lys-DPro-Pro-)     (SEQ ID NO: 79);
cyclo(-Tyr-His-Dab-Cys-His-Gly-DPro-Trp-Thr-Ile-Cys-Tyr-Glu-Lys-DPro-Pro-)     (SEQ ID NO: 80);
cyclo(-Tyr-His-Lys-Cys-His-Gly-DPro-Trp-Thr-IIe-Cys-Tyr-GIu-Lys-DPro-Pro       (SEQ ID NO: 81);
((4S)NH2)-)
cyclo(-Tyr-His-Lys-Cys-His-Gly-DPro-Trp-Thr-IIe-Cys-Tyr-Glu-Lys-DPro-Pro       (SEQ ID NO: 82);
((4R)OH)-)
cyclo(-Tyr-His-Lys-Cys-His-Gly-DPro-Trp-Thr-IIe-Cys-Tyr-Glu-Lys-DPro-Pro       (SEQ ID NO: 83);
((4R)NH2)-)
cyclo(-Tyr-His-Lys-Cys-His-Gly-DPro((4R)OH)-Trp-Thr-Ile-Cys-Tyr-Glu-Lys-       (SEQ ID NO: 84);
DPro-Pro-)
cyclo(-Tyr-His-Lys-Cys-Trp(5OH)-Gly-DPro-Trp-Thr-IIe-Cys-Tyr-Glu-Lys-          (SEQ ID NO: 85);
DPro-Pro-)
cyclo(-Tyr-His-Lys-Cys-His-Gly-DPro-Trp-Thr-Ile-Cys-Tyr-Glu-Lys-DPro-Lys-)     (SEQ ID NO: 86);
cyclo(-Tyr-His-Lys-Cys-Trp-Gly-DPro-Trp-Thr-Ile-Cys-Tyr-Glu-Lys-DPro-Lys-)     (SEQ ID NO: 87);
cyclo(-Tyr-His-Ala-Cys-Trp-Gly-DPro-Trp-Thr-Ile-Cys-Tyr-Gln-Lys-DPro-Lys-)     (SEQ ID NO: 88);
cyclo(-Tyr-His-Lys-Cys-His-Gly-DPro-Trp-Thr-Ile-Cys-Tyr-Glu-Lys-DPro-Dab-)     (SEQ ID NO: 89);
cyclo(-Tyr-His-Lys-Cys-His-Gly-DPro-Trp-Thr-Ile-Cys-Tyr-Glu-Lys-DPro-Pip-)     (SEQ ID NO: 90);
cyclo(-Tyr-His-Lys-Cys-His-Gly-DPro-Trp-Thr-Ile-Cys-Tyr-Glu-Lys-DPro-Tic-)     (SEQ ID NO: 91);
cyclo(-Tyr-His-Lys-Cys-His-Gly-DPro-Trp-Thr-Ile-Cys-Tyr-Glu-Lys-DPro-Oic-)     (SEQ ID NO: 92);
``` or pharmaceutically acceptable salts thereof.

In a particularly preferred embodiment of the invention the β-hairpin peptidomimetics of general formula (I) are selected from the group consisting of:

```
cyclo(-Tyr-His-Ile-Cys-His-Gly-DPro-Trp-Thr-Ile-Cys-Tyr-Gln-Lys-DPro-Pro-);

cyclo(-Tyr-His-Lys-Cys-His-Gly-DPro-Trp-Thr-Ile-Cys-Tyr-Glu-Lys-DPro((4S)OH)-
Pro-);

cyclo(-Tyr-His-Lys-Cys-His-Gly-DPro-Trp-Thr-Ile-Cys-Tyr-Glu-Lys-DPro((4S)NH2)-
Pro-);

cyclo(-Tyr-His-Lys-Cys-His-Gly-DPro-Trp-Thr-Ile-Cys-Tyr-Glu-Lys-DPip-Pro-);

cyclo(-Tyr-His-Lys-Cys-Tyr-Gly-DPro-Trp-Thr-Ile-Cys-Tyr-Glu-Lys-DPro-Pro-);

cyclo(-Tyr-His-Lys-Cys-Trp-Gly-DPro-Trp-Thr-Ile-Cys-Tyr-Glu-Lys-DPro-Pro-);

cyclo(-Tyr-His-Lys-Cys-His-Gly-DPro-Trp-Thr-Ile-Cys-Tyr-Glu-Hse-DPro-Pro-);
```

```
cyclo(-Tyr-His-Lys-Cys-His-Gly-DPro-Trp-Thr-Ile-Cys-Tyr-Glu-Lys-DPro-Pro-);

cyclo(-Tyr-His-Lys-Cys-His-Gly-DTic-Trp-Thr-Ile-Cys-Tyr-Glu-Lys-DPro-Pro-);

cyclo(-Tyr-His-Lys-Cys-His-Gly-DPro-Trp-Thr-Ile-Cys-Tyr-Trp-Lys-DPro-Pro-);

cyclo(-Tyr-His-Lys-Cys-His-Gly-DPro-Trp-Thr-Ile-Cys-Tyr-Asp-Lys-DPro-Pro-);

cyclo(-Tyr-His-Ile-Cys-His-Gly-DPro-Trp-Thr-Ile-Cys-Tyr-Glu-Lys-DPro-Pro-);

cyclo(-Tyr-His-Lys-Cys-Trp(5OH)-Gly-DPro-Trp-Thr-Ile-Cys-Tyr-Glu-Lys-DPro-Pro-);

cyclo(-Tyr-His-Lys-Cys-Trp-Gly-DPro-Trp-Thr-Ile-Cys-Tyr-Glu-Lys-DPro-Lys-);
``` or pharmaceutically acceptable salts thereof.

A further embodiment of the invention relates to the preparation of the present β-hairpin peptidomimetics by a process which comprises the steps of (a) coupling an appropriately functionalized solid support with an appropriately N-protected derivative of that amino acid which in the desired end-product is in position $T^1$ or $T^2$ or $P^1$ to $P^{14}$ as defined above; any functional group which may be present in said N-protected amino acid derivative being likewise appropriately protected;

(b) removing the N-protecting group from the product obtained in step (a);

(c) coupling the product thus obtained with an appropriately N-protected derivative of that amino acid which in the desired end-product is in the position of the next element (T or P), following counterclockwise or clockwise the sequence according to general formula (I) in —COOH to —NH$_2$ orientation; any functional group which may be present in said N-protected amino acid derivative being likewise appropriately protected;

(d) removing the N-protecting group from the product thus obtained;

(e) repeating steps (c) and (d) until all amino acid residues have been introduced;

(f) if desired, selectively deprotecting one or several protected functional group(s) present in the molecule and chemically transforming the reactive group(s) thus liberated;

(g) detaching the product thus obtained from the solid support;

(h) cyclizing the product cleaved from the solid support;

(i) removing any protecting groups present on functional groups of any members of the chain of amino acid residues and, if desired, any protecting group(s) which may in addition be present in the molecule;

(j) if desired, forming a disulfide bridge between sulfhydryl containing residues at $P^4$ and $P^{11}$;

(k) if desired, implementing additional chemical transformations of one or more reactive group(s) present in the molecule; and (l) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt.

The process of the invention can advantageously be carried out as parallel array synthesis to yield libraries of template-fixed β-hairpin peptidomimetics of the above general formula (I). Such parallel synthesis allows one to obtain arrays of numerous (normally 24 to 192, typically 96) compounds of general formula (I) in high yields and defined purities, minimizing the formation of dimeric and polymeric by-products. The proper choice of the functionalized solid support (i.e. solid support plus linker molecule), templates and site of cyclization play thereby key roles.

The functionalized solid support is conveniently derived from polystyrene ("PS") crosslinked with, preferably 1-5%, divinylbenzene; polystyrene coated with polyethyleneglycol spacers (Tentagel®); and polyacrylamide resins (see also Obrecht, D.; Villalgordo, J.-M, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention two types of linkers are used:

Type 1 linkers are designed to release the amide group under acidic conditions (Rink H, *Tetrahedron Lett*. 1987, 28, 3783-3790). Linkers of this kind form amides of the carboxyl group of the amino acids; examples of resins functionalized by such linker structures include 4-[(((2,4-dimethoxyphenyl)Fmoc-aminomethyl)phenoxyacetamido)-aminomethyl] PS resin, 4-[(((2,4-dimethoxyphenyl)Fmoc-aminomethyl)phenoxyacetamido)aminomethyl]-4-methylbenzydrylamine PS resin (Rink amide MBHA PS Resin), and 4-[(((2,4-dimethoxyphenyl)Fmoc-aminomethyl)phenoxyacetamido)aminomethyl]-benzhydrylamine PS-resin (Rink amide BHA PS resin). Preferably, the support is derived from polystyrene crosslinked with, most preferably 1-5%, divinylbenzene and functionalized by means of the 4-(((2,4-dimethoxyphenyl)Fmoc-aminomethyl)phenoxyacetamido) linker.

Type 2 linkers are designed to eventually release the carboxyl group under acidic conditions. Linkers of this kind form acid-labile esters with the carboxyl group of the amino acids, usually acid-labile benzyl, benzhydryl and trityl esters; examples of such linker structures include 2-methoxy-4-hydroxymethylphenoxy (Sasrin® linker), 4-(2,4-dimethoxyphenyl-hydroxymethyl)-phenoxy (Rink linker), 4-(4-hydroxymethyl-3-meth-oxyphenoxy)butyric acid (HMPB linker), trityl and 2-chlorotrityl. Preferably, the support is derived from polystyrene crosslinked with, most preferably 1-5%, divinylbenzene and functionalized by means of the 2-chlorotrityl linker.

When carried out as parallel array syntheses the process of the invention can be advantageously carried out as described herein below but it will be immediately apparent to those skilled in the art how these procedures will have to be modified in case it is desired to synthesize one single compound of the above formula (I).

A number of reaction vessels (normally 24 to 192, typically 96) equal to the total number of compounds to be synthesized by the parallel method are loaded with 25 to 1000 mg, preferably 100 mg, of the appropriate functionalized solid support which is preferably derived from polystyrene cross-linked with 1 to 3% of divinylbenzene, or from Tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (Fields, G. B., Fields, C. G., *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin® linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the processes of the invention include the super acid labile 4-(2,4-dimethoxyphenyl-hydroxymethyl)-phenoxy linker (Rink linker, Rink, H. *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxy-phenoxy)butyric acid-derived linker (HMPB-linker, Flörsheimer & Riniker, *Peptides* 1991, 1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoro-ethanol/DCM (1:2: 7) for about 30 min.

Suitable protecting groups for amino acids and, respectively, for their residues are, for example, for the amino group (as is present e.g. also in the side-chain of lysine)
Cbz benzyloxycarbonyl
Boc tert.-butyloxycarbonyl
Fmoc 9-fluorenylmethoxycarbonyl
Alloc allyloxycarbonyl
Teoc trimethylsilylethoxycarbonyl
Tcc trichloroethoxycarbonyl
Nps o-nitrophenylsulfonyl
Trt triphenymethyl or trityl
for the carboxyl group (as is present e.g. also in the side-chain of aspartic and glutamic acid) by conversion into esters with the alcohol components
tBu tert.-butyl
Bn benzyl
Me methyl
Ph phenyl
allyl
Tse trimethylsilylethyl
Tce trichloroethyl
for the guanidino group (as is present e.g. in the side-chain of arginine)
Pmc 2,2,5,7,8-pentamethylchroman-6-sulfonyl
Ts tosyl (i.e. p-toluenesulfonyl)
Cbz benzyloxycarbonyl
Pbf 2,2,4,6,7-pentamethyldihydrobenzofuran-5-sulfonyl
for the hydroxy group (as is present e.g. in the side-chain of threonine and serine)
tBu tert.-butyl
Bn benzyl
Trt trityl
and for the mercapto group (as is present e.g. in the side-chain of cysteine)
Acm acetamidomethyl
tBu tert.-butyl
Bn benzyl
Trt trityl
Mtr 4-methoxytrityl.

The 9-fluorenylmethoxycarbonyl-(Fmoc)-protected amino acid derivatives are preferably used as the building blocks for the construction of the template-fixed β-hairpin loop mimetics of formula (I). For the deprotection, i.e. cleaving off of the Fmoc group, 20% piperidine in DMF or 2% DBU/2% piperidine in DMF can be used.

The quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used, if required, to drive the reaction to completion in a reasonable time. The reaction tubes, in combination with the holder block and the manifold, are reinserted into the reservoir block and the apparatus is fastened together. Gas flow through the manifold is initiated to provide a controlled environment, for example, nitrogen, argon, air and the like. The gas flow may also be heated or chilled prior to flow through the manifold. Heating or cooling of the reaction wells is achieved by heating the reaction block and, respectively, cooling it externally with isopropanol/dry ice and the like to bring about the desired synthetic reactions. Agitation is achieved by shaking or magnetic stirring (within the reaction tube). The preferred workstations (without, however, being limited thereto) are Labsource's Combi-chem station and MultiSyn Tech's-Syro synthesizer.

Amide bond formation requires the activation of the α-carboxyl group for the acylation step. If this activation is being carried out by means of the commonly used carbodiimides, such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea and diisopropylurea is insoluble and, respectively, soluble in the solvents generally used. In a variation of the carbodiimide method 1-hydroxybenzotriazole (HOBt, König & Geiger, *Chem. Ber* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethylamino)-phosphonium hexafluorophosphate (BOP, Castro et al., *Tetrahedron Lett.* 1975, 14, 1219-1222; Synthesis, 1976, 751-752), or benzotriazol-1-yl-oxy-tris-pyrrolidino-phosphonium hexafluorophosphate (Py-BOP, Coste et al., *Tetrahedron Lett.* 1990, 31, 205-208), or 2-(1H-benzotriazol-1-yl-)1,1,3,3-tetramethyluronium tetrafluoroborate (TBTU), or hexafluorophosphate (HBTU, Knorr et al., *Tetrahedron Lett.* 1989, 30, 1927-1930); these phosphonium and uronium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) have also been used as coupling reagents.

Due to the fact that near-quantitative coupling reactions are essential, it is desirable to have experimental evidence for completion of the reactions. The ninhydrin test (Kaiser et al., *Anal. Biochemistry* 1970, 34, 595), where a positive colorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 35-42).

The resin-bound intermediate within each reaction tube is washed free of excess of retained reagents, of solvents, and of by-products by repetitive exposure to pure solvent(s).

Washing procedures are repeated up to about 30 times (preferably about 5 times), monitoring the efficiency of reagent, solvent, and by-product removal by methods such as TLC, GC, LC-MS or inspection of the washings.

The above described procedure of reacting the resin-bound compound with reagents within the reaction wells followed by removal of excess reagents, by-products, and solvents is repeated with each successive transformation until the final resin-bound fully protected linear peptide has been obtained.

Before this fully protected linear peptide is detached from the solid support, it is possible, if desired, to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for such an amino protecting group which can be selectively removed, e.g. by means of Pd° and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced.

After detachment of the fully protected linear peptide from the solid support the individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier as activators for the amide bond formation can be used for the cyclization. The duration of the cyclization is about 6-48 hours, preferably about 16 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Finally, the fully protected peptide derivative is treated with 95% TFA, 2.5% $H_2O$, 2.5% TIS, or 87.5% TFA, 2.5% DODT, 5% thioanisol, 5% $H_2O$ or another combination of scavengers for effecting the cleavage of protecting groups. The cleavage reaction time is commonly 30 minutes to 12 hours, preferably about 2.5 hours. The volatiles are evaporated to dryness and the crude peptide is dissolved in 20% AcOH in water and extracted with isopropyl ether or other solvents which are suitable therefore. The aqueous layer is collected and evaporated to dryness, and the fully deprotected cyclic peptide is obtained. Alternatively the deprotected cyclic peptide can be precipitated and washed using cold $Et_2O$.

For some compounds of the present invention according general formula (I) additional synthetic steps are required. These transformations can be applied either on a partially deprotected cyclic or linear peptide, attached or already released from the solid support or on the final deprotected molecule.

For instance, the formation of the disulfide bridge can be carried out, as described herein below, by stirring the crude fully deprotected and cyclized peptide for 24 h in water containing DMSO up to 15% by volume, buffered with $NH_4HCO_3$ to pH 5-6, or buffered with ammonium acetate to pH 7-8, or adjusted with ammonium hydroxide to pH 8. Alternatively, a solution of 10 equivalents of iodine solution is applied in DMF or in a mixture of $CH_2Cl_2$/MeOH for 1.5 h which is repeated for another 3 h with a fresh iodine solution. Following evaporation to dryness, the fully deprotected and disulfide bridged cyclic peptide derivative of formula (I) is obtained as end-product.

Depending on its purity, this peptide derivative can be used directly for biological assays, or it has to be further purified, for example by preparative HPLC.

As mentioned earlier, it is thereafter possible, if desired, to convert a fully deprotected product of formula (I) thus obtained into a pharmaceutically acceptable salt or to convert a pharmaceutically acceptable, or unacceptable, salt thus obtained into the corresponding free compound of formula (I) or into a different, pharmaceutically acceptable, salt. Any of these operations can be carried out by methods well known in the art.

In general the building blocks for the peptidomimetics of the present invention can be synthesized according to the literature methods (example described below), which are known to a person skilled in the art or are commercially available. A few additional new syntheses were carried out for this invention and are described in the examples. All other corresponding amino acids have been described either as unprotected or as Boc- or Fmoc-protected racemates, (D)- or (L)-isomers. It will be appreciated that unprotected amino acid building blocks can be easily transformed into the corresponding Fmoc-protected amino acid building blocks required for the present invention by standard protecting group manipulations. Reviews describing general methods for the synthesis of α-amino acids include: R. Duthaler, *Tetrahedron* (Report) 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989. An especially useful method for the synthesis of optically active α-amino acids relevant for this invention includes kinetic resolution using hydrolytic enzymes (M. A. Verhovskaya, I. A. Yamskov, *Russian Chem. Rev.* 1991, 60, 1163-1179; R.

M. Williams, "Synthesis of optically active α-amino acids", *Tetrahedron Organic Chemistry Series*, Vol. 7, J. E. Baldwin, P. D. Magnus (Eds.), Pergamon Press., Oxford 1989, Chapter 7, p. 257-279). Kinetic resolution using hydrolytic enzymes involves hydrolysis of amides and nitriles by aminopeptidases or nitrilases, cleavage of N-acyl groups by acylases, and ester hydrolysis by lipases or proteases. It is well documented that certain enzymes will lead specifically to pure (L)-enantiomers whereas others yield the corresponding (D)-enantiomers (e.g.: R. Duthaler, *Tetrahedron Report* 1994, 349, 1540-1650; R. M. Williams, "Synthesis of optically active α-amino acids", *Tetrahedron Organic Chemistry Series*, Vol. 7, J. E. Baldwin, P. D. Magnus (Eds.), Pergamon Press., Oxford 1989).

The β-hairpin peptidomimetics of the invention can be used in a wide range of applications in order to inhibit FPR1 receptor activity leading to the desired therapeutic effect in man or, due to their similar etiology, in other mammals. Especially they can be used as agents for treating and/or preventing diseases or conditions in the disease areas of inflammatory diseases, allergic conditions, immunological disorders, neuroinflammation, neurological disorders, obstructive airway diseases, infectious diseases, ischemic reperfusion injuries and cancer. Specific disease conditions falling under the areas described above are e.g. acute and chronic lung inflammation, COPD, asthma, emphysema, inflammation of the gastrointestinal tract, inflammatory bowel disease (IBD), Crohn's disease, acute skin inflammation, atopic dermatitis, eczema, psoriasis, rosacea, acne, neutrophilic dermatosis, neutrophil disorder, eosinophil disorder, monocytemacrophage associated diseases, Jobs syndrome, Chédiak-Higashi syndrome, chronic granulomatous disease, leukocyte adhesion deficiency, cystic fibrosis, peritonitis, periodontitis, sepsis, pneumonia, bacterial infection, and proliferative disorders such as e.g. cancer.

For use as active ingredients of a medicament the β-hairpin peptidomimetics of the invention can be administered singly, as mixtures of several β-hairpin peptidomimetics of the invention or in combination with other pharmaceutically active agents. The active ingredient(s) consisting of, or containing the β-hairpin peptidomimetics of the invention may be administered per se or applied as a pharmaceutical preparation, e.g. an appropriate formulation together with carriers, diluents or excipients well known in the art.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solution may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds of the invention can be readily formulated by combining the active β-hairpin peptidomimetics with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion of a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxy-methylcellulose, and/or polyvinylpyrrolidone (PVP); granulating agents; and binding agents. If desired, disintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the β-hairpin peptidomimetics of the invention are conveniently delivered in form of an aerosol spray from pressurized packs or a nebulizer, with the use of a suitable propellant, e.g. dichlorodifluoromethane, trichloro-fluoromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as solutions for enema or suppositories together with appropriate suppository bases such as cocoa butter or other glycerides.

In addition to the formulations described previously, the β-hairpin peptidomimetics of the invention may also be formulated as depot preparations. Such long acting formulations may be administered by implantation (e.g. subcutaneously or intramuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide also may be employed. Additionally, the β-hairpin peptidomimetics of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 3 years. Depending on the chemical nature and the biological stability of the therapeutic agent, additional strategies for protein stabilization may be employed.

As the β-hairpin peptidomimetics of the invention may contain charged residues, they may be included in any of the above-described formulations as such or as pharmaceutically acceptable salts. Pharmaceutically acceptable salts tend to be more soluble in aqueous and other protic solvents than are the corresponding free base forms.

In addition, the compounds of the present invention and their pharmaceutical acceptable salts may be used per se or in any appropriate formulation in morphological different solid state forms, which may or may not contain different amounts of solvent, e.g. hydrate remaining from the crystallization process.

The β-hairpin peptidomimetics of the invention, or compositions thereof, will generally be used in an amount effective to achieve the intended purpose. It is to be understood that the amount used will depend on a particular application.

For the use of treating or preventing diseases or disorders with an etiology comprising, or associated with, an increased activity of FPR1 and/or its endo- or exogenous ligands (e.g. N-formylmethionine etc.), the β-hairpin peptidomimetics of the invention or compositions thereof, are administered or applied in a therapeutically effective amount. Determination of a therapeutically effective amount is well within the capacities of those skilled in the art, especially in view of the detailed disclosure provided herein.

The effective dosage of the active ingredients employed may vary depending on the particular compound or pharmaceutical preparation employed, the mode of administration and the severity and type of the condition treated. Thus, the dosage regimen is selected in accordance with factors including the route of administration and the clearance pathway, e.g. the renal and hepatic function of the patient. A physician, clinician or veterinarian skilled in the art can readily determine and prescribe the amount of the single active ingredients required to prevent, ameliorate or arrest the progress of the condition or disease. Optimal precision in achieving concentration of active ingredients without toxicity requires a regimen based on the kinetics of the active ingredients' availability to the target sites. This involves a consideration of the distribution, equilibrium, and elimination of the active ingredients.

In cases of local administration or selective uptake, the effective local concentration of the β-hairpin peptidomimetics of the invention may not be related to plasma concentration. One having the skills in the art will be able to optimize therapeutically effective local dosages without undue experimentation.

The invention will now be further described in the Examples below, which are intended as an illustration only and not to be construed as limiting the scope of the invention in any way.

The following abbreviations are used:
Ac Acetyl;
BSA Bovine serum albumin;
Boc tert-Butyloxycarbonyl;
DCHA Dicyclohexylamine;
DEAD Diethyl azodicarboxylate;
DIPEA Diisopropylethylamine;
DMEM Dulbecco's Modified Eagle's Medium;
DODT 3,6-dioxa-1,8-octanedithiol;
FCS Fetal Calf Serum;
Fmoc Fluorenylmethyloxycarbonyl;
HATU O-(7-Aza-benzotriazole-1-yl)-N,N,N',N'-tetramethyluronoium hexafluorophosphate;
HBSS Hank's Buffered Salt Solution;
HBTU O-(Benzotriazol-1-yl)-N,N,N',N'-tetramethyluronium hexafluorophosphate;
HCTU O-(6-Chlorobenzotriazol-1-yl)-N,N,N',N'-tetramethyluronium hexafluorophosphate;
Hepes 4-(2-hydroxyethyl)-1-piperazineethanesulfonic acid;
HOAt 1-Hydroxy-7-azabenzotriazole;
IMDM Iscove's Modified Dulbecco's Media;
PyBop® (Benzotriazol-1-yloxy)tripyrrolidinophosphonium hexafluorophosphate;
TIS Triisopropylsilane;
TPP Triphenylphosphine;
RPMI Roswell Park Memorial Institute medium;
rt Room temperature.

EXAMPLES

1. Peptide Synthesis 1.1 General Synthetic Procedures

A general method for the synthesis of the peptidomimetics of the present invention is exemplified in the following. This is to demonstrate the principal concept and does not limit or restrict the present invention in any way. A person skilled in the art is easily able to modify these procedures, especially, but not limited to, choosing a different starting position within the ring system, to still achieve the preparation of the claimed cyclic peptidomimetic compounds of the present invention.

Coupling of the First Protected Amino Acid Residue to the Resin

In a dried flask, 2-chlorotritylchloride resin (polystyrene, 1% crosslinked; loading: 1.4 mmol/g) was swollen in dry $CH_2Cl_2$ for 30 min (7 ml $CH_2Cl_2$ per g resin). A solution of 0.8 eq of the Fmoc-protected amino acid and 6 eq of DIPEA in dry $CH_2Cl_2$DMF (4/1) (10 ml per g resin) was added. After shaking for 2-4 h at rt the resin was filtered off and washed successively with $CH_2Cl_2$, DMF, $CH_2Cl_2$, DMF and $CH_2Cl_2$. Then a solution of dry $CH_2Cl_2$/MeOH/DIPEA (17:2:1) was added (10 ml per g resin). After shaking for 3×30 min the resin was filtered off in a pre-weighed sinter funnel and washed successively with $CH_2Cl_2$, DMF, $CH_2Cl_2$, MeOH, $CH_2Cl_2$, MeOH, $CH_2Cl_2$ (2×) and $Et_2O$ (2×). The resin was dried under high vacuum overnight. The final mass of resin was calculated before the qualitative control.

The following preloaded resins were prepared: Fmoc-Ala-2-chlorotrityl resin, Fmoc-Cys-2-chlorotrityl resin, Fmoc-Dab-2-chlorotrityl resin, Fmoc-Gly-2-chlorotrityl resin, Fmoc-Lys-2-chlorotrityl resin, Fmoc-Oic-2-chlorotrityl resin, Fmoc-Pip-2-chlorotrityl resin, Fmoc-Pro-2-chlorotrityl resin, Fmoc-$^D$Pro-2-chlorotrityl resin, Fmoc-Tic-2-chlorotrityl resin, Fmoc-Trp-2-chlorotrityl resin.

Synthesis of the Fully Protected Peptide Fragment

The synthesis was carried out on a Syro-peptide synthesizer (MultiSynTech GmbH) using 24 to 96 reaction vessels. In each vessel were placed approximately 80 mg of the above resin (weight of the resin before loading). The following reaction cycles were programmed and carried out:

| Step | Reagent | Time |
|---|---|---|
| 1 | CH$_2$Cl$_2$, wash and swell (manual) | 1 × 3 min |
| 2 | DMF, wash and swell | 2 × 30 min |
| 3 | 20% piperidine/DMF | 1 × 5 min and 1 × 15 min |
| 4 | DMF, wash | 5 × 1 min |
| 5 | 3.5 eq. Fmoc amino acid/DMF + 3.5 eq. PyBOP + 7 eq. DIPEA | 1 × 60 min |
| 6 | 3.5 eq. Fmoc amino acid/DMF + 3.5 eq. HATU or PyBOP or HCTU + 7 eq. DIPEA | 1 × 60 min |
| 7 | DMF, wash | 5 × 1 min |
| 8 | 20% piperidine/DMF | 1 × 5 min and 1 × 15 min |
| 9 | DMF, wash | 5 × 1 min |
| 10 | CH$_2$Cl$_2$, wash (at the end of the synthesis) | 3 × 1 min |

Steps 5 to 9 are repeated to add each amino-acid residue.

After the synthesis of the fully protected peptide fragment had been terminated, the cleavage, cyclization and work up procedures, as described herein below, were used for the preparation of the final compounds.

Cleavage, Backbone Cyclization, Deprotection and Disulfide Bridge Formation

After assembly of the linear peptide, the resin was suspended in 1 ml of 1% TFA in CH$_2$Cl$_2$ (v/v; 0.14 mmol) for 3 minutes and filtered, and the filtrate was neutralized with 1 ml of 20% DIPEA in CH$_2$Cl$_2$ (v/v; 1.15 mmol). This procedure was repeated four times to ensure completion of the cleavage. The resin was washed three times with 1 ml of CH$_2$Cl$_2$. The CH$_2$Cl$_2$ layers containing product were evaporated to dryness.

The fully protected linear peptide was solubilised in 8 ml of dry DMF. Then 2 eq. of HATU and 2. eq. of HOAt in dry DMF (1-2 ml) and 4 eq. of DIPEA in dry DMF (1-2 ml) were added to the peptide, followed by stirring for ca. 16 h. The volatiles were removed by evaporation. The crude cyclic peptide was dissolved in 7 ml of CH$_2$Cl$_2$ and washed three times with 4.5 ml 10% acetonitrile in water (v/v). The CH$_2$Cl$_2$ layer was then evaporated to dryness.

To fully deprotect the peptide, 7 ml of cleavage cocktail TFA/DODT/thioanisol/H$_2$O (87.5:2.5:5:5) were added, and the mixture was kept for 2.5-4 h at room temperature until the reaction was completed. The reaction mixture was evaporated close to dryness and the peptide precipitated with 7 ml of cold Et$_2$O. The precipitate was washed 3 times with 4 ml of cold Et$_2$O.

The deprotected cyclic peptide is finally treated with 0.5 ml of DMSO in a solution of H$_2$O/AcOH (95:5; adjusted to pH=6 with NH$_4$HCO$_3$) for 24 h at RT to form the disulfide bridge. The reaction mixture was evaporated to dryness and the residue is purified by preparative reverse phase LC-MS.

Purification Procedure (Preparative Reverse Phase LC-MS)

Compounds were purified by reverse phase chromatography using a Phenomenex Gemini nX-C18 column, 30×100 mm, 5 μm (Cat No. 00D-4435-U0-AX) or a Waters XBridge C18 OBD column, 30×100 mm, 5 μm (Cat No. 186002982).

Mobile phases used were:
A: 0.1% TFA in Water/Acetonitrile 95/5 v/v
B: 0.1% TFA in Acetonitrile Gradient slopes in the preparative runs were adapted each time based on analytical LC-MS analysis of the crude product. As an example, a typical run (purification of Ex. 11) was executed using the Phenomenex column with a flow rate of 35 ml/min running a gradient from 0-1 min 0% B, at 1.1 min 25% B to a final of 8 min 45% B (retention time: 5.96 min in this case).

Detection: MS and UV @ 220 nm

Fractions collected were evaporated using a Genevac HT4 evaporator or a Büchi system.

Alternatively for larger amounts the following LC-purification system was used:
Column: Waters XBridge C18 OBD column, 50×250 mm, 10 μm (Cat No. 186003900)
Mobile phase A: 0.1% TFA in Water
Mobile phase B: Acetonitrile
Flow rate: 150 ml/min
Detection: UV @ 220 nm After lyophilisation the products were obtained typically as white to off-white powders and analysed by HPLC-ESI-MS methods as described below. Analytical data after preparative HPLC purification are shown in Table 1.

1.2 Analytical Methods

Analytical Method A:

Analytical HPLC retention times (RT, in minutes) were determined using an Ascentis Express C18 column, 50×3.0 mm, (cod. 53811-U—Supelco) with the following solvents A (H$_2$O+0.1% TFA) and B (CH$_3$CN+0.085% TFA) and the gradient: 0-0.05 min: 97% A, 3% B; 3.4 min: 33% A, 67% B; 3.45-3.65 min: 3% A, 97% B; 3.67-3.7 min: 97% A, 3% B. Flow rate=1.3 ml/min at 55° C.

Analytical Method B:

Analytical HPLC retention times (RT, in minutes) were determined using an Ascentis Express C18 column, 50×3.0 mm, (cod. 53811-U—Supelco) with the following solvents A (H$_2$O+0.1% TFA) and B (CH$_3$CN+0.085% TFA) and the gradient: 0-0.05 min: 97% A, 3% B; 2.95 min: 3% A 97% B; 2.95-3.15 min: 3% A, 97% B; 3.17-3.2 min: 97% A, 3% B. Flow rate=1.3 ml/min at 45° C.

1.3 Synthesis of Peptide Sequences

Examples 1-7 are shown in Table 1.

The peptides were synthesized according the general method starting with the amino acid L-tryptophan, which was grafted to the resin (Fmoc-Trp-2-chlorotrityl resin). The linear peptides were synthesized on the solid support according to the procedure described above in the following sequence: Resin-Trp P$^7$-P$^6$-P$^5$-P$^4$-P$^3$-P$^2$-P$^1$-T$^2$-T$^1$-P$^{14}$-P$^{13}$-P$^{12}$-P$^{11}$-P$^{10}$-P$^9$. The products were cleaved from the resin, cyclized, deprotected, oxidized to form the disulfide bridge, and finally purified by preparative reverse phase LC-MS as described above.

After lyophilisation the products were obtained as white to off-white powders and characterised by HPLC-MS, analytical method A as described above. For analytical data, see Ex. 1, 2, 3, 4, 5, 6, 7 in Table 1.

Example 8 is shown in Table 1.

The peptide was synthesized according the general method starting with the amino acid L-tryptophan, which was grafted to the resin (Fmoc-Trp-2-chlorotrityl resin). The linear peptide was synthesized on the solid support according to the procedure described above in the following sequence: Resin-Trp-$^D$Pro-Lys-Gln-Tyr-Cys-Ile-Thr-Trp-$^D$Pro-Gly-His-Cys-Ala-His-Tyr. The product was cleaved from the resin, cyclized, deprotected, oxidized to form the disulfide bridge, and finally purified by preparative reverse phase LC-MS as described above.

After lyophilisation the product was obtained as an off-white powder and characterised by HPLC-MS, analytical method A as described above. For analytical data, see Ex. 8 in Table 1.

Example 9 is shown in Table 1.

The peptide was synthesized according the general method starting with the amino acid L-alanine, which was grafted to the resin (Fmoc-Ala-2-chlorotrityl resin). The linear peptide was synthesized on the solid support according to the procedure described above in the following sequence: Resin-Ala-$^D$Pro-Lys-Gln-Tyr-Cys-Ile-Thr-Trp-$^D$Pro-Gly-Trp-Cys-Ala-His-Tyr. The product was cleaved from the resin, cyclized, deprotected, oxidized to form the disulfide bridge, and finally purified by preparative reverse phase LC-MS as described above.

After lyophilisation the product was obtained as an off-white powder and characterised by HPLC-MS, analytical method A as described above. For analytical data, see Ex. 9 in Table 1.

Examples 10-80 are shown in Table 1.

The peptides were synthesized according the general method starting with the amino acid L-proline, which was grafted to the resin (Fmoc-Pro-2-chlorotrityl resin). The linear peptides were synthesized on the solid support according to the procedure described above in the following sequence: Resin-Pro-T$^1$-P$^{14}$-P$^{13}$-P$^{12}$-P$^{11}$-P$^{10}$-P$^9$-P$^8$-P$^7$-P$^6$-P$^5$-P$^4$-P$^3$-P$^2$-P$^1$. The products were cleaved from the resin, cyclized, deprotected, oxidized to form the disulfide bridge, and finally purified by preparative reverse phase LC-MS as described above.

After lyophilisation the products were obtained as white to off-white powders and characterised by HPLC-MS, analytical method A as described above, except Ex. 40, for which analytical method B was used. For analytical data, see Ex. 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 in Table 1.

Examples 81-83 are shown in Table 1.

The peptides were synthesized according the general method starting with the amino acid D-proline, which was grafted to the resin (Fmoc-$^D$Pro-2-chlorotrityl resin). The linear peptides were synthesized on the solid support according to the procedure described above in the following sequence: Resin-$^D$Pro-Lys-Glu-Tyr-Cys-Ile-Thr-Trp-$^D$Pro-Gly-His-Cys-Lys-His-Tyr-T$^2$. The products were cleaved from the resin, cyclized, deprotected, oxidized to form the disulfide bridge, and finally purified by preparative reverse phase LC-MS as described above.

After lyophilisation the products were obtained as white to off-white powders and characterised by HPLC-MS, analytical method A as described above. For analytical data, see Ex. 81, 82, 83 in Table 1.

Example 84 is shown in Table 1.

The peptide was synthesized according the general method starting with the amino acid glycine, which was grafted to the resin (Fmoc-Gly-2-chlorotrityl resin). The linear peptide was synthesized on the solid support according to the procedure described above in the following sequence: Resin-Gly-His-Cys-Lys-His-Tyr-Pro-$^D$Pro-Lys-Glu-Tyr-Cys-Ile-Thr-Trp-$^D$Pro((4R)OH). The product was cleaved from the resin, cyclized, deprotected, oxidized to form the disulfide bridge, and finally purified by preparative reverse phase LC-MS as described above.

After lyophilisation the product was obtained as a white powder and characterised by HPLC-MS, analytical method A as described above. For analytical data, see Ex. 84 in Table 1.

Example 85 is shown in Table 1.

The peptide was synthesized according the general method starting with the amino acid L-cysteine, which was grafted to the resin (Fmoc-Cys-2-chlorotrityl resin). The linear peptide was synthesized on the solid support according to the procedure described above in the following sequence: Resin-Cys-Lys-His-Tyr-Pro-$^D$Pro-Lys-Glu-Tyr-Cys-Ile-Thr-Trp-$^D$Pro-Gly-Trp(5OH). The product was cleaved from the resin, cyclized, deprotected, oxidized to form the disulfide bridge, and finally purified by preparative reverse phase LC-MS as described above.

After lyophilisation the product was obtained as a white to off-white powder and characterised by HPLC-MS, analytical method A as described above. For analytical data, see Ex. 85 in Table 1.

Examples 86-88 are shown in Table 1.

The peptides were synthesized according the general method starting with the amino acid L-lysine, which was grafted to the resin (Fmoc-Lys-2-chlorotrityl resin). The linear peptides were synthesized on the solid support according to the procedure described above in the following sequence: Resin-Lys-$^D$Pro Lys-P$^{13}$-P$^{12}$-P$^{11}$-P$^{10}$-P$^9$-P$^8$-P$^7$-P$^6$-P$^5$-P$^4$-P$^3$-P$^2$-P$^1$. The products were cleaved from the resin, cyclized, deprotected, oxidized to form the disulfide bridge, and finally purified by preparative reverse phase LC-MS as described above.

After lyophilisation the products were obtained as white to off-white powders and characterised by HPLC-MS, analytical method A as described above. For analytical data, see Ex. 86, 87, 88 in Table 1.

Example 89 is shown in Table 1.

The peptide was synthesized according the general method starting with the amino acid (S)-2,4-diaminobutanoic acid, which was grafted to the resin (Fmoc-Dab-2-chlorotrityl resin). The linear peptide was synthesized on the solid support according to the procedure described above in the following sequence: Resin-Dab-$^D$Pro-Lys-Glu-Tyr-Cys-Ile-Thr-Trp-$^D$Pro-Gly-His-Cys-Lys-His-Tyr. The product was cleaved from the resin, cyclized, deprotected, oxidized to form the disulfide bridge, and finally purified by preparative reverse phase LC-MS as described above.

After lyophilisation the product was obtained as a white to off-white powder and characterised by HPLC-MS, analytical method A as described above. For analytical data, see Ex. 89 in Table 1.

Example 90 is shown in Table 1.

The peptide was synthesized according the general method starting with the amino acid (S)-piperidine-2-carboxylic acid, which was grafted to the resin (Fmoc-Pip-2-chlorotrityl resin). The linear peptide was synthesized on the solid support according to the procedure described above in the following sequence: Resin-Pip-$^D$Pro-Lys-Glu-Tyr-Cys-Ile-Thr-Trp-$^D$Pro-Gly-His-Cys-Lys-His-Tyr. The product was cleaved from the resin, cyclized, deprotected, oxidized to form the disulfide bridge, and finally purified by preparative reverse phase LC-MS as described above.

After lyophilisation the product was obtained as a white to off-white powder and characterised by HPLC-MS, analytical method A as described above. For analytical data, see Ex. 90 in Table 1.

Example 91 is shown in Table 1.

The peptide was synthesized according the general method starting with the amino acid (3S)-1,2,3,4-Tetrahydroisoquinoline-3-carboxylic acid, which was grafted to the resin (Fmoc-Tic-2-chlorotrityl resin). The linear peptide was synthesized on the solid support according to the procedure described above in the following sequence: Resin-Tic-$^D$Pro-Lys-Glu-Tyr-Cys-Ile-Thr-Trp-$^D$Pro-Gly-His-Cys-Lys-His-Tyr. The product was cleaved from the resin, cyclized, deprotected, oxidized to form the disulfide bridge, and finally purified by preparative reverse phase LC-MS as described above.

After lyophilisation the product was obtained as a white to off-white powder and characterised by HPLC-MS, analytical method A as described above. For analytical data, see Ex. 91 in Table 1.

Example 92 is shown in Table 1.

The peptide was synthesized according the general method starting with the amino acid (2S,3aS,7aS)-octahydro-1H-indole-2-carboxylic acid, which was grafted to the resin (Fmoc-Oic-2-chlorotrityl resin). The linear peptide was synthesized on the solid support according to the procedure described above in the following sequence: Resin-Oic-$^D$Pro-Lys-Glu-Tyr-Cys-Ile-Thr-Trp-$^D$Pro-Gly-His-Cys-Lys-His-Tyr. The product was cleaved from the resin, cyclized, deprotected, oxidized to form the disulfide bridge, and finally purified by preparative reverse phase LC-MS as described above.

After lyophilisation the product was obtained as a white to off-white powder and characterised by HPLC-MS, analytical method A as described above. For analytical data, see Ex. 92 in Table 1.

TABLE 1

Examples

| Ex. | P1 a) | P2 a) | P3 a) | P4 a) b) | P5 a) | P6 a) | P7 a) | P8 a) | P9 a) | P10 a) |
|---|---|---|---|---|---|---|---|---|---|---|
| 1 | Glu | His | Lys | Cys | His | Gly | $^D$Pro | Trp | Thr | Ile |
| 2 | Dab | His | Lys | Cys | His | Gly | $^D$Pro | Trp | Thr | Ile |
| 3 | Tyr | His | Lys | Cys | His | Gly | $^D$Pro | Trp | Thr | Ile |
| 4 | Tyr | His | Lys | Cys | His | Gly | $^D$Ala | Trp | Thr | Ile |
| 5 | Tyr | His | Lys | Cys | His | Gly | $^D$Pro | Trp | Thr | Ile |
| 6 | Tyr | His | Lys | Cys | His | Gly | $^D$Pro | Trp | Thr | Ile |
| 7 | Tyr | His | Ala | Cys | Trp | Gly | $^D$Pro | Trp | Thr | Ile |
| 8 | Tyr | His | Ala | Cys | His | Gly | $^D$Pro | Trp | Thr | Ile |
| 9 | Tyr | His | Ala | Cys | Trp | Gly | $^D$Pro | Trp | Thr | Ile |
| 10 | Tyr | His | Trp | Cys | Trp | Gly | $^D$Pro | Trp | Thr | Ile |
| 11 | Tyr | His | Trp | Cys | His | Gly | $^D$Pro | Trp | Thr | Ile |
| 12 | Tyr | His | Thr | Cys | His | Gly | $^D$Pro | Trp | Thr | Ile |
| 13 | Tyr | His | Lys | Cys | Trp | Gly | $^D$Pro | Trp | Thr | Ile |
| 14 | Tyr | His | Ile | Cys | His | Gly | $^D$Pro | Trp | Thr | Ile |
| 15 | Tyr | His | Glu | Cys | His | Gly | $^D$Pro | Trp | Thr | Ile |
| 16 | Tyr | His | Ala | Cys | His | Gly | $^D$Pro | Trp | Thr | Ile |
| 17 | Tyr | His | Ala | Cys | Trp | Gly | $^D$Pro | Trp | Thr | Ile |
| 18 | Tyr | His | Ala | Cys | Trp | Gly | $^D$Pro | Trp | Thr | Ile |
| 19 | Tyr | His | Ala | Cys | Trp | Gly | $^D$Pro | Trp | Thr | Ile |
| 20 | Tyr | His | Ala | Cys | Trp | Gly | $^D$Pro | Trp | Thr | Ile |
| 21 | Tyr | His | Ala | Cys | His | Gly | $^D$Pro | Trp | Thr | Ile |
| 22 | Tyr | His | Ala | Cys | Phe | Gly | $^D$Pro | Trp | Thr | Ile |
| 23 | Tyr | His | Ala | Cys | Tyr | Gly | $^D$Pro | Trp | Thr | Ile |
| 24 | Glu | His | Ala | Cys | Trp | Gly | $^D$Pro | Trp | Thr | Ile |
| 25 | Thr | His | Ala | Cys | Trp | Gly | $^D$Pro | Trp | Thr | Ile |
| 26 | His | His | Ala | Cys | Trp | Gly | $^D$Pro | Trp | Thr | Ile |
| 27 | Ala | His | Ala | Cys | Trp | Gly | $^D$Pro | Trp | Thr | Ile |
| 28 | Lys | His | Ala | Cys | His | Gly | $^D$Pro | Trp | Thr | Ile |
| 29 | His | Tyr | Ala | Cys | Trp | Gly | $^D$Pro | Trp | Thr | Ile |
| 30 | Tyr | His | Ala | Cys | His | Gly | $^D$Pro | Trp | Thr | Ile |
| 31 | Tyr | His | Ala | Cys | Trp | Gly | $^D$Pro | Trp | Thr | Ile |
| 32 | Tyr | His | Ala | Cys | Trp | Gly | $^D$Pro | Trp | Thr | Ile |
| 33 | Tyr | His | Ala | Cys | His | Gly | $^D$Pro | Trp | Thr | Ile |
| 34 | Tyr | His | Ala | Cys | Trp | Gly | $^D$Pro | Trp | Thr | Ile |
| 35 | Tyr | His | Ala | Cys | Trp | Gly | $^D$Ala | Trp | Thr | Ile |
| 36 | Tyr | His | Ala | Cys | His | Gly | $^D$Ala | Trp | Thr | Ile |
| 37 | Tyr | His | Ala | Cys | Trp | Gly | $^D$Pro | Trp | Thr | Ile |
| 38 | Tyr | His | Ala | Cys | His | Gly | $^D$Pro | Trp | Thr | Ile |
| 39 | Tyr | His | Ala | Cys | Trp | Gly | $^D$Pro | Trp | Thr | Ile |
| 40 | Tyr | His | Ala | Cys | Trp | Gly | $^D$Pro | Trp | Thr | Ile |
| 41 | Tyr | His | Lys | Cys | His | Gly | $^D$Pro | Trp | Thr | Ile |
| 42 | Tyr | His | Lys | Cys | Trp | Gly | $^D$Pro | Trp | Thr | Ile |
| 43 | Tyr | His | Lys | Cys | Trp | Gly | $^D$Pro | Trp | Thr | Ile |
| 44 | Tyr | His | Lys | Cys | His | Gly | $^D$Pro | Trp | Thr | Ile |
| 45 | Tyr | His | Lys | Cys | His | Gly | $^D$Pro | Trp | Thr | Ile |
| 46 | Tyr | His | Lys | Cys | His | Gly | $^D$Pro | Trp | Thr | Ile |
| 47 | Tyr | His | Lys | Cys | His | Gly | $^D$Pro | Trp | Thr | Ile |
| 48 | Tyr | His | Lys | Cys | His | Gly | $^D$Pro | Trp | Thr | Ile |
| 49 | Tyr | His | Lys | Cys | Tyr | Gly | $^D$Pro | Trp | Thr | Ile |
| 50 | Tyr | His | Lys | Cys | Phe(4CF$_3$) | Gly | $^D$Pro | Trp | Thr | Ile |
| 51 | Tyr | His | Lys | Cys | Trp | Gly | $^D$Pro | Trp | Thr | Ile |
| 52 | Tyr | His | Lys | Cys | Trp | Gly | $^D$Pro | Trp | Thr | Ile |
| 53 | Tyr | His | Lys | Cys | His | Gly | $^D$Pro | Trp | Thr | Ile |
| 54 | Tyr | His | Lys | Cys | His | Gly | $^D$Pro | Trp | Thr | Ile |
| 55 | Tyr | His | Lys | Cys | His | Gly | $^D$Pro | Trp | Thr | Ile |
| 56 | Tyr | His | Lys | Cys | His | Gly | $^D$Pro | Trp | Thr | Ile |
| 57 | Tyr | His | Lys | Cys | His | Gly | $^D$Pro | Trp | Thr | Ile |
| 58 | Tyr | His | Lys | Cys | His | Gly | $^D$Pro | Trp | Thr | Ile |
| 59 | Tyr | His | Lys | Cys | His | Gly | $^D$Pro | Trp | Thr | Ile |
| 60 | Tyr | His | Lys | Cys | His | Gly | $^D$Pro | Trp | Thr | Ile |
| 61 | Tyr | His | Orn | Cys | His | Gly | $^D$Pro | Trp | Thr | Ile |
| 62 | Tyr | His | Lys | Cys | His | Gly | $^D$Tic | Trp | Thr | Ile |
| 63 | Tyr | His | Lys | Cys | His | Gly | $^D$Pro | Trp | Thr | Ile |

TABLE 1-continued

| | | | | | Examples | | | | |
|---|---|---|---|---|---|---|---|---|---|
| 64 | Tyr | His | Lys | Cys | His | Gly | $^D$Pro | Trp | Thr | Ile |
| 65 | Gly | His | Lys | Cys | His | Gly | $^D$Pro | Trp | Thr | Ile |
| 66 | Asp | His | Lys | Cys | His | Gly | $^D$Pro | Trp | Thr | Ile |
| 67 | Dab | His | Lys | Cys | His | Gly | $^D$Pro | Trp | Thr | Ile |
| 68 | His | His | Lys | Cys | His | Gly | $^D$Pro | Trp | Thr | Ile |
| 69 | Dab | His | Lys | Cys | Trp | Gly | $^D$Pro | Trp | Thr | Ile |
| 70 | Tyr | His | Lys | Cys | Trp | Gly | $^D$Ala | Trp | Thr | Ile |
| 71 | Tyr | His | Lys | Cys | His | Gly | $^D$Ala | Trp | Thr | Ile |
| 72 | Tyr | His | Lys | Cys | Trp | Gly | $^D$Pro | Trp | Thr | Ile |
| 73 | Tyr | His | Lys | Cys | His | Gly | $^D$Pro | Trp | Thr | Ile |
| 74 | Tyr | His | Lys | Cys | His | Gly | $^D$Pro | Trp | Thr | Leu |
| 75 | Tyr | His | Lys | Cys | His | Gly | $^D$Pro | Trp | Thr | Val |
| 76 | Tyr | His | Lys | Cys | His | Gly | $^D$Pro | Phe(4CF$_3$) | Thr | Ile |
| 77 | Tyr | His | Ile | Cys | His | Gly | $^D$Pro | Trp | Thr | Ile |
| 78 | Tyr | His | Dap | Cys | His | Gly | $^D$Pro | Trp | Thr | Ile |
| 79 | Tyr | His | Dab | Cys | Trp | Gly | $^D$Pro | Trp | Thr | Ile |
| 80 | Tyr | His | Dab | Cys | His | Gly | $^D$Pro | Trp | Thr | Ile |
| 81 | Tyr | His | Lys | Cys | His | Gly | $^D$Pro | Trp | Thr | Ile |
| 82 | Tyr | His | Lys | Cys | His | Gly | $^D$Pro | Trp | Thr | Ile |
| 83 | Tyr | His | Lys | Cys | His | Gly | $^D$Pro | Trp | Thr | Ile |
| 84 | Tyr | His | Lys | Cys | His | Gly | $^D$Pro((4R)OH) | Trp | Thr | Ile |
| 85 | Tyr | His | Lys | Cys | Trp(5OH) | Gly | $^D$Pro | Trp | Thr | Ile |
| 86 | Tyr | His | Lys | Cys | His | Gly | $^D$Pro | Trp | Thr | Ile |
| 87 | Tyr | His | Lys | Cys | Trp | Gly | $^D$Pro | Trp | Thr | Ile |
| 88 | Tyr | His | Ala | Cys | Trp | Gly | $^D$Pro | Trp | Thr | Ile |
| 89 | Tyr | His | Lys | Cys | His | Gly | $^D$Pro | Trp | Thr | Ile |
| 90 | Tyr | His | Lys | Cys | His | Gly | $^D$Pro | Trp | Thr | Ile |
| 91 | Tyr | His | Lys | Cys | His | Gly | $^D$Pro | Trp | Thr | Ile |
| 92 | Tyr | His | Lys | Cys | His | Gly | $^D$Pro | Trp | Thr | Ile |

| Ex. | P11 a) b) | P12 a) | P13 a) | P14 a) | T1 a) | T2 a) | MS c) | RT [min] |
|---|---|---|---|---|---|---|---|---|
| 1 | Cys | Tyr | Glu | Lys | $^D$Pro | Pro | 635.9 | 1.67 |
| 2 | Cys | Tyr | Glu | Lys | $^D$Pro | Glu | 636.9 | 1.59 |
| 3 | Cys | Tyr | Glu | Lys | $^D$Pro | Glu | 658.0 | 1.69 |
| 4 | Cys | Tyr | Glu | Lys | $^D$Pro | Glu | 649.3 | 1.60 |
| 5 | Cys | Tyr | Glu | Lys | $^D$Lys | Glu | 668.4 | 1.59 |
| 6 | Cys | Tyr | Glu | Lys | $^D$Ala | Glu | 973.5 | 1.67 |
| 7 | Cys | Tyr | Gln | Lys | $^D$Pro | Glu | 982.3 | 2.01 |
| 8 | Cys | Tyr | Gln | Lys | $^D$Pro | Trp | 657.8 | 1.83 |
| 9 | Cys | Tyr | Gln | Lys | $^D$Pro | Ala | 953.3 | 2.01 |
| 10 | Cys | Tyr | Gln | Lys | $^D$Pro | Pro | 1023.8 | 2.19 |
| 11 | Cys | Tyr | Gln | Lys | $^D$Pro | Pro | 666.5 | 1.75 |
| 12 | Cys | Tyr | Gln | Lys | $^D$Pro | Pro | 638.1 | 1.68 |
| 13 | Cys | Tyr | Gln | Lys | $^D$Pro | Pro | 663.5 | 1.88 |
| 14 | Cys | Tyr | Gln | Lys | $^D$Pro | Pro | 642.0 | 1.73 |
| 15 | Cys | Tyr | Gln | Lys | $^D$Pro | Pro | 970.7 | 1.69 |
| 16 | Cys | Tyr | Trp | Lys | $^D$Pro | Pro | 647.5 | 1.89 |
| 17 | Cys | Tyr | Glu | Lys | $^D$Pro | Pro | 644.8 | 2.05 |
| 18 | Cys | Tyr | Trp | Lys | $^D$Pro | Pro | 995.2 | 2.15 |
| 19 | Cys | Tyr | Gln | Glu | $^D$Pro | Pro | 966.7 | 2.28 |
| 20 | Cys | Tyr | Gln | Ala | $^D$Pro | Pro | 937.7 | 2.45 |
| 21 | Cys | Tyr | Gln | Glu | $^D$Pro | Pro | 942.2 | 1.83 |
| 22 | Cys | Tyr | Gln | Lys | $^D$Pro | Pro | 946.7 | 2.04 |
| 23 | Cys | Tyr | Gln | Lys | $^D$Pro | Pro | 954.7 | 1.89 |
| 24 | Cys | Tyr | Gln | Lys | $^D$Pro | Pro | 949.2 | 2.01 |
| 25 | Cys | Tyr | Gln | Lys | $^D$Pro | Pro | 935.3 | 2.01 |
| 26 | Cys | Tyr | Gln | Lys | $^D$Pro | Pro | 953.7 | 1.94 |
| 27 | Cys | Tyr | Gln | Lys | $^D$Pro | Pro | 920.2 | 2.03 |
| 28 | Cys | Tyr | Gln | Lys | $^D$Pro | Pro | 923.7 | 1.57 |
| 29 | Cys | Tyr | Gln | Lys | $^D$Pro | Pro | 966.3 | 1.98 |
| 30 | Cys | Tyr | Glu | Lys | $^D$Pro | Pro | 628.5 | 1.69 |
| 31 | Cys | Tyr | Thr | Lys | $^D$Pro | Pro | 952.8 | 2.05 |
| 33 | Cys | Tyr | Ala | Lys | $^D$Pro | Pro | 937.8 | 2.07 |
| 34 | Cys | Tyr | Thr | Lys | $^D$Pro | Pro | 619.1 | 1.67 |
| 35 | Cys | Thr | Gln | Lys | $^D$Pro | Pro | 935.3 | 1.98 |
| 36 | Cys | Tyr | Gln | Lys | $^D$Pro | Pro | 953.3 | 2.01 |
| 37 | Cys | Tyr | Gln | Lys | $^D$Pro | Pro | 928.7 | 1.61 |
| 38 | Cys | Tyr | Gln | Lys | $^D$Lys | Pro | 654.9 | 1.95 |
| 39 | Cys | Tyr | Gln | Lys | $^D$Thr | Pro | 629.6 | 1.58 |
| 40 | Cys | Tyr | Gln | Lys | $^D$Ala | Pro | 953.2 | 2.04 |
| 41 | Cys | Tyr | Gln | Lys | $^D$Pro | Pro | 966.0 | 1.48 d) |
| 42 | Cys | Tyr | Glu | Lys | $^D$Ala | Pro | 638.5 | 1.67 |
| 43 | Cys | Tyr | Glu | Lys | $^D$Ala | Pro | 654.9 | 1.94 |
| 44 | Cys | Tyr | Glu | Lys | $^D$Lys | Pro | 674.0 | 1.86 |
| 45 | Cys | Tyr | Glu | Lys | $^D$Lys | Pro | 657.6 | 1.58 |
| 46 | Cys | Tyr | Glu | Lys | $^D$Tic | Pro | 668.0 | 1.86 |

TABLE 1-continued

Examples

| | | | | | | | | |
|---|---|---|---|---|---|---|---|---|
| 47 | Cys | Tyr | Glu | Lys | $^D$Pro((4S)OH) | Pro | 652.5 | 1.75 |
| 48 | Cys | Tyr | Glu | Lys | $^D$Pro((4S)NH$_2$) | Pro | 652.3 | 1.57 |
| 49 | Cys | Tyr | Glu | Lys | $^D$Pip | Pro | 652.0 | 1.74 |
| 50 | Cys | Tyr | Glu | Lys | $^D$Pro | Pro | 656.0 | 1.84 |
| 51 | Cys | Tyr | Glu | Lys | $^D$Pro | Pro | 673.3 | 2.07 |
| 52 | Cys | Tyr | Glu | Lys | $^D$Pro | Pro | 663.6 | 1.94 |
| 53 | Cys | Tyr | Glu | Dab | $^D$Pro | Pro | 654.6 | 1.95 |
| 54 | Cys | Tyr | Glu | Trp | $^D$Pro | Pro | 999.5 | 1.99 |
| 55 | Cys | Tyr | Glu | Glu | $^D$Pro | Pro | 647.6 | 1.82 |
| 56 | Cys | Tyr | Glu | His | $^D$Pro | Pro | 650.3 | 1.70 |
| 57 | Cys | Tyr | Glu | Dab | $^D$Pro | Pro | 638.0 | 1.69 |
| 58 | Cys | Tyr | Glu | Thr | $^D$Pro | Pro | 956.9 | 1.96 |
| 59 | Cys | Tyr | Glu | Gly | $^D$Pro | Pro | 934.9 | 1.90 |
| 60 | Cys | Tyr | Glu | Hse | $^D$Pro | Pro | 956.9 | 1.80 |
| 61 | Cys | Tyr | Glu | Lys | $^D$Pro | Pro | 647.3 | 1.69 |
| 62 | Cys | Tyr | Glu | Lys | $^D$Pro | Pro | 642.8 | 1.70 |
| 63 | Cys | Tyr | Glu | Lys | $^D$Pro | Pro | 667.9 | 1.89 |
| 64 | Cys | Tyr | Trp | Lys | $^D$Pro | Pro | 666.4 | 1.91 |
| 65 | Cys | Tyr | Asp | Lys | $^D$Pro | Pro | 642.5 | 1.68 |
| 66 | Cys | Tyr | Glu | Lys | $^D$Pro | Pro | 917.4 | 1.68 |
| 67 | Cys | Tyr | Glu | Lys | $^D$Pro | Pro | 631.3 | 1.67 |
| 68 | Cys | Tyr | Glu | Lys | $^D$Pro | Pro | 626.1 | 1.63 |
| 69 | Cys | Tyr | Glu | Lys | $^D$Pro | Pro | 638.8 | 1.63 |
| 70 | Cys | Tyr | Glu | Lys | $^D$Pro | Pro | 642.5 | 1.87 |
| 71 | Cys | Tyr | Glu | Lys | $^D$Pro | Pro | 655.0 | 1.91 |
| 72 | Cys | Tyr | Glu | Lys | $^D$Pro | Pro | 638.6 | 1.61 |
| 73 | Cys | Tyr | Dab | Lys | $^D$Pro | Pro | 653.9 | 1.86 |
| 74 | Cys | Tyr | Hse | Lys | $^D$Pro | Pro | 956.5 | 1.68 |
| 75 | Cys | Tyr | Glu | Lys | $^D$Pro | Pro | 647.3 | 1.72 |
| 76 | Cys | Tyr | Glu | Lys | $^D$Pro | Pro | 642.6 | 1.62 |
| 77 | Cys | Tyr | Glu | Lys | $^D$Pro | Pro | 657.0 | 1.94 |
| 78 | Cys | Tyr | Glu | Lys | $^D$Pro | Pro | 642.4 | 1.79 |
| 79 | Cys | Tyr | Glu | Lys | $^D$Pro | Pro | 633.3 | 1.71 |
| 80 | Cys | Tyr | Glu | Lys | $^D$Pro | Pro | 654.4 | 1.96 |
| 81 | Cys | Tyr | Glu | Lys | $^D$Pro | Pro | 956.4 | 1.71 |
| 82 | Cys | Tyr | Glu | Lys | $^D$Pro | Pro((4S)NH$_2$) | 977.9 | 1.52 |
| 83 | Cys | Tyr | Glu | Lys | $^D$Pro | Pro((4R)OH) | 978.4 | 1.65 |
| 84 | Cys | Tyr | Glu | Lys | $^D$Pro | Pro((4R)NH$_2$) | 652.4 | 1.59 |
| 85 | Cys | Tyr | Glu | Lys | $^D$Pro | Pro | 652.5 | 1.62 |
| 86 | Cys | Tyr | Glu | Lys | $^D$Pro | Pro | 668.9 | 1.88 |
| 87 | Cys | Tyr | Glu | Lys | $^D$Pro | Lys | 657.5 | 1.73 |
| 88 | Cys | Tyr | Glu | Lys | $^D$Pro | Lys | 674.3 | 1.87 |
| 89 | Cys | Tyr | Gln | Lys | $^D$Pro | Lys | 654.9 | 1.93 |
| 90 | Cys | Tyr | Glu | Lys | $^D$Pro | Dab | 648.3 | 1.64 |
| 91 | Cys | Tyr | Glu | Lys | $^D$Pro | Pip | 652.0 | 1.75 |
| 92 | Cys | Tyr | Glu | Lys | $^D$Pro | Tic | 667.8 | 1.93 |

$^{a)}$ Abbreviations of amino acid see listing above.
$^{b)}$ Oxidized form to form a disulfide bridge between P$^4$ and P$^{11}$
$^{c)}$ MS: either [M + 2H]$^{2+}$ or [M + 3H]$^{3+}$
$^{d)}$ Method B.

2. Biological Methods 2.1 Preparation of the Peptide Samples.

Lyophilized peptides were weighed on a Microbalance (Mettler MX5) and dissolved in aqueous 90% DMSO to a final concentration of 10 mM unless otherwise stated. Stock solutions were kept at +4° C., and protected from light.

2.2 FPR1 β-Arrestin Recruitment Assay

The PathHunter CHO—FPR1 (DiscoverX) assay was performed according to the manufacturer's protocol. In brief, CHO FPR1 β-arrestin cells were seeded at a density of 9000 cells per well in 20 µl of Ham's F12 medium (Invitrogen) in black 384-well culture plates and incubated overnight at 37° C. in a humidified atmosphere with 5% CO$_2$. The next day, serial dilutions of the β-hairpin peptidomimetics of this invention have been prepared in DMSO and subsequently diluted in HBSS buffer supplemented with 20 mM Hepes and 0.1% BSA.

For antagonistic assay, 5 µl of compound solution or buffer was added to the cells with a final DMSO concentration of 0.5% (v/v). The plate was incubated for 60 min at 37° C. with 5% CO$_2$ before addition of 100 per well of the reference agonist fMLF peptide (Sigma-Aldrich) at its EC80 concentration. After 90 min of incubation at 37° C. with 5% CO$_2$, 15 µl of beta-Glo detection reagent (Promega) were added. Reaction was developed for 20 min at room temperature and chemiluminescence was measured with a Victor2V (Perkin Elmer) luminescence reader.

Furthermore FPR1 antagonistic activity of the compounds of the current invention can be assessed e.g. in a calcium flux assay or a cell migration assay using cells stably transfected with human FPR1, and fMLF peptide as agonist. General protocols, which might be easily adapted to a specific setting by a person skilled in the art are provided in the following.

2.3 FPR1Calcium Release Antagonism Assays

The calcium flux can be assessed using human FPR1 expressing Calcium Optimized cells. These cells are dispensed in a 384-well black plate and loaded with Calcium4 Reagent (Molecular Devices, Sunnyvale, Calif.) in HBSS+ 20 mM Hepes buffer.

After 45 min at 37° C. with 5% CO$_2$, the entire plate is placed in a FLIPR (Molecular devices) at room temperature.

After recording a 20 s baseline, a concentrated solution of the β-hairpin peptidomimetics of this invention diluted in HBSS+0.1% BSA+0.5% DMSO (final concentration) is added to the cells. Fluorescence is recorded during 5 min before the dispensing of the agonist fMLF peptide at its $EC_{80}$ concentration. The signal is followed for an additional 120 s. The maximum signal is determined from control wells without inhibitor. Percentages of inhibition are then calculated from a range of compound concentrations, which are subsequently used to calculate $IC_{50}$ values (Softmax Pro, Molecular Devices).

2.4 FPR1Cell Migration Assays

The chemotactic response of dibutyryl-cAMP-differentiated HL-60 cells to a gradient of fMLF is measured using disposable Transwell® 96-well chemotaxis assay plates from Corning (3 μm pore size) according to the protocol of the manufacturer. Briefly, cells are grown under sterile conditions at 37° C. with 5% $CO_2$ in flasks containing 15% DMEM, 15% Ham's F12 medium (Invitrogen), 30% IMDM, 30% RPMI media, 10% FCS, glutamine, penicillin/streptomycin (all media components are from Life Technologies) and Insulin-Transferrin-Selenium supplements at 1× (from Invitrogen). 2 Days before use dibutyryl-cAMP is added at 500 μM to induce cell differentiation. For the assay, cells are pelleted by centrifugation, washed once in RPMI+ 0.5% bovine serum albumin (BSA), and resuspended to give $4 \times 10^6$ cells/ml in RPMI+0.5% BSA. 50 μl of cell suspension is applied to the top of the assay filter. The β-hairpin peptidomimetics, diluted in the same assay medium, are added to both top and bottom chambers. The cells are allowed to migrate for 2 hours at 37° C. into the bottom chamber of the assay plate containing 10 nM of fMLF. Migrated cells are transferred to a new microtiter plate and CellTiterGlo reagent (Promega) is added. After 10 min incubation at room temperature, luminescence signal is measured using a Victor2V (Perkin Elmer) multimode reader. Data normalization is performed using the number of any cells that had migrated in the absence of the β-hairpin peptidomimetic and the number of cells that had randomly migrated in absence of fMLF [these values are taken as 100% (no inhibitory activity) and 0%, respectively]. From a range of compound concentrations $IC_{50}$ are determined using Prism5 (GraphPad software).

2.5 Results

TABLE 2

Biological Results: FPR1 β-arrestin recruitment assay

| Ex. | β-Arrestin $IC_{50}$ (nM) |
|---|---|
| 1 | 165 ± 76 |
| 2 | 144 ± 101 |
| 3 | 169 ± 70 |
| 4 | 77 ± 22 |
| 5 | 124 ± 67 |
| 6 | 124 ± 10 |
| 7 | 60 ± 3 |
| 8 | 147 ± 88 |
| 9 | 188 ± 6 |
| 10 | 89 ± 5 |
| 11 | 177 ± 121 |
| 12 | 178 ± 17 |
| 13 | 71 ± 33 |
| 14 | 35 ± 17 |
| 15 | 321 ± 77 |
| 16 | 36 ± 7 |
| 17 | 68 ± 13 |
| 18 | 62 ± 10 |
| 19 | 63 ± 15 |
| 20 | 76 ± 16 |
| 21 | 132 ± 14 |
| 22 | 166 ± 1 |
| 23 | 184 ± 43 |
| 24 | 131 ± 37 |
| 25 | 294 ± 44 |
| 26 | 342 ± 115 |
| 27 | 404 ± 141 |
| 28 | 590 ± 69 |
| 29 | 735 ± 38 |
| 30 | 189 ± 79 |
| 31 | 202 ± 58 |
| 32 | 278 ± 21 |
| 33 | 598 ± 169 |
| 34 | 685 ± 68 |
| 35 | 213 ± 96 |
| 36 | 458 ± 156 |
| 37 | 195 ± 11 |
| 38 | 641 ± 129 |
| 39 | 133 ± 18 |
| 40 | 96 ± 30 |
| 41 | 65 ± 36 |
| 42 | 126 ± 78 |
| 43 | 126 ± 53 |
| 44 | 385 ± 79 |
| 45 | 56 ± 36 |
| 46 | 39 ± 14 |
| 47 | 41 ± 8 |
| 48 | 29 ± 13 |
| 49 | 22 ± 1 |
| 50 | 172 ± 121 |
| 51 | 54 ± 21 |
| 52 | 53 ± 29 |
| 53 | 16 ± 4 |
| 54 | 57 ± 33 |
| 55 | 73 ± 2 |
| 56 | 82 ± 29 |
| 57 | 197 ± 0 |
| 58 | 250 ± 129 |
| 59 | 24 ± 9 |
| 60 | 44 ± 10 |
| 61 | 313 ± 110 |
| 62 | 21 ± 13 |
| 63 | 15 ± 13 |
| 64 | 37 ± 24 |
| 65 | 111 ± 59 |
| 66 | 177 ± 28 |
| 67 | 194 ± 79 |
| 68 | 239 ± 163 |
| 69 | 248 ± 163 |
| 70 | 69 ± 18 |
| 71 | 77 ± 4 |
| 72 | 633 ± 295 |
| 73 | 138 ± 61 |
| 74 | 153 ± 16 |
| 75 | 232 ± 71 |
| 76 | 114 ± 71 |
| 77 | 50 ± 20 |
| 78 | 271 ± 95 |
| 79 | 93 ± 54 |
| 80 | 290 ± 148 |
| 81 | 530 ± 3 |
| 82 | 376 ± 276 |
| 83 | 82 ± 51 |
| 84 | 485 ± 61 |
| 85 | 13 ± 3 |
| 86 | 109 ± 35 |
| 87 | 54 ± 21 |
| 88 | 325 ± 19 |
| 89 | 189 ± 65 |
| 90 | 161 ± 73 |
| 91 | 115 ± 27 |
| 92 | 267 ± 115 |

The invention claimed is:

1. A compound of the general formula (I),

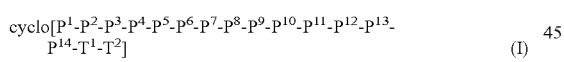
(I)

wherein
- $T^1$ is $^D$Ala; $^D$Lys; $^D$Pro; $^D$Pro((4S)NH$_2$); $^D$Pro((4S)OH); $^D$Pip; $^D$Thr; or $^D$Tic;
- $T^2$ is Ala; Dab; Lys; Glu; Pro; Pro((4R)NH$_2$); Pro((4S)NH$_2$); Pro((4R)OH); Pro((4S)OH); Pip; Tic; Oic; or Trp;
- $P^1$ is Gly; Ala; Dab; Lys; Asp; Glu; Thr; His; or Tyr;
- $P^2$ is His; or Tyr;
- $P^3$ is Ala; Ile; Dab; Dap; Lys; Orn; Glu; Thr; or Trp;
- $P^4$ is Cys;
- $P^5$ is Phe; Phe(4CF$_3$); Tyr; Trp; Trp(5OH); or His;
- $P^6$ is Gly;
- $P^7$ is $^D$Ala; $^D$Pro; $^D$Pro((4R)OH); or $^D$Tic;
- $P^8$ is Phe(4CF$_3$); Trp;
- $P^9$ is Thr;
- $P^{10}$ is Ile; Leu; or Val;
- $P^{11}$ is Cys;
- $P^{12}$ is Tyr;
- $P^{13}$ is Ala; Dab; Asp; Glu; Gln; hSer; Thr; or Trp; and
- $P^{14}$ is Gly; Ala; Dab; Lys; Glu; Gln; hSer; Thr; His; or Trp;
and wherein $P^4$ and $P^{11}$ are optionally forming a disulfide bridge;

or a pharmaceutically acceptable salt thereof.

2. A compound according to claim 1, which is selected from

| | |
|---|---|
| cyclo(-Glu-His-Lys-Cys-His-Gly-$^D$Pro-Trp-Thr-Ile-Cys-Tyr-Glu-Lys-$^D$Pro-Pro-) | (SEQ ID NO: 1); |
| cyclo(-Dab-His-Lys-Cys-His-Gly-$^D$Pro-Trp-Thr-Ile-Cys-Tyr-Glu-Lys-$^D$Pro-Glu-) | (SEQ ID NO: 2); |
| cyclo(-Tyr-His-Lys-Cys-His-Gly-$^D$Pro-Trp-Thr-Ile-Cys-Tyr-Glu-Lys-$^D$Pro-Glu-) | (SEQ ID NO: 3); |
| cyclo(-Tyr-His-Lys-Cys-His-Gly-$^D$Ala-Trp-Thr-Ile-Cys-Tyr-Glu-Lys-$^D$Pro-Glu-) | (SEQ ID NO: 4); |
| cyclo(-Tyr-His-Lys-Cys-His-Gly-$^D$Pro-Trp-Thr-Ile-Cys-Tyr-Glu-Lys-$^D$Lys-Glu-) | (SEQ ID NO: 5); |
| cyclo(-Tyr-His-Lys-Cys-His-Gly-$^D$Pro-Trp-Thr-Ile-Cys-Tyr-Glu-Lys-$^D$Ala-Glu-) | (SEQ ID NO: 6); |
| cyclo(-Tyr-His-Ala-Cys-Trp-Gly-$^D$Pro-Trp-Thr-Ile-Cys-Tyr-Gln-Lys-$^D$Pro-Glu-) | (SEQ ID NO: 7); |
| cyclo(-Tyr-His-Ala-Cys-His-Gly-$^D$Pro-Trp-Thr-Ile-Cys-Tyr-Gln-Lys-$^D$Pro-TrP-) | (SEQ ID NO: 8); |
| cyclo(-Tyr-His-Ala-Cys-Trp-Gly-$^D$Pro-Trp-Thr-Ile-Cys-Tyr-Gln-Lys-$^D$Pro-Ala-) | (SEQ ID NO: 9); |
| cyclo(-Tyr-His-Trp-Cys-Trp-Gly-$^D$Pro-Trp-Thr-Ile-Cys-Tyr-Gln-Lys-$^D$Pro-Pro-) | (SEQ ID NO: 10); |

-continued

| | |
|---|---|
| cyclo(-Tyr-His-Trp-Cys-His-Gly-$^D$Pro-Trp-Thr-Ile-Cys-Tyr-Gln-Lys-$^D$Pro-Pro-) | (SEQ ID NO: 11); |
| cyclo(-Tyr-His-Thr-Cys-His-Gly-$^D$Pro-Trp-Thr-Ile-Cys-Tyr-Gln-Lys-$^D$Pro-Pro-) | (SEQ ID NO: 12); |
| cyclo(-Tyr-His-Lys-Cys-Trp-Gly-$^D$Pro-Trp-Thr-Ile-Cys-Tyr-Gln-Lys-$^D$Pro-Pro-) | (SEQ ID NO: 13); |
| cyclo(-Tyr-His-Ile-Cys-His-Gly-$^D$Pro-Trp-Thr-Ile-Cys-Tyr-Gln-Lys-$^D$Pro-Pro-) | (SEQ ID NO: 14); |
| cyclo(-Tyr-His-Glu-Cys-His-Gly-$^D$Pro-Trp-Thr-Ile-Cys-Tyr-Gln-Lys-$^D$Pro-Pro-) | (SEQ ID NO: 15); |
| cyclo(-Tyr-His-Ala-Cys-His-Gly-$^D$Pro-Trp-Thr-Ile-Cys-Tyr-Trp-Lys-$^D$Pro-Pro-) | (SEQ ID NO: 16); |
| cyclo(-Tyr-His-Ala-Cys-Trp-Gly-$^D$Pro-Trp-Thr-Ile-Cys-Tyr-Glu-Lys-$^D$Pro-Pro-) | (SEQ ID NO: 17); |
| cyclo(-Tyr-His-Ala-Cys-Trp-Gly-$^D$Pro-Trp-Thr-Ile-Cys-Tyr-Trp-Lys-$^D$Pro-Pro-) | (SEQ ID NO: 18); |
| cyclo(-Tyr-His-Ala-Cys-Trp-Gly-$^D$Pro-Trp-Thr-Ile-Cys-Tyr-Gln-Glu-$^D$Pro-Pro-) | (SEQ ID NO: 19); |
| cyclo(-Tyr-His-Ala-Cys-Trp-Gly-$^D$Pro-Trp-Thr-Ile-Cys-Tyr-Gln-Ala-$^D$Pro-Pro-) | (SEQ ID NO: 20); |
| cyclo(-Tyr-His-Ala-Cys-His-Gly-$^D$Pro-Trp-Thr-Ile-Cys-Tyr-Gln-Glu-$^D$Pro-Pro-) | (SEQ ID NO: 21); |
| cyclo(-Tyr-His-Ala-Cys-Phe-Gly-$^D$Pro-Trp-Thr-Ile-Cys-Tyr-Gln-Lys-$^D$Pro-Pro-) | (SEQ ID NO: 22); |
| cyclo(-Tyr-His-Ala-Cys-Tyr-Gly-$^D$Pro-Trp-Thr-Ile-Cys-Tyr-Gln-Lys-$^D$Pro-Pro-) | (SEQ ID NO: 23); |
| cyclo(-Glu-His-Ala-Cys-Trp-Gly-$^D$Pro-Trp-Thr-Ile-Cys-Tyr-Gln-Lys-$^D$Pro-Pro-) | (SEQ ID NO: 24); |
| cyclo(-Thr-His-Ala-Cys-Trp-Gly-$^D$Pro-Trp-Thr-Ile-Cys-Tyr-Gln-Lys-$^D$Pro-Pro-) | (SEQ ID NO: 25); |
| cyclo(-His-His-Ala-Cys-Trp-Gly-$^D$Pro-Trp-Thr-Ile-Cys-Tyr-Gln-Lys-$^D$Pro-Pro-) | (SEQ ID NO: 26); |
| cyclo(-Ala-His-Ala-Cys-Trp-Gly-$^D$Pro-Trp-Thr-Ile-Cys-Tyr-Gln-Lys-$^D$Pro-Pro-) | (SEQ ID NO: 27); |
| cyclo(-Lys-His-Ala-Cys-His-Gly-$^D$Pro-Trp-Thr-Ile-Cys-Tyr-Gln-Lys-$^D$Pro-Pro-) | (SEQ ID NO: 28); |
| cyclo(-His-Tyr-Ala-Cys-Trp-Gly-$^D$Pro-Trp-Thr-Ile-Cys-Tyr-Gln-Lys-$^D$Pro-Pro-) | (SEQ ID NO: 29); |
| cyclo(-Tyr-His-Ala-Cys-Trp-Gly-$^D$Pro-Trp-Thr-Ile-Cys-Tyr-Glu-Lys-$^D$Pro-Pro-) | (SEQ ID NO: 30); |
| cyclo(-Tyr-His-Ala-Cys-Trp-Gly-$^D$Pro-Trp-Thr-Ile-Cys-Tyr-Thr-Lys-$^D$Pro-Pro-) | (SEQ ID NO: 31); |
| cyclo(-Tyr-His-Ala-Cys-Trp-Gly-$^D$Pro-Trp-Thr-Ile-Cys-Tyr-Ala-Lys-$^D$Pro-Pro-) | (SEQ ID NO: 32); |
| cyclo(-Tyr-His-Ala-Cys-His-Gly-$^D$Pro-Trp-Thr-Ile-Cys-Tyr-Thr-Lys-$^D$Pro-Pro-) | (SEQ ID NO: 33); |
| cyclo(-Tyr-His-Ala-Cys-Trp-Gly-$^D$Pro-Trp-Thr-Ile-Cys-Thr-Gln-Lys-$^D$Pro-Pro-) | (SEQ ID NO: 34); |
| cyclo(-Tyr-His-Ala-Cys-Trp-Gly-$^D$Ala-Trp-Thr-Ile-Cys-Tyr-Gln-Lys-$^D$Pro-Pro-) | (SEQ ID NO: 35); |
| cyclo(-Tyr-His-Ala-Cys-His-Gly-$^D$Ala-Trp-Thr-Ile-Cys-Tyr-Gln-Lys-$^D$Pro-Pro-) | (SEQ ID NO: 36); |
| cyclo(-Tyr-His-Ala-Cys-Trp-Gly-$^D$Pro-Trp-Thr-Ile-Cys-Tyr-Gln-Lys-$^D$Lys-Pro-) | (SEQ ID NO: 37); |
| cyclo(-Tyr-His-Ala-Cys-Trp-Gly-$^D$Pro-Trp-Thr-Ile-Cys-Tyr-Gln-Lys-$^D$Thr-Pro-) | (SEQ ID NO: 38); |
| cyclo(-Tyr-His-Ala-Cys-Trp-Gly-$^D$Pro-Trp-Thr-Ile-Cys-Tyr-Gln-Lys-$^D$Ala-Pro-) | (SEQ ID NO: 39); |
| cyclo(-Tyr-His-Ala-Cys-Trp-Gly-$^D$Pro-Trp-Thr-Ile-Cys-Tyr-Gln-Lys-$^D$Pro-Pro-) | (SEQ ID NO: 40); |
| cyclo(-Tyr-His-Lys-Cys-His-Gly-$^D$Pro-Trp-Thr-Ile-Cys-Tyr-Glu-Lys-$^D$Ala-Pro-) | (SEQ ID NO: 41); |
| cyclo(-Tyr-His-Lys-Cys-Trp-Gly-$^D$Pro-Trp-Thr-Ile-Cys-Tyr-Glu-Lys-$^D$Ala-Pro-) | (SEQ ID NO: 42); |
| cyclo(-Tyr-His-Lys-Cys-Trp-Gly-$^D$Pro-Trp-Thr-Ile-Cys-Tyr-Glu-Lys-$^D$Lys-Pro-) | (SEQ ID NO: 43); |
| cyclo(-Tyr-His-Lys-Cys-His-Gly-$^D$Pro-Trp-Thr-Ile-Cys-Tyr-Glu-Lys-$^D$Lys-Pro-) | (SEQ ID NO: 44); |
| cyclo(-Tyr-His-Lys-Cys-His-Gly-$^D$Pro-Trp-Thr-Ile-Cys-Tyr-Glu-Lys-$^D$Tic-Pro-) | (SEQ ID NO: 45); |
| cyclo(-Tyr-His-Lys-Cys-His-Gly-$^D$Pro-Trp-Thr-Ile-Cys-Tyr-Glu-Lys-$^D$Pro((4S)OH)-Pro-) | (SEQ ID NO: 46); |
| cyclo(-Tyr-His-Lys-Cys-His-Gly-$^D$Pro-Trp-Thr-Ile-Cys-Tyr-Glu-Lys-$^D$Pro((4S)NH$_2$)-Pro-) | (SEQ ID NO: 47); |
| cyclo(-Tyr-His-Lys-Cys-His-Gly-$^D$Pro-Trp-Thr-Ile-Cys-Tyr-Glu-Lys-$^D$Pip-Pro-) | (SEQ ID NO: 48); |
| cyclo(-Tyr-His-Lys-Cys-Tyr-Gly-$^D$Pro-Trp-Thr-Ile-Cys-Tyr-Glu-Lys-$^D$Pro-Pro-) | (SEQ ID NO: 49); |
| cyclo(-Tyr-His-Lys-Cys-Phe(4CF$_3$)-Gly-$^D$Pro-Trp-Thr-Ile-Cys-Tyr-Glu-Lys-$^D$Pro-Pro-) | (SEQ ID NO: 50); |
| cyclo(-Tyr-His-Lys-Cys-Trp-Gly-$^D$Pro-Trp-Thr-Ile-Cys-Tyr-Glu-Lys-$^D$Pro-Pro-) | (SEQ ID NO: 51); |
| cyclo(-Tyr-His-Lys-Cys-Trp-Gly-$^D$Pro-Trp-Thr-Ile-Cys-Tyr-Glu-Dab-$^D$Pro-Pro-) | (SEQ ID NO: 52); |
| cyclo(-Tyr-His-Lys-Cys-His-Gly-$^D$Pro-Trp-Thr-Ile-Cys-Tyr-Glu-Trp-$^D$Pro-Pro-) | (SEQ ID NO: 53); |
| cyclo(-Tyr-His-Lys-Cys-His-Gly-$^D$Pro-Trp-Thr-Ile-Cys-Tyr-Glu-Glu-$^D$Pro-Pro-) | (SEQ ID NO: 54); |
| cyclo(-Tyr-His-Lys-Cys-His-Gly-$^D$Pro-Trp-Thr-Ile-Cys-Tyr-Glu-His-$^D$Pro-Pro-) | (SEQ ID NO: 55); |
| cyclo(-Tyr-His-Lys-Cys-His-Gly-$^D$Pro-Trp-Thr-Ile-Cys-Tyr-Glu-Dab-$^D$Pro-Pro-) | (SEQ ID NO: 56); |
| cyclo(-Tyr-His-Lys-Cys-His-Gly-$^D$Pro-Trp-Thr-Ile-Cys-Tyr-Glu-Thr-$^D$Pro-Pro-) | (SEQ ID NO: 57); |
| cyclo(-Tyr-His-Lys-Cys-His-Gly-$^D$Pro-Trp-Thr-Ile-Cys-Tyr-Glu-Gly-$^D$Pro-Pro-) | (SEQ ID NO: 58); |
| cyclo(-Tyr-His-Lys-Cys-His-Gly-$^D$Pro-Trp-Thr-Ile-Cys-Tyr-Glu-Hse-$^D$Pro-Pro-) | (SEQ ID NO: 59); |
| cyclo(-Tyr-His-Lys-Cys-His-Gly-$^D$Pro-Trp-Thr-Ile-Cys-Tyr-Glu-Lys-$^D$Pro-Pro-) | (SEQ ID NO: 60); |
| cyclo(-Tyr-His-Orn-Cys-His-Gly-$^D$Pro-Trp-Thr-Ile-Cys-Tyr-Glu-Lys-$^D$Pro-Pro-) | (SEQ ID NO: 61); |
| cyclo(-Tyr-His-Lys-Cys-His-Gly-$^D$Tic-Trp-Thr-Ile-Cys-Tyr-Glu-Lys-$^D$Pro-Pro-) | (SEQ ID NO: 62); |
| cyclo(-Tyr-His-Lys-Cys-His-Gly-$^D$Pro-Trp-Thr-Ile-Cys-Tyr-Trp-Lys-$^D$Pro-Pro-) | (SEQ ID NO: 63); |
| cyclo(-Tyr-His-Lys-Cys-His-Gly-$^D$Pro-Trp-Thr-Ile-Cys-Tyr-Asp-Lys-$^D$Pro-Pro-) | (SEQ ID NO: 64); |
| cyclo(-Gly-His-Lys-Cys-His-Gly-$^D$Pro-Trp-Thr-Ile-Cys-Tyr-Glu-Lys-$^D$Pro-Pro-) | (SEQ ID NO: 65); |
| cyclo(-Asp-His-Lys-Cys-His-Gly-$^D$Pro-Trp-Thr-Ile-Cys-Tyr-Glu-Lys-$^D$Pro-Pro-) | (SEQ ID NO: 66); |
| cyclo(-Dab-His-Lys-Cys-His-Gly-$^D$Pro-Trp-Thr-Ile-Cys-Tyr-Glu-Lys-$^D$Pro-Pro-) | (SEQ ID NO: 67); |
| cyclo(-His-His-Lys-Cys-His-Gly-$^D$Pro-Trp-Thr-Ile-Cys-Tyr-Glu-Lys-$^D$Pro-Pro-) | (SEQ ID NO: 68); |
| cyclo(-Dab-His-Lys-Cys-Trp-Gly-$^D$Pro-Trp-Thr-Ile-Cys-Tyr-Glu-Lys-$^D$Pro-Pro-) | (SEQ ID NO: 69); |
| cyclo(-Tyr-His-Lys-Cys-Trp-Gly-$^D$Ala-Trp-Thr-Ile-Cys-Tyr-Glu-Lys-$^D$Pro-Pro-) | (SEQ ID NO: 70); |
| cyclo(-Tyr-His-Lys-Cys-His-Gly-$^D$Ala-Trp-Thr-Ile-Cys-Tyr-Glu-Lys-$^D$Pro-Pro-) | (SEQ ID NO: 71); |
| cyclo(-Tyr-His-Lys-Cys-His-Gly-$^D$Pro-Trp-Thr-Ile-Cys-Tyr-Dab-Lys-$^D$Pro-Pro-) | (SEQ ID NO: 72); |
| cyclo(-Tyr-His-Lys-Cys-His-Gly-$^D$Pro-Trp-Thr-Ile-Cys-Tyr-Hse-Lys-$^D$Pro-Pro-) | (SEQ ID NO: 73); |
| cyclo(-Tyr-His-Lys-Cys-His-Gly-$^D$Pro-Trp-Thr-Leu-Cys-Tyr-Glu-Lys-$^D$Pro-Pro-) | (SEQ ID NO: 74); |
| cyclo(-Tyr-His-Lys-Cys-His-Gly-$^D$Pro-Trp-Thr-Val-Cys-Tyr-Glu-Lys-$^D$Pro-Pro-) | (SEQ ID NO: 75); |
| cyclo(-Tyr-His-Lys-Cys-His-Gly-$^D$Pro-Phe(4CF$_3$)-Thr-Ile-Cys-Tyr-Glu-Lys-$^D$Pro-Pro-) | (SEQ ID NO: 76); |
| cyclo(-Tyr-His-Ile-Cys-His-Gly-$^D$Pro-Trp-Thr-Ile-Cys-Tyr-Glu-Lys-$^D$Pro-Pro-) | (SEQ ID NO: 77); |
| cyclo(-Tyr-His-Dap-Cys-His-Gly-$^D$Pro-Trp-Thr-Ile-Cys-Tyr-Glu-Lys-$^D$Pro-Pro-) | (SEQ ID NO: 78); |
| cyclo(-Tyr-His-Dab-Cys-Trp-Gly-$^D$Pro-Trp-Thr-Ile-Cys-Tyr-Glu-Lys-$^D$Pro-Pro-) | (SEQ ID NO: 79); |
| cyclo(-Tyr-His-Dab-Cys-His-Gly-$^D$Pro-Trp-Thr-Ile-Cys-Tyr-Glu-Lys-$^D$Pro-Pro-) | (SEQ ID NO: 80); |
| cyclo(-Tyr-His-Lys-Cys-His-Gly-$^D$Pro-Trp-Thr-Ile-Cys-Tyr-Glu-Lys-$^D$Pro-Pro)((4S)NH$_2$)- | (SEQ ID NO: 81); |
| cyclo(-Tyr-His-Lys-Cys-His-Gly-$^D$Pro-Trp-Thr-Ile-Cys-Tyr-Glu-Lys-$^D$Pro-Pro((4R)OH)-) | (SEQ ID NO: 82); |
| cyclo(-Tyr-His-Lys-Cys-His-Gly-$^D$Pro-Trp-Thr-Ile-Cys-Tyr-Glu-Lys-$^D$Pro-Pro((4R)NH$_2$)-) | (SEQ ID NO: 83); |

```
                               -continued
cyclo(-Tyr-His-Lys-Cys-His-Gly-DPro((4R)OH)-Trp-Thr-Ite-Cys-Tyr-Glu-Lys-   (SEQ ID NO: 84);
DPro-Pro-)
cyclo(-Tyr-His-Lys-Cys-Trp(5OH)-Gly-DPro-Trp-Thr-Ile-Cys-Tyr-Glu-Lys-      (SEQ ID NO: 85);
DPro-Pro-)
cyclo(-Tyr-His-Lys-Cys-His-Gly-DPro-Trp-Thr-Ile-Cys-Tyr-Glu-Lys-DPro-Lys-) (SEQ ID NO: 86);
cyclo(-Tyr-His-Lys-Cys-Trp-Gly-DPro-Trp-Thr-Ile-Cys-Tyr-Glu-Lys-DPro-Lys-) (SEQ ID NO: 87);
cyclo(-Tyr-His-Ala-Cys-Trp-Gly-DPro-Trp-Thr-Ile-Cys-Tyr-Gln-Lys-DPro-Lys-) (SEQ ID NO: 88);
cyclo(-Tyr-His-Lys-Cys-His-Gly-DPro-Trp-Thr-Ile-Cys-Tyr-Glu-Lys-DPro-Dab-) (SEQ ID NO: 89);
cyclo(-Tyr-His-Lys-Cys-His-Gly-DPro-Trp-Thr-Ile-Cys-Tyr-Glu-Lys-DPro-Pip-) (SEQ ID NO: 90);
cyclo(-Tyr-His-Lys-Cys-His-Gly-DPro-Trp-Thr-Ile-Cys-Tyr-Glu-Lys-DPro-Tic-) (SEQ ID NO: 91);
cyclo(-Tyr-His-Lys-Cys-His-Gly-DPro-Trp-Thr-Ile-Cys-Tyr-Glu-Lys-DPro-Oic-) (SEQ ID NO: 92);
``` wherein the Cys residues are optionally forming a disulfide bridge;
or a pharmaceutically acceptable salt thereof.

3. A compound according to claim 2 which is selected from

```
cyclo(-Tyr-His-Ile-Cys-His-Gly-DPro-Trp-Thr-Ile-Cys-Tyr-Gln-Lys-DPro-Pro-)       (SEQ ID NO: 14);
cyclo(-Tyr-His-Lys-Cys-His-Gly-DPro-Trp-Thr-Ile-Cys-Tyr-Glu-Lys-DPro((4S)        (SEQ ID NO: 46);
OH)-Pro-)
cyclo(-Tyr-His-Lys-Cys-His-Gly-DPro-Trp-Thr-Ile-Cys-Tyr-Glu-Lys-DPro((4S)        (SEQ ID NO: 47);
NH2)-Pro-)
cyclo(-Tyr-His-Lys-Cys-His-Gly-DPro-Trp-Thr-Ile-Cys-Tyr-Glu-Lys-DPip-Pro-)       (SEQ ID NO: 48);
cyclo(-Tyr-His-Lys-Cys-Tyr-Gly-DPro-Trp-Thr-Ile-Cys-Tyr-Glu-Lys-DPro-Pro-)       (SEQ ID NO: 49);
cyclo(-Tyr-His-Lys-Cys-Trp-Gly-DPro-Trp-Thr-Ile-Cys-Tyr-Glu-Lys-DPro-Pro-)       (SEQ ID NO: 51);
cyclo(-Tyr-His-Lys-Cys-His-Gly-DPro-Trp-Thr-Ile-Cys-Tyr-Glu-Hse-DPro-Pro-)       (SEQ ID NO: 59);
cyclo(-Tyr-His-Lys-Cys-His-Gly-DPro-Trp-Thr-Ile-Cys-Tyr-Glu-Lys-DPro-Pro-)       (SEQ ID NO: 60);
cyclo(-Tyr-His-Lys-Cys-His-Gly-DTic-Trp-Thr-Ile-Cys-Tyr-Glu-Lys-DPro-Pro-)       (SEQ ID NO: 62);
cyclo(-Tyr-His-Lys-Cys-His-Gly-DPro-Trp-Thr-Ile-Cys-Tyr-Trp-Lys-DPro-Pro-)       (SEQ ID NO: 63);
cyclo(-Tyr-His-Lys-Cys-His-Gly-DPro-Trp-Thr-Ile-Cys-Tyr-Asp-Lys-DPro-Pro-)       (SEQ ID NO: 64);
cyclo(-Tyr-His-Ile-Cys-His-Gly-DPro-Trp-Thr-Ile-Cys-Tyr-Glu-Lys-DPro-Pro-)       (SEQ ID NO: 77);
cyclo(-Tyr-His-Lys-Cys-Trp(5OH)-Gly-DPro-Trp-Thr-Ile-Cys-Tyr-Glu-Lys-            (SEQ ID NO: 85);
DPro-Pro-)
cyclo(-Tyr-His-Lys-Cys-Trp-Gly-DPro-Trp-Thr-Ile-Cys-Tyr-Glu-Lys-DPro-Lys-)       (SEQ ID NO: 87);
``` wherein the Cys residues are optionally forming a disulfide bridge;
or a pharmaceutically acceptable salt thereof.

4. A pharmaceutical composition containing a compound or a mixture of compounds according to claim 1 and at least one pharmaceutically inert carrier.

5. A pharmaceutical composition according to claim 4 in a form suitable for oral, topical, transdermal, injection, buccal, transmucosal, rectal, pulmonary, or inhalation administration.

6. A compound of formula (I) according to claim 1, wherein the compound of formula (I) is in the form of a pharmaceutically acceptable salt.

7. A medicament comprising a compound according to claim 1 as a pharmaceutically active substance having antagonistic activity against the FPR1 receptor.

8. A method for treating a disease or condition, comprising:
administering a compound according to claim 1 to a subject in need thereof, said disease or condition to be treated is selected from the group consisting of periodontitis, inflammation and glioblastoma.

9. A process for the preparation of a compound according to claim 1 which comprises
(a) coupling a functionalized solid support with an N-protected derivative of that amino acid which in the desired end-product is in position $T^1$ or $T^2$ or $P^1$ to $P^{14}$ as defined above; any functional group which may be present in said N-protected amino acid derivative being likewise protected;
(b) removing the N-protecting group from the product obtained in step (a);
(c) coupling the product thus obtained with an N-protected derivative of that amino acid which in the desired end-product is in the position of the next element (T or P), following counterclockwise or clockwise the sequence according to general formula (I) in —COOH to —NH$_2$ orientation; any functional group which may be present in said N-protected amino acid derivative being likewise protected;
(d) removing the N-protecting group from the product thus obtained;
(e) repeating steps (c) and (d) until all amino acid residues have been introduced;
(f) if desired, selectively deprotecting one or several protected functional group(s) present in the molecule and chemically transforming the reactive group(s) thus liberated;
(g) detaching the product thus obtained from the solid support;
(h) cyclizing the product cleaved from the solid support;
(i) removing any protecting groups present on functional groups of any members of the chain of amino acid residues and, if desired, any protecting group(s) which may in addition be present in the molecule;
(j) if desired, forming a disulfide bridge between the sulfhydryl containing residues at $P^4$ and $P^{11}$;
(k) if desired, implementing additional chemical transformations of one or more reactive group(s) present in the molecule; and
(l) if desired, converting the product thus obtained into a pharmaceutically acceptable salt or converting a pharmaceutically acceptable, or unacceptable, salt thus obtained into the corresponding free compound of formula (I) or into a different, pharmaceutically acceptable salt.

10. A method for manufacturing a medicament, comprising:
adding a compound according to claim 1 with one or more physiological acceptable carriers, diluents, excipients or auxiliaries, wherein said adding is carried out by mixing, dissolving, granulating, coated tablet-making, levigating, emulsifying, encapsulating, entrapping or lyophilizing processes.

11. A compound of formula (I) according to claim 1 suitable for use as a medicament in the treatment of a disease or disorder associated with the FPR1 receptor selected from the group consisting of periodontitis, inflammation and glioblastoma.

12. A pharmaceutical composition according to claim 4 in the form of tablets, dragees, capsules, solutions, liquids, gels, plaster, creams, ointments, syrup, slurries, suspensions, spray, nebulizer or suppositories.

* * * * *